US012637445B2

(12) United States Patent
Tamayo et al.

(10) Patent No.: US 12,637,445 B2
(45) Date of Patent: May 26, 2026

(54) KIF18A INHIBITORS

(71) Applicant: AMGEN INC., Thousand Oaks, CA (US)

(72) Inventors: Nuria A. Tamayo, Newbury Park, CA (US); Abhisek Banerjee, Karnataka (IN); Matthew Paul Bourbeau, Woodland Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 1007 days.

(21) Appl. No.: 17/632,338

(22) PCT Filed: Aug. 3, 2020

(86) PCT No.: PCT/US2020/044800

§ 371 (c)(1),
(2) Date: Feb. 2, 2022

(87) PCT Pub. No.: WO2021/026101

PCT Pub. Date: Feb. 11, 2021

(65) Prior Publication Data

US 2022/0281843 A1 Sep. 8, 2022

Related U.S. Application Data

(60) Provisional application No. 62/882,271, filed on Aug. 2, 2019.

(51) Int. Cl.

| | |
|---|---|
| ***C07D 401/14*** | (2006.01) |
| ***C07D 401/04*** | (2006.01) |
| ***C07D 405/14*** | (2006.01) |
| ***C07D 413/14*** | (2006.01) |
| ***C07D 471/04*** | (2006.01) |
| ***C07D 471/08*** | (2006.01) |

(52) U.S. Cl.

CPC ......... *C07D 401/14* (2013.01); *C07D 401/04* (2013.01); *C07D 405/14* (2013.01); *C07D 413/14* (2013.01); *C07D 471/04* (2013.01); *C07D 471/08* (2013.01)

(58) Field of Classification Search

CPC ........................................................ C07D 1/14

See application file for complete search history.

(56) References Cited

U.S. PATENT DOCUMENTS

| | | | | |
|---|---|---|---|---|
| 2002/0068687 | A1 | 6/2002 | Chen | |
| 2008/0194557 | A1 | 8/2008 | Barbosa | |
| 2008/0200458 | A1 | 8/2008 | Barbosa | |
| 2020/0056015 | A1* | 2/2020 | Yatagai | C08L 91/00 |

FOREIGN PATENT DOCUMENTS

| | | | |
|---|---|---|---|
| AU | 686334 | B2 | 2/1998 |
| CN | 102872018 | B | 7/2015 |
| JP | H05208911 | A | 8/1993 |
| JP | H09508127 | A | 8/1997 |
| JP | 2000508657 | A | 7/2000 |
| JP | 2002541108 | A | 12/2002 |
| JP | 2009521460 | A | 6/2009 |
| JP | 2009521480 | A | 6/2009 |
| JP | 2009161465 | A | 7/2009 |
| JP | 2016505519 | A | 2/2016 |
| WO | 1997038983 | A1 | 10/1997 |
| WO | 2000059509 | A1 | 10/2000 |
| WO | 2005047268 | A2 | 5/2005 |
| WO | 2007076035 | A2 | 7/2007 |
| WO | 2007081517 | A2 | 7/2007 |
| WO | 2014072244 | A1 | 5/2014 |
| WO | 2014072914 | A1 | 5/2014 |
| WO | 2020132649 | A1 | 6/2020 |
| WO | 2020132653 | A1 | 6/2020 |

OTHER PUBLICATIONS

McMahon, Gerald. "VEGF receptor signaling in tumor angiogenesis." The oncologist 5.S1 (2000): 3-10. (Year: 2000).*

(Continued)

*Primary Examiner* — Andrew D Kosar

*Assistant Examiner* — Connor K English

(74) *Attorney, Agent, or Firm* — Elsa D. Lemoine

(57) ABSTRACT

Compounds of formula (I): (I), as defined herein, and synthetic intermediates thereof, which are capable of modulating KIF18A protein thereby influencing the process of cell cycle and cell proliferation to treat cancer and cancer-related diseases. The invention also includes pharmaceutical compositions, including the compounds, and methods of treating disease states related to the activity of KIF18A.

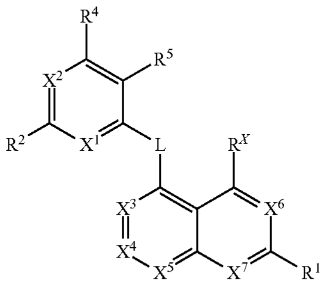

46 Claims, No Drawings

(56) References Cited

OTHER PUBLICATIONS

Zhang, Chunpeng et al. "Kif18A is involved in human breast carcinogenesis." Carcinogenesis vol. 31,9 (2010): 1676-84. doi: 10.1093/carcin/bgq134 (Year: 2010).*

Nagahara, Makoto et al. "Kinesin 18A expression: clinical relevance to colorectal cancer progression." International journal of cancer vol. 129,11 (2011): 2543-52. doi: 10.1002/ijc.25916 (Year: 2011).*

Liao W, Huang G, Liao Y, Yang J, Chen Q, Xiao S, Jin J, He S, Wang C. High KIF18A expression correlates with unfavorable prognosis in primary hepatocellular carcinoma. Oncotarget. Nov. 15, 2014;5(21):10271-9. doi: 10.18632/oncotarget.2082. PMID: 25431949; PMCID: PMC4279371. (Year: 2014).*

Li, Xiaoqing et al. "High kinesin family member 18A expression correlates with poor prognosis in primary lung adenocarcinoma." Thoracic cancer vol. 10,5 (2019): 1103-1110. doi: 10.1111/1759-7714.13051.*

Chen, Q I et al. "Elevated expression of KIF18A enhances cell proliferation and predicts poor survival in human clear cell renal carcinoma." Experimental and therapeutic medicine vol. 12,1 (2016): 377-383. doi: 10.3892/etm.2016.3335.*

Cho, S.Y., Kim, S., Kim, G. et al. Integrative analysis of KIF4A, 9, 18A, and 23 and their clinical significance in low-grade glioma and glioblastoma. Sci Rep 9, 4599 (2019). https://doi.org/10.1038/s41598-018-37622-3.*

Rucksaken, Rucksak et al. "Proteomic analysis to identify plasma orosomucoid 2 and kinesin 18A as potential biomarkers of cholangiocarcinoma." Cancer biomarkers : section A of Disease markers vol. 12,2 (2012): 81-95. doi: 10.3233/CBM-130296.*

Braun et al., "Synthesis and Biological Evaluation of Optimized Inhibitors of the Mitotic Kinesin Kif18A", Acs Chemical Biology, vol. 10, pp. 554-560 (2014).

International Search Report and Written Opinion issued in International Patent Application No. PCT/US20/44800 mailed Sep. 22, 2020.

Noolvi et al., "A comparative QSAR analysis and molecular docking studies of quinazoline derivatives as tyrosine kinase (EGFR) inhibitors: A rational approach to anticancer drug design," Journal of Saudi Chemical Society, vol. 17, pp. 361-379 (2013).

* cited by examiner

KIF18A INHIBITORS

CROSS REFERENCES TO RELATED APPLICATIONS

This application is a National Stage Application under 35 U.S.C. § 371 of International Application No. PCT/US20/44800, having an international filing date of Aug. 3, 2020, which is published on Feb. 11, 2021, as WO 2021/026101, which is claiming priority from U.S. Provisional Application No. 62/882,271, having a filing date of Aug. 2, 2019.

The invention relates to the field of pharmaceutical agents and, more specifically, is directed to compounds and compositions useful for modulating KIF18A, and to uses and methods for managing cell proliferation and for treating cancer.

BACKGROUND OF THE INVENTION

Cancer is one of the most widespread diseases afflicting mankind and a major cause of death worldwide. In an effort to find an effective treatment or a cure for one or more of the many different cancers, over the last couple of decades, numerous groups have invested a tremendous amount of time, effort and financial resources. However, to date, of the available cancer treatments and therapies, only a few offer any considerable degree of success.

Cancer is often characterized by unregulated cell proliferation. Damage to one or more genes, responsible for the cellular pathways, which control progress of proliferation through the cell cycle and centrosome cycle, can cause the loss of normal regulation of cell proliferation. These deregulated genes can code for various tumor suppressor or oncogene proteins, which participate in a cascade of events, leading to unchecked cell-cycling progression and cell proliferation. Various kinase and kinesin proteins have been identified, which play key roles in cell cycle and mitotic regulation and progression of normal dividing cells and cancer cells.

Kinesins are molecular motors that play important roles in cell division and intracellular vesicle and organelle transport. Mitotic kinesin play roles in several aspects of spindle assembly, chromosome segregation, centrosome separation and dynamics (reviewed in O. Rath and F. Kozielski, *Nature Review Cancer,* 12:527-39, 2012). Human kinesins are categorized into 14 subfamilies based on sequence homology within the so-called "motor domain", this domains ATPase activity drives unidirectional movement along microtubules (MTs). The non-motor domain of these proteins is responsible for cargo attachment; a "cargo" can include any one of a variety of different membranous organelles, signal transduction scaffolding systems, and chromosomes. Kinesins use the energy of ATP hydrolysis to move cargo along polarized microtubules. Thus, kinesins are often called "plus-end" or "minus-end" directed motors.

KIF18A gene belongs to Kinesin-8 subfamily and is a plus-end-directed motor. KIF18A is believed to influence dynamics at the plus end of kinetochore microtubules to control correct chromosome positioning and spindle tension. Depletion of human KIF18A leads to longer spindles, increased chromosome oscillation at metaphase, and activation of the mitotic spindle assembly checkpoint in HeLa cervical cancer cells (MI Mayr et al, Current Biology 17, 488-98, 2007). KIF18A appears to be viable target for the treatment of cancer. KIF18A is overexpressed in various types of cancers, including but not limited to colon, breast, lung, pancreas, prostate, bladder, head, neck, cervix, and ovarian cancers. Further, genetic deletion or knockdown, or inhibition of KIF18A effects mitotic spindle apparatus in cancer cell lines. Particularly, inhibition of KIF18A has been found to induce mitotic cell arrest, a known vulnerability that can promote cell death in mitosis via apoptosis, mitotic catastrophe, or multipolarity driven lethality or death after mitotic slippage in interphase. Accordingly, there has been a strong interest in finding inhibitors of KIF18A proteins.

Thus, the inhibition of KIF18A ATPase activity is a promising approach for the development of novel anticancer agents.

SUMMARY OF THE INVENTION

An aspect of the present invention is a new class of compounds useful for modulating KIF18A protein alone or in a bound complex with microtubules for treating KIF18A-mediated conditions and/or diseases, including cancer, inflammation, or ciliopathologies.

The compounds provided by the invention have MT-based KIF18A modulatory activity and, in particular, KIF18A inhibitory activity. To this end, the invention also provides the use of these compounds, as well as pharmaceutically acceptable salts thereof, in the preparation and manufacture of a pharmaceutical composition or medicament for therapeutic, prophylactic, acute or chronic treatment of KIF18A mediated diseases and disorders, including without limitation, cancer. Thus, the compounds of the invention are useful in the manufacture of anti-cancer medicaments. The invention also provides processes for making compounds of Formula I, as well as intermediates useful in such processes.

In embodiment 1, the present invention provides a compound of Formula (I), A compound of formula I:

(I)

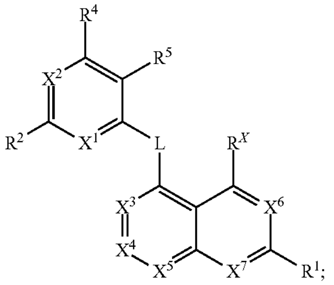

or any pharmaceutically-acceptable salt thereof, wherein:

$X^1$ is N or $CR^6$;

$X^2$ is N or $CR^{3a}$;

$X^3$ is N or $CR^{3b}$;

$X^4$ is N or $CR^{3c}$;

$X^5$ is N or $CR^{3d}$;

$X^6$ is N or $CR^{3e}$;

$X^7$ is N or $CR^{3f}$;

wherein no more than 3 of $X^3$, $X^4$, $X^5$ and $X^6$ are N;

$R^1$ is —CN, or a group —Z—$R^8$ wherein Z is —$C_{0-4}$alk-, —$NR^7$—, —$NR^7SO_2$—, —$SO_2NR^7$—, —N═S(═O)—$(R^7)_2$ (wherein the two $R^7$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S), —$NR^7$—S(═O)(═NH), —S(═O)(═NH)—, —S—, —S(=O)—, —$SO_2$—, $C_{0-4}$alk-O—, —(C=O)—, —(C=O)$NR^7$—, —C=N(OH)—, or —$NR^7$(C=O);

$R^2$ is halo or a group —Y—$R^9$, wherein Y is —$C_{0-4}$alk-, —$NR^a$—, —N($C_{1-4}$alk)-, —NH—$(CH_2)_{0-4}$—, —C(=O)$NR^aR^a$($C_{1-4}$alk), —O—$(CH_2)_{0-4}$, $C_{0-4}$alk-S—, $C_{0-4}$alk-S=O, $C_{0-4}$alk-S$(=O)_2$, —$SO_2NR^a$—$C_{0-4}$ alk-, —$C_{0-4}$alk-S(=O)(=NH)—, —O—$C_{0-4}$alk-, —$C_{0-4}$alk-(C=O)—, —$C_{0-4}$alk-(C=O)—O—, or —N=S(=O)<;

L is —NW, —O—, —S—, S=O, or S$(=O)_2$;

$R^3$ is H, $C_{1-4}$alk, or $C_{1-4}$haloalk;

$R^{3a}$ is H, halo, $C_{1-8}$alk, or $C_{1-4}$haloalk;

$R^{3b}$ is H, halo, $C_{1-8}$alk, or $C_{1-4}$haloalk;

$R^{3c}$ is H, halo, $C_{1-8}$alk, or $C_{1-4}$haloalk;

$R^{3d}$ is H, halo, $C_{1-8}$alk, or $C_{1-4}$haloalk;

$R^{3e}$ is H, halo, $C_{1-8}$alk, or $C_{1-4}$haloalk;

$R^{3f}$ is H, halo, $C_{1-8}$alk, or $C_{1-4}$haloalk;

$R^4$ is H, halo, $R^{4a}$ or $R^{4b}$;

$R^5$ is H, halo, $C_{1-8}$alk, or $C_{1-4}$haloalk;

$R^6$ is H, halo, $C_{1-8}$alk, $C_{1-4}$haloalk, —O—$C_{1-8}$alk, or —O—$R^{6a}$; wherein $R^{6a}$ is a saturated or partially-saturated 3-, 4-, 5-, or 6-membered monocyclic ring containing 0, 1, 2 or 3 N atoms and 0, 1, or 2 atoms selected from O and S;

$R^X$ is selected from H,

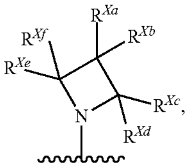

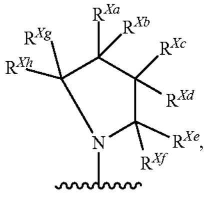

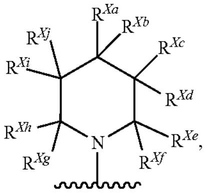

or

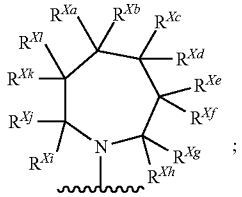

;

Each of $R^{Xa}$, $R^{Xb}$, $R^{Xc}$, $R^{Xd}$, $R^{Xe}$, $R^{Xf}$, $R^{Xg}$, $R^{Xh}$, $R^{Xi}$, $R^{Xj}$, $R^{Xk}$ and $R^{Xl}$ is H, halo, $R^{Xm}$, or $R^{Xn}$;

or alternatively, each of $R^{Xa}$ and $R^{Xb}$ pair, $R^{Xc}$ and $R^{Xd}$ pair, $R^{Xe}$ and $R^{Xf}$ pair, $R^{Xg}$ and $R^{Xh}$ pair, $R^{Xi}$ and $R^{Xj}$ pair, and $R^{Xk}$ and $R^{Xl}$ pair, independently, can combine with the carbon atom attached to each of them to form a saturated or partially-saturated 3-, 4-, 5-, 6-membered monocyclic ring spiro to the azetidinyl, pyrrolidinyl, piperidinyl, morpholinyl, or azepanyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, —$OR^a$, —$OC_{1-4}$haloalk, CN, —$NR^aR^a$, or oxo;

$R^7$ is H, $R^{7a}$, or $R^{7b}$;

$R^8$ is H, $R^{8a}$, or $R^{9b}$;

$R^9$ is $R^{9a}$ or $R^{9b}$;

$R^{4a}$, $R^{Xm}$, $R^{7a}$, $R^{8a}$, and $R^{9a}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0, 1, or 2 atoms selected from O and S, which is substituted by 0, 1, 2 or 3 group(s) selected from F, Cl, Br, $C_{1-6}$alk, $C_{1-4}$haloalk, —$OR^a$, —$OC_{1-4}$ haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S$(=O)_2R^b$, —S$(=O)_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^b$, —N($R^a$)S$(=O)_2R^b$, —N($R^a$)S$(=O)_2NR^aR^b$, —$NR^aC_{2-6}$alk$NR^aR^a$, —$NR^aC_{2-6}$alk$OR^a$, —$C_{1-6}$alk$NR^aR^a$, —$C_{1-6}$alk$O^a$, —$C_{1-6}$alkN($R^a$)C(=O)$R^b$, —$C_{1-6}$ alkOC(=O)$R^b$, —$C_{1-6}$alkC(=O)$NR^aR^a$, —$C_{1-6}$alkC (=O)$OR^a$, $R^{10}$, and oxo;

$R^{4b}$, $R^{Xn}$, $R^{8b}$, $R^{8b}$, and $R^{9b}$ is independently, at each instance, selected from the group consisting of $C_{1-6}$alk substituted by 0, 1, 2, 3, 4, or 5 group(s) selected from F, Cl, Br, —$OR^a$, —$OC_{1-4}$haloalk, or CN;

$R^{10}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$ alk$NR^aR^a$, —$OC_{2-6}$alk$OR^a$, —$SR^a$, —S(=O)$R^b$, —S$(=O)_2R^b$, —S$(=O)_2NR^aR^a$, —$NR^aR^a$, —N($R^a$)C (=O)$R^b$, —N($R^a$)C(=O)$OR^b$, —N($R^a$)C(=O)$NR^a$ $R^a$, —N($R^a$)C(=$NR^a$)$NR^aR^a$, —N($R^a$)S$(=O)_2R^b$, —N($R^a$)S$(=O)_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$ alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, and oxo;

$R^a$ is independently, at each instance, H or $R^b$; and $R^b$ is independently, at each instance, $C_{1-6}$alk, phenyl, or benzyl, wherein the $C_{1-6}$alk is being substituted by 0, 1, 2 or 3 substituents selected from halo, —OH, —$OC_{1-4}$ alk, —$NH_2$, —$NHC_{1-4}$alk, —OC(=O)$C_{1-4}$alk, or —N($C_{1-4}$alk)$C_{1-4}$alk; and the phenyl or benzyl is being substituted by 0, 1, 2 or 3 substituents selected from halo, $C_{1-4}$alk, $C_{1-3}$haloalk, —OH, —$OC_{1-4}$alk, —$NH_2$, —$NHC_{1-4}$alk, —OC(=O)$C_{1-4}$alk, or —N($C_{1-4}$alk) $C_{1-4}$ alk.

In embodiment 2, the present invention provides compounds wherein $X^1$ is $CR^6$; $X^2$ is $CR^{3a}$; $X^3$ is N; $X^4$ is $CR^{3c}$; $X^5$ is N; $X^6$ is $CR^{3e}$; and $X^7$ is $CR^{3f}$; having the formula (Ia):

(Ia)

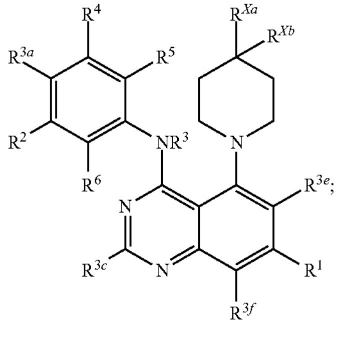

wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, —$OR^a$, —$OC_{1-4}$haloalk, CN, —$NR^aR^a$, or oxo.

In embodiment 3, the present invention provides compounds wherein $X^1$ is N; $X^2$ is $CR^{3a}$; $X^3$ is N; $X^4$ is $CR^{3c}$; $X^5$ is N; $X^6$ is $CR^{3e}$; and $X^7$ is $CR^{3f}$; having the formula (Ib):

(Ib)

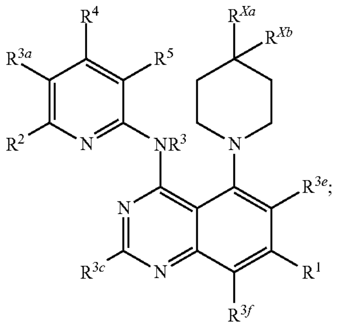

wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, —$OR^a$, —$OC_{1-4}$haloalk, CN, —$NR^aR^a$, or oxo.

In embodiment 4, the present invention provides compounds wherein $X^1$ is $CR^6$; $X^2$ is N; $X^3$ is N; $X^4$ is $CR^{3c}$; $X^5$ is N; $X^6$ is $CR^{3e}$; and $X^7$ is $CR^{3f}$; having the formula (Ic):

(Ic)

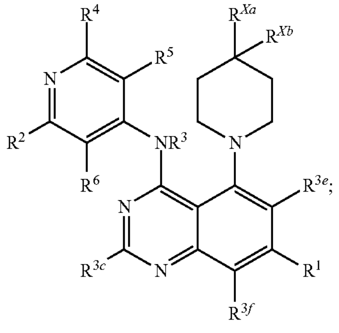

Wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, —$OR^a$, —$OC_{1-4}$haloalk, CN, —$NR^aR^a$, or oxo.

In embodiment 5, the present invention provides compounds wherein $X^1$ is N; $X^2$ is N; $X^3$ is N; $X^4$ is $CR^{3c}$; $X^5$ is N; $X^6$ is $CR^{3e}$; and $X^7$ is $CR^{3f}$; having the formula (Id):

(Id)

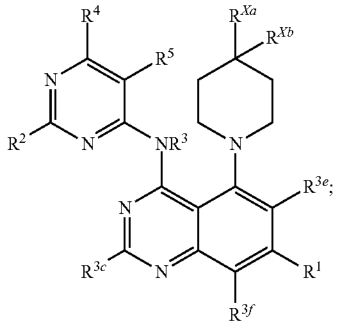

wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, —$OR^a$, —$OC_{1-4}$haloalk, CN, —$NR^aR^a$, or oxo.

In embodiment 6, the present invention provides compounds wherein $X^1$ is $CR^6$; $X^2$ is $CR^{3a}$; $X^3$ is N; $X^4$ is N; $X^5$ is $CR^{3d}$; $X^6$ is $CR^{3e}$; and $X^7$ is $CR^{3f}$; having the formula (Ie):

(Ie)

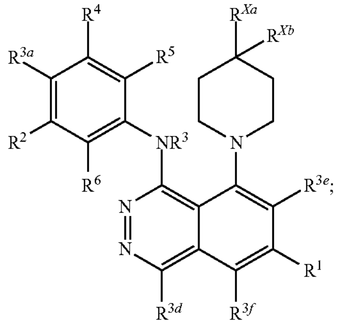

wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, —$OR^a$, —$OC_{1-4}$haloalk, CN, —$NR^aR^a$, or oxo.

In embodiment 7, the present invention provides compounds in accordance with any of the above embodiments, or pharmaceutically acceptable salts thereof, wherein $R^3$ is H or methyl.

In embodiment 8, the present invention provides compounds in accordance with any of the above embodiments, or pharmaceutically acceptable salts thereof, wherein each of $R^{Xc}$, $R^{Xd}$, $R^{Xe}$, $R^{Xf}$, $R^{Xg}$, $R^{Xh}$, $R^{Xi}$, $R^{Xj}$, $R^{Xk}$, and $R^{Xl}$ is H, halo, $C_{1-6}$alk, or $C_{1-4}$haloalk; and each of $R^{Xa}$ and $R^{Xb}$ pair combine with the carbon atom attached to each of them form a saturated 3-, 4-, or 5-membered monocyclic ring spiro to the piperidinyl ring; wherein said ring contains 0, 1, 2 or 3 N atoms and 0 or 1 atoms selected from O and S.

In embodiment 9, the present invention provides compounds in accordance with any of the above embodiments, or pharmaceutically acceptable salts thereof, wherein each of $R^{Xc}$, $R^{Xd}$, $R^{Xe}$, $R^{Xf}$, $R^{Xg}$, $R^{Xh}$, $R^{Xi}$, $R^{Xj}$, $R^{Xk}$, and $R^{Xl}$ is H, methyl, or ethyl; and each of $R^{Xa}$ and $R^{Xb}$ pair combine with the carbon atom attached to each of them form a cyclopropyl, cyclobutyl, or cyclopentyl ring spiro to the piperidinyl ring.

In embodiment 10, the present invention provides compounds in accordance with any of the above embodiments, or pharmaceutically acceptable salts thereof, wherein the group

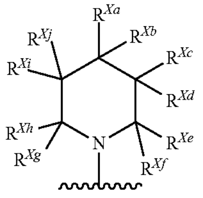

is selected from:

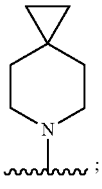 ; 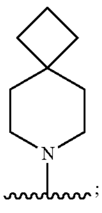 ; 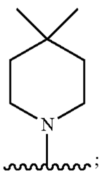 ; or 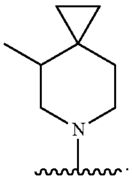 .

In embodiment 11, the present invention provides compounds in accordance with any of the above embodiments, or pharmaceutically acceptable salts thereof, wherein the group

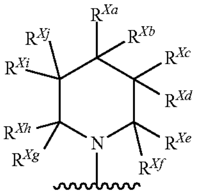 is 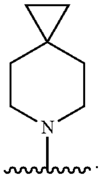 .

In embodiment 12, the present invention provides compounds in accordance with any of the above embodiments, or pharmaceutically acceptable salts thereof, wherein $R^1$ is —CN, or a group —Z—$R^8$, wherein Z is absent, —NH—, —$NHSO_2$—, —$SO_2NH$—, —N═S(═O)—$(R^{11})_2$ (wherein the two $R^7$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S), —S(═O)(═NH)—, —S—, —S(═O)—, —$SO_2$—, —(C═O)—, —(C═O)NH—, or —NH(C═O)—; and $R^8$ is selected from:

(a) H;

(b) cyclopropyl, cyclobutyl, cyclopentyl, cyclohexyl, oxiranyl, oxetanyl, tetrahydrofuranyl, azetidinyl, imidazolyl, morpholinyl, pyrrolidinyl, piperazinyl,

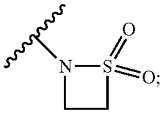 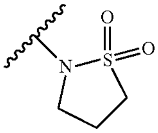 ; 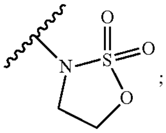 ;

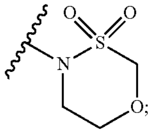 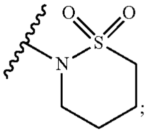 ; 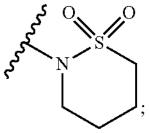 ;

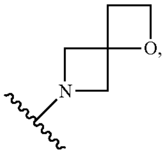 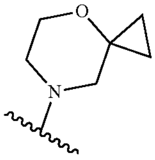 , or 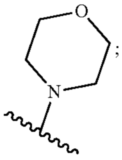 ;

wherein each said ring is substituted by 0, 1, 2 or 3 group(s) selected from wherein each ring is substituted by 0, 1, 2 or 3 OH, F, methyl, —$CH_2OH$, —C(═O)$OCH_3$, —C(═O)OC$(CH_3)_3$, $NH_2$, CN, and oxo; or (c) $C_{1-6}$alk substituted by 0, 1, 2 or 3 OH, F, —C(═O)$OCH_3$, —$NH_2$, —NH($CH_3$), or —N$(CH_3)_2$.

In embodiment 13, the present invention provides compounds in accordance with any of the above embodiments, or pharmaceutically acceptable salts thereof, wherein $R^1$ is —CN, or a group —Z—$R^8$, wherein Z is absent, —NH—, —$NHSO_2$—, —$SO_2NH$—, —N═S(═O)—$(R^7)_2$ (wherein the two $R^7$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S), —S(═O)(═NH)—, —S—, —S(═O)—, —$SO_2$—, —(C═O)—, —(C═O)NH—, or —NH(C═O)—; and (a) $R^8$ is H;

(b) $R^8$ is oxetanyl, cyclopropyl; or (c) $R^8$ is $C_{1-6}$alk substituted by 0, 1, 2 or 3 OH group(s).

In embodiment 14, the present invention provides compounds in accordance with any of the above embodiments, or pharmaceutically acceptable salts thereof, wherein $R^1$ is a group —Z—$R^8$, wherein Z is —N═S(═O)—$(R^7)_2$; wherein each $R^7$ is independently selected from the group consisting of H, methyl, or isopropyl; or the two $R^7$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S, which is selected from:

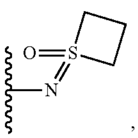 , 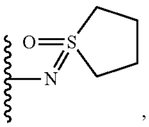 , or 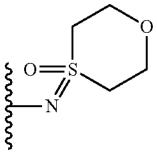 .

In embodiment 15, the present invention provides compounds in accordance with any of the above embodiments, or pharmaceutically acceptable salts thereof, wherein $R^1$ is a group —Z—$R^8$, wherein Z is —$SO_2$; —$NHSO_2$—; —$SO_2NH$—; or —S(═O)(═NH)—; and $R^8$ is H, oxetanyl, cyclopropyl, or $R^8$ is $C_{1-6}$alk substituted by 0, 1, 2 or 3 OH group(s).

In embodiment 16, the present invention provides compounds in accordance with any of the above embodiments, or pharmaceutically acceptable salts thereof, wherein $R^1$ is a group —Z—$R^8$, wherein Z is —$NHSO_2$— and $R^8$ is —$CH_2$—$CH_2$—OH.

In embodiment 17, the present invention provides compounds in accordance with any of the above embodiments, or pharmaceutically acceptable salts thereof, wherein $R^1$ is a group —Z—$R^8$, wherein Z is —$SO_2$; and $R^8$ is methyl.

In embodiment 18, the present invention provides compounds in accordance with any of the above embodiments, or pharmaceutically acceptable salts thereof, wherein $R^1$ is a group —Z—$R^8$, wherein Z is —S(═O)(═NH)—; and $R^8$ is cyclopropyl.

In embodiment 19, the present invention provides compounds in accordance with any of the above embodiments, or pharmaceutically acceptable salts thereof, wherein $R^1$ is H.

In embodiment 20, the present invention provides compounds in accordance with any of the above embodiments, or pharmaceutically acceptable salts thereof, wherein $R^2$ is halo or a group —Y—$R^9$, wherein Y is absent, —NH—, —NH—$(CH_2)_{0-4}$—, or —O—$(CH_2)_{0-4}$; and $R^9$ is a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —OH, —$OC_{1-4}$haloalk, CN, $R^{10}$, and oxo; or $R^9$ is $C_{1-6}$alk substituted by 0, 1, 2, 3, 4, or 5 group(s) selected from F, Cl, Br, —OH, —$OC_{1-4}$haloalk, or CN.

In embodiment 21, the present invention provides compounds in accordance with embodiments 1-17, or pharmaceutically acceptable salts thereof, wherein R is a saturated 5- or 6-membered monocyclic ring wherein each said ring contains 0, 1, or 2 N atoms and 0 or 1 O atom, and wherein each said ring is substituted by 0, 1, 2 or 3 group(s) selected from F, Cl, Br, $C_{1-6}$alk, $C_{1-4}$haloalk, —OH, —$OC_{1-4}$haloalk, CN, $R^{10}$, and oxo.

In embodiment 22, the present invention provides compounds in accordance with any of the above embodiments, or pharmaceutically acceptable salts thereof, wherein $R^2$ is (a) halo; (b) a group —Y—$R^9$, wherein Y is absent; and $R^9$ is morpholinyl, piperidinyl, azetidinyl, pyrrolidinyl, cyclopropyl, cyclobutyl, cyclopentyl, cyclohexyl, piperazinyl, tetrahydrofuranyl,

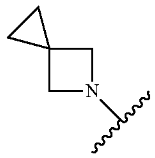, 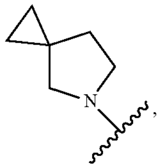, 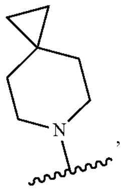,

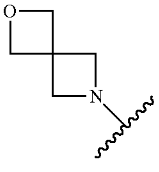, 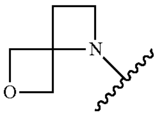, 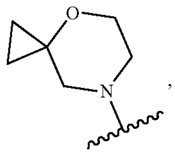,

-continued

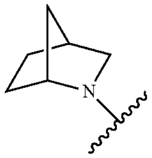, 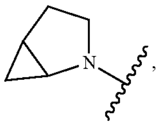, 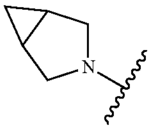,

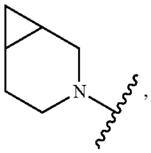, 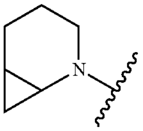, 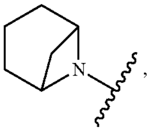,

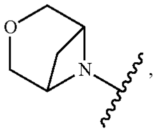, 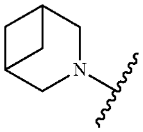, 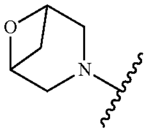,

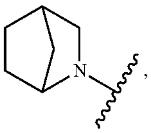, 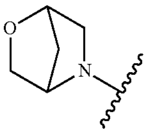, 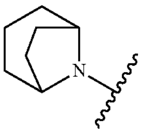,

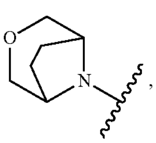, 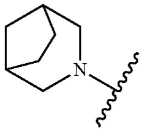, 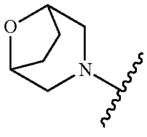,

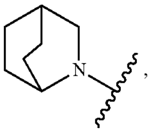, 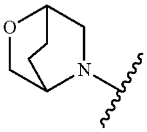, 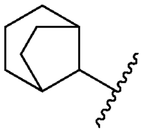,

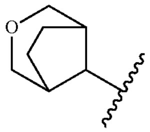, 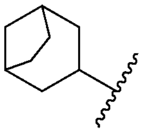, 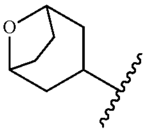,

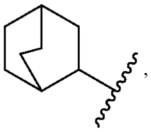, 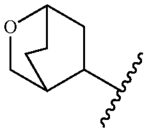, 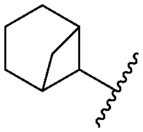,

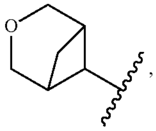, 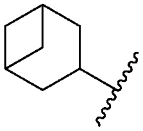, 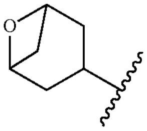,

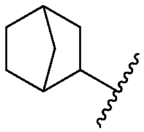, or 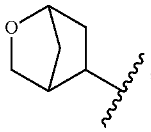;

wherein each said ring is substituted by 0, 1, 2 or 3 group(s) selected from F, Cl, Br, methyl, $CF_3$, —OH, —$OCHF_2$, CN, and oxo; or (c) a group —Y—$R^9$, wherein Y is NH, —O—, —O—$(CH_2)$—, —O—$(CH_2)$—$(CH_2)$—, or —O—$(CH_2)$—$(CH_2)$—$(CH_2)$—, and wherein $R^{13}$ is

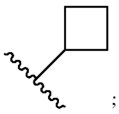 ; 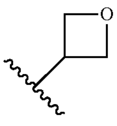 ; 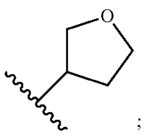 ;

or $R^9$ is $C_{1-6}$alk substituted by 0, 1, 2, 3, 4, or 5 group(s) selected from F, Cl, Br, methyl, $CF_3$, —OH, or CN.

In embodiment 23, the present invention provides compounds in accordance with any of the above embodiments, or pharmaceutically acceptable salts thereof, wherein $R^2$ is morpholinyl or piperidinyl substituted by 0, 1, 2 or 3 group(s) selected from F, Cl, Br, methyl, $CF_3$, —OH, —$OCHF_2$, CN, or oxo.

In embodiment 24, the present invention provides compounds in accordance with any of the above embodiments, or pharmaceutically acceptable salts thereof, wherein $R^2$ is morpholinyl substituted by 1, 2 or 3 methyl group(s)

In embodiment 25, the present invention provides compounds in accordance with any of the above embodiments, or pharmaceutically acceptable salts thereof, wherein $R^2$ is piperidinyl substituted by 1, 2 or 3 fluoro group(s).

In embodiment 26, the present invention provides compounds in accordance with any of the above embodiments, or pharmaceutically acceptable salts thereof wherein $R^2$ is

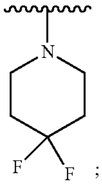 ; 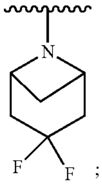 ; 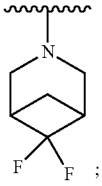 ; or 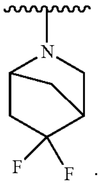 .

In embodiment 27, the present invention provides compounds in accordance with any of the above embodiments, or pharmaceutically acceptable salts thereof, wherein $R^2$ is methyl or —O—$(CH_2)$—$(CH_2)$—$CF_3$.

In embodiment 28, the present invention provides compounds in accordance with any of the above embodiments, or pharmaceutically acceptable salts thereof, wherein Z is absent, —NH—, —$NHSO_2$—, —$SO_2NH$—, —N═S(═O)$<(R^a)_2$ (wherein each $R^7$ is independently selected from the group consisting of H, methyl, or isopropyl), —S(═O)(═NH)—, —S—, —S(═O)—, —$SO_2$—, —(C═O)—, —(C═O)NH—, or —NH(C═O)—.

In embodiment 29, the present invention provides compounds in accordance with any of the above embodiments, or pharmaceutically acceptable salts thereof, wherein $R^8$ is selected from (a) H; (b) $C_{1-6}$alk substituted by 0, 1, 2 or 3 group(s) selected from F, Cl, Br, —OH, —$OCH_3$, or cyclopropyl; or (c) a saturated, partially-saturated or unsaturated 3-, 4-, 5-, 6-, or 7-membered monocyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —$C_{1-6}$alkOH, —OH, —$OCH_3$, —$NH_2$, or oxo.

In embodiment 30, the present invention provides compounds in accordance with any of the above embodiments, or pharmaceutically acceptable salts thereof, wherein $R^8$ is selected from cyclopropyl, cyclobutyl, cyclopentyl, oxetanyl, azetidinyl, tetrahydrofuranyl, or 1,3,4-oxathiazinanyl.

In embodiment 31, the present invention provides compounds in accordance with any of the above embodiments, or pharmaceutically acceptable salts thereof, wherein $R^3$ is H.

In embodiment 32, the present invention provides compounds in accordance with any of the above embodiments, or pharmaceutically acceptable salts thereof, wherein $R^4$ is selected from (a) H; (b) $C_{1-6}$alk substituted by 0, 1, 2 or 3 OH group(s); or (c) cyclopropyl.

In embodiment 33, the present invention provides compounds in accordance with any of the above embodiments, or pharmaceutically acceptable salts thereof, wherein $R^4$ is methyl.

In embodiment 34, the present invention provides compounds in accordance with any of the above embodiments, or pharmaceutically acceptable salts thereof, wherein $R^5$ is H.

In embodiment 35, the present invention provides compounds in accordance with any of the above embodiments, or pharmaceutically acceptable salts thereof, wherein $R^6$ is H or F.

In embodiment 36, the present invention provides compounds in accordance with any of the above embodiments, or pharmaceutically acceptable salts thereof, wherein $R^{3a}$ is H or F.

In embodiment 37, the present invention provides compounds in accordance with any of the above embodiments, or pharmaceutically acceptable salts thereof, wherein $R^{3b}$ is H.

In embodiment 38, the present invention provides compounds in accordance with any of the above embodiments, or pharmaceutically acceptable salts thereof, wherein $R^{3c}$ is H.

In embodiment 39, the present invention provides compounds in accordance with any of the above embodiments, or pharmaceutically acceptable salts thereof, wherein $R^{3d}$ is H.

In embodiment 40, the present invention provides compounds in accordance with any of the above embodiments, or pharmaceutically acceptable salts thereof, wherein $R^{3e}$ is H.

In embodiment 41, the present invention provides compounds in accordance with any of the above embodiments, or pharmaceutically acceptable salts thereof, wherein $R^{3f}$ is H.

In embodiment 42, the present invention provides a compound, or pharmaceutically acceptable salts thereof, selected from:

N-(4-((3-(4,4-Difluoropiperidin-1-yl)-5-methylphenyl)amino)-5-(6-azaspiro[2.5]octan-6-yl)quinazolin-7-yl)-2-hydroxyethane-1-sulfonamide;

N-(4-((3-(4,4-Difluoropiperidin-1-yl)-5-methylphenyl)amino)-2-methyl-5-(6-azaspiro[2.5]octan-6-yl)quinazolin-7-yl)-2-hydroxyethane-1-sulfonamide;

N-(3-(4,4-Difluoropiperidin-1-yl)-5-methylphenyl)-7-(methylsulfonyl)-5-(6-azaspiro[2.5]octan-6-yl)quinazolin-4-amine;

N-(3-(4,4-Difluoropiperidin-1-yl)-5-methylphenyl)-5-(6-azaspiro[2.5]octan-6-yl)quinazolin-4-amine;

(R)-Cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone;

(S)-Cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone;

2-Hydroxy-N-(4-((3-methyl-5-(3,3,3-trifluoropropoxy)phenyl)amino)-5-(6-azaspiro[2.5]octan-6-yl)quinazolin-7-yl)ethane-1-sulfonamide;

N-(4-((3,5-Dimethylphenyl)amino)-5-(6-azaspiro[2.5]octan-6-yl)quinazolin-7-yl)-2-hydroxyethane-1-sulfonamide;

N-(5-(6-Azaspiro[2.5]octan-6-yl)-4-((3-(3,3,3-trifluoropropoxy)phenyl)amino)quinazolin-7-yl)-2-hydroxyethane-1-sulfonamide;

N-(4-((2-(4,4-Difluoropiperidin-1-yl)-6-methylpyrimidin-4-yl)amino)-5-(6-azaspiro[2.5]octan-6-yl)quinazolin-7-yl)-2-hydroxyethane-1-sulfonamide;

N-(4-((2-(4,4-Difluoropiperidin-1-yl)-6-methylpyridin-4-yl)amino)-5-(6-azaspiro[2.5]octan-6-yl)quinazolin-7-yl)-2-hydroxyethane-1-sulfonamide;

N-(4-((6-(4,4-Difluoropiperidin-1-yl)-4-methylpyridin-2-yl)amino)-5-(6-azaspiro[2.5]octan-6-yl)quinazolin-7-yl)-2-hydroxyethane-1-sulfonamide;

N-(4-(3-(4,4-Difluoropiperidin-1-yl)-5-methylphenoxy)-5-(6-azaspiro[2.5]octan-6-yl)quinazolin-7-yl)-2-hydroxyethane-1-sulfonamide;

N-(1-((3-(4,4-Difluoropiperidin-1-yl)-5-methylphenyl)amino)-8-(6-azaspiro[2.5]octan-6-yl)phthalazin-6-yl)-2-hydroxyethane-1-sulfonamide;

(R)-2-Hydroxy-N-(4-((3-methyl-5-(2-methylmorpholino)phenyl)amino)-5-(6-azaspiro[2.5]octan-6-yl)quinazolin-7-yl)ethane-1-sulfonamide;

(R)-2-Hydroxy-N-(4-((4-methyl-6-(2-methylmorpholino)pyridin-2-yl)amino)-5-(6-azaspiro[2.5]octan-6-yl)quinazolin-7-yl)ethane-1-sulfonamide;

(R)-2-Hydroxy-N-(4-((6-methyl-2-(2-methylmorpholino)pyrimidin-4-yl)amino)-5-(6-azaspiro[2.5]octan-6-yl)quinazolin-7-yl)ethane-1-sulfonamide;

2-Hydroxy-N-(4-((2-((1-hydroxy-2-methylpropan-2-yl)amino)-6-methylpyrimidin-4-yl)amino)-5-(6-azaspiro[2.5]octan-6-yl)quinazolin-7-yl)ethane-1-sulfonamide;

N-(4-((2-Fluoro-3-((1-hydroxy-2-methylpropan-2-yl)amino)phenyl)amino)-5-(6-azaspiro[2.5]octan-6-yl)quinazolin-7-yl)-2-hydroxyethane-1-sulfonamide;

2-Hydroxy-N-(4-((3-(2-hydroxy-2-methylpropoxy)phenyl)amino)-5-(6-azaspiro[2.5]octan-6-yl)quinazolin-7-yl)ethane-1-sulfonamide;

4-((2-(4,4-Difluoropiperidin-1-yl)-6-methylpyrimidin-4-yl)amino)-N-(3-methyloxetan-3-yl)-5-(6-azaspiro[2.5]octan-6-yl)quinazoline-7-sulfonamide;

(S)—N-(4-((6-(4,4-Difluoropiperidin-1-yl)-4-methylpyridin-2-yl)amino)-5-(6-azaspiro[2.5]octan-6-yl)quinazolin-7-yl)-1-hydroxypropane-2-sulfonamide;

(R)—N-(4-((6-(4,4-Difluoropiperidin-1-yl)-4-methylpyridin-2-yl)amino)-5-(6-azaspiro[2.5]octan-6-yl)quinazolin-7-yl)-1-hydroxypropane-2-sulfonamide;

N-(4-((2-(3,3-Difluoroazetidin-1-yl)-6-methylpyrimidin-4-yl)amino)-5-(6-azaspiro[2.5]octan-6-yl)quinazolin-7-yl)-2-hydroxyethane-1-sulfonamide;

N-(4-((2-(4,4-Difluoropiperidin-1-yl)-6-methylpyrimidin-4-yl)amino)-8-fluoro-5-(6-azaspiro[2.5]octan-6-yl)quinazolin-7-yl)-2-hydroxyethane-1-sulfonamide;

N-(4-((2-(4,4-Difluoropiperidin-1-yl)-6-methylpyrimidin-4-yl)amino)-5-(6-azaspiro[2.5]octan-6-yl)pyrido[4,3-d]pyrimidin-7-yl)-2-hydroxyethane-1-sulfonamide;

N-(4-((2-(4,4-Difluoropiperidin-1-yl)-6-methylpyrimidin-4-yl)amino)-5-(7-azaspiro[3.5]nonan-7-yl)quinazolin-7-yl)-2-hydroxyethane-1-sulfonamide;

N-(4-((2-(4,4-Difluoropiperidin-1-yl)pyrimidin-4-yl)amino)-5-(4,4-dimethylazepan-1-yl)quinazolin-7-yl)-2-hydroxyethane-1-sulfonamide;

2-((4-((2-(4,4-Difluoropiperidin-1-yl)-6-methylpyrimidin-4-yl)amino)-5-(6-azaspiro[2.5]octan-6-yl)quinazolin-7-yl)sulfonyl)ethan-1-ol;

N-(4-((3-(4,4-Difluoropiperidin-1-yl)-5-methylphenyl)thio)-5-(6-azaspiro[2.5]octan-6-yl)quinazolin-7-yl)-2-hydroxyethane-1-sulfonamide;

7-(Azetidin-3-ylsulfonyl)-N-(2-(4,4-difluoropiperidin-1-yl)-6-methylpyrimidin-4-yl)-5-(6-azaspiro[2.5]octan-6-yl)quinazolin-4-amine;

N-(tert-Butyl)-3-((7-((2-hydroxyethyl)sulfonamido)-5-(6-azaspiro[2.5]octan-6-yl)quinazolin-4-yl)amino)benzenesulfonamide;

N-(4-((3-(Cyclopentylsulfonyl)-4-methylphenyl)amino)-5-(6-azaspiro[2.5]octan-6-yl)quinazolin-7-yl)-2-hydroxyethane-1-sulfonamide;

N-(tert-Butyl)-4-((6-(N-(tert-butyl)sulfamoyl)pyridin-2-yl)amino)-5-(6-azaspiro[2.5]octan-6-yl)quinazoline-7-sulfonamide;

N-(tert-Butyl)-4-(chroman-5-ylamino)-5-(6-azaspiro[2.5]octan-6-yl)quinazoline-7-sulfonamide;

N-(1-((6-(4,4-Difluoropiperidin-1-yl)-4-methylpyridin-2-yl)amino)-8-(6-azaspiro[2.5]octan-6-yl)phthalazin-6-yl)-2-hydroxyethane-1-sulfonamide;

N-(1-((6-(4,4-Difluoropiperidin-1-yl)-4-methylpyridin-2-yl)amino)-8-(6-azaspiro[2.5]octan-6-yl)isoquinolin-6-yl)-2-hydroxyethane-1-sulfonamide;

N-(1-((3-(4,4-Difluoropiperidin-1-yl)-5-methylphenyl)amino)-8-(6-azaspiro[2.5]octan-6-yl)isoquinolin-6-yl)-2-hydroxyethane-1-sulfonamide;

2-(4-((3-(4,4-Difluoropiperidin-1-yl)-5-methylphenyl)amino)-5-(6-azaspiro[2.5]octan-6-yl)quinazolin-7-yl)isothiazolidine 1,1-dioxide;

N-(4-((3-(3,3-Difluoro-6-azabicyclo[3.1.1]heptan-6-yl)-5-methylphenyl)amino)-5-(6-azaspiro[2.5]octan-6-yl)quinazolin-7-yl)-2-hydroxyethane-1-sulfonamide;

N-(4-((3-(6,6-Difluoro-3-azabicyclo[3.1.1]heptan-3-yl)-5-methylphenyl)amino)-5-(6-azaspiro[2.5]octan-6-yl)quinazolin-7-yl)-2-hydroxyethane-1-sulfonamide;

N-(4-((3-(4,4-Difluoropiperidin-1-yl)-4-methylphenyl)amino)-5-(6-azaspiro[2.5]octan-6-yl)quinazolin-7-yl)-2-hydroxyethane-1-sulfonamide;

4-((3-(4,4-Difluoropiperidin-1-yl)-5-methylphenyl)amino)-N-(2-hydroxyethyl)-5-(6-azaspiro[2.5]octan-6-yl)quinazoline-7-carboxamide;

2-((8-((3-(4,4-Difluoropiperidin-1-yl)-5-methylphenyl)amino)-1-(6-azaspiro[2.5]octan-6-yl)-2,7-naphthyridin-3-yl)amino)-2-methylpropan-1-ol;

2-((5-((3-(4,4-Difluoropiperidin-1-yl)-5-methylphenyl)amino)-4-(6-azaspiro[2.5]octan-6-yl)-1,6-naphthyridin-2-yl)amino)-2-methylpropan-1-ol;

2-((5-((3-(4,4-Difluoropiperidin-1-yl)-5-methylphenyl)amino)-4-(6-azaspiro[2.5]octan-6-yl)pyrido[4,3-d]pyrimidin-2-yl)amino)-2-methylpropan-1-ol;

2-(4-((3-(4,4-Difluoropiperidin-1-yl)-5-methylphenyl)amino)-5-(6-azaspiro[2.5]octan-6-yl)quinazolin-7-yl)propan-2-ol; or N-(3-(4,4-Difluoropiperidin-1-yl)-5-methylphenyl)-5-(6-azaspiro[2.5]octan-6-yl)pyrido[3,4-d]pyrimidin-4-amine.

In embodiment 43, the present invention provides a compound, or pharmaceutically acceptable salts thereof, selected from:

| Ex. # | Chemical Structure | Name |
|---|---|---|
| 100 | 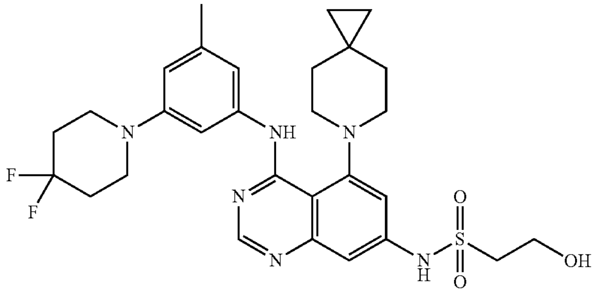 [SMILES: Cc1cc(Nc2ncnc3cc(NS(=O)(=O)CCO)cc(N4CCC5(CC4)CC5)c23)cc(N2CCC(F)(F)CC2)c1] | N-(4-((3-(4,4-Difluoropiperidin-1-yl)-5-methylphenyl)amino)-5-(6-azaspiro[2.5]octan-6-yl) quinazolin-7-yl)-2-hydroxy-ethane-1-sulfonamide |
| 100-1 | 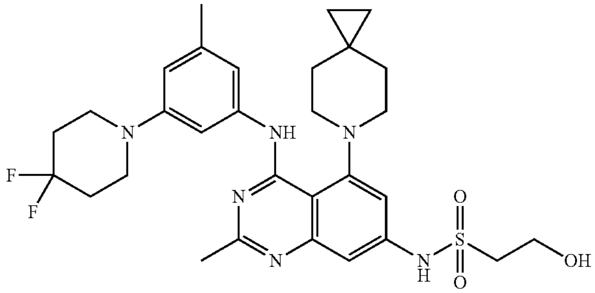 [SMILES: Cc1cc(Nc2nc(C)nc3cc(NS(=O)(=O)CCO)cc(N4CCC5(CC4)CC5)c23)cc(N2CCC(F)(F)CC2)c1] | N-(4-((3-(4,4-Difluoropiperidin-1-yl)-5-methylphenyl)amino)-2-methyl-5-(6-azaspiro[2.5]octan-6-yl)quinazolin-7-yl)-2-hydroxyethane-1-sulfonamide |
| 101 | 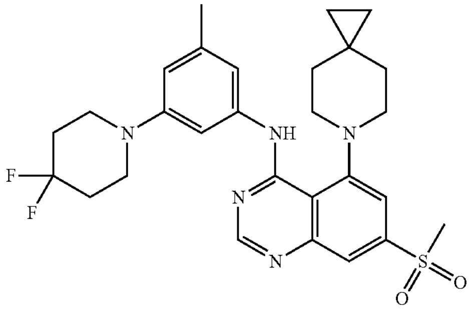 [SMILES: Cc1cc(Nc2ncnc3cc(S(C)(=O)=O)cc(N4CCC5(CC4)CC5)c23)cc(N2CCC(F)(F)CC2)c1] | N-(3-(4,4-Difluoropiperidin-1-yl)-5-methylphenyl)-7-(methylsulfonyl)-5-(6-azaspiro[2.5]octan-6-yl) quinazolin-4-amine |
| 101-1 | 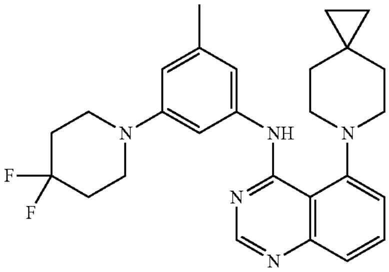 [SMILES: Cc1cc(Nc2ncnc3cccc(N4CCC5(CC4)CC5)c23)cc(N2CCC(F)(F)CC2)c1] | N-(3-(4,4-Difluoropiperidin-1-yl)-5-methylphenyl)-5-(6-azaspiro[2.5]octan-6-yl) quinazolin-4-amine |
| 102-1 | 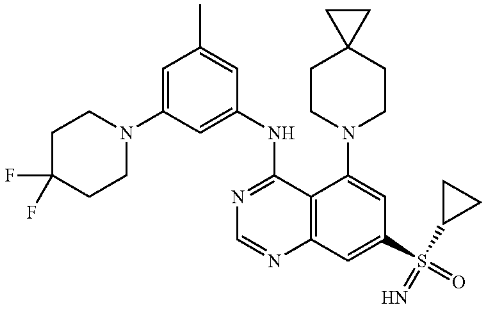 [SMILES: Cc1cc(Nc2ncnc3cc([S@](=N)(=O)C4CC4)cc(N4CCC5(CC4)CC5)c23)cc(N2CCC(F)(F)CC2)c1] | (R)-Cyclopropyl(4-((3-(4,4-difluoropiperidin-1-yl)-5-methylphenyl) amino)-5-(6-azaspiro[2.5] octan-6-yl)quinazolin-7-yl)(imino)-16-sulfanone |

-continued

| Ex. # | Chemical Structure | Name |
| --- | --- | --- |
| 102-2 | 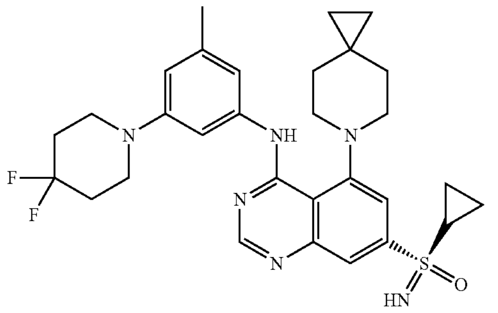 [SMILES: Cc1cc(Nc2ncnc3cc([S@@](=N)(=O)C4CC4)cc(N4CCC5(CC4)CC5)c23)cc(N2CCC(F)(F)CC2)c1] | (S)-Cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone |
| 103 | 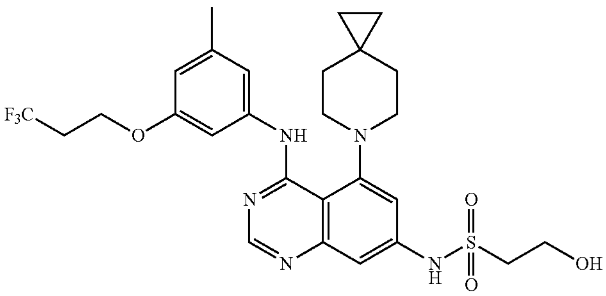 [SMILES: Cc1cc(Nc2ncnc3cc(NS(=O)(=O)CCO)cc(N4CCC5(CC4)CC5)c23)cc(OCCC(F)(F)F)c1] | 2-Hydroxy-N-(4-((3-methyl-5-(3,3,3-trifluoropropoxy)phenyl)amino)-5-(6-azaspiro[2.5]octan-6-yl)quinazolin-7-yl)ethane-1-sulfonamide |
| 103-1 | 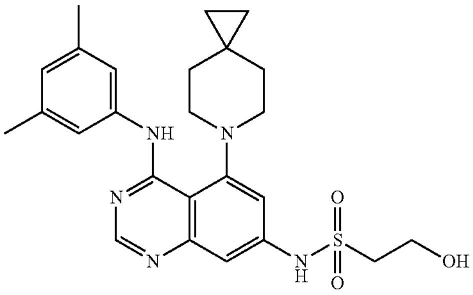 [SMILES: Cc1cc(C)cc(Nc2ncnc3cc(NS(=O)(=O)CCO)cc(N4CCC5(CC4)CC5)c23)c1] | N-(4-((3,5-Dimethylphenyl)amino)-5-(6-azaspiro[2.5]octan-6-yl)quinazolin-7-yl)-2-hydroxyethane-1-sulfonamide |
| 103-2 | 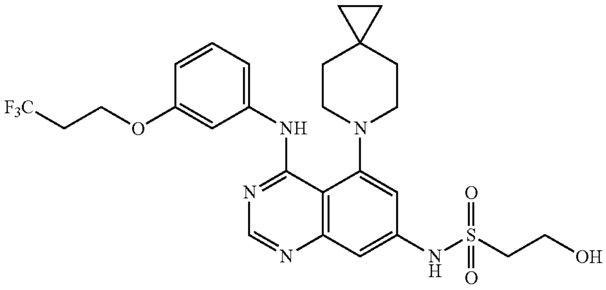 [SMILES: O=S(=O)(CCO)Nc1cc(N2CCC3(CC2)CC3)c2c(Nc3cccc(OCCC(F)(F)F)c3)ncnc2c1] | N-(5-(6-Azaspiro[2.5]octan-6-yl)-4-((3-(3,3,3-trifluoropropoxy)phenyl)amino)quinazolin-7-yl)-2-hydroxyethane-1-sulfonamide |
| 104 | 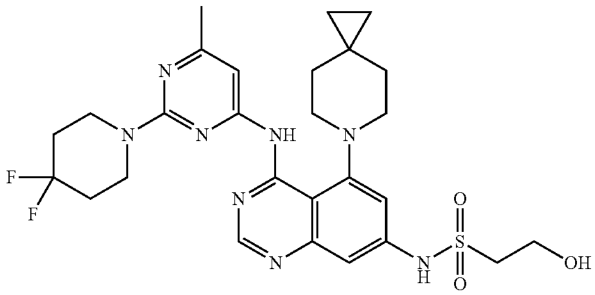 [SMILES: Cc1cc(Nc2ncnc3cc(NS(=O)(=O)CCO)cc(N4CCC5(CC4)CC5)c23)nc(N2CCC(F)(F)CC2)n1] | N-(4-((2-(4,4-Difluoropiperidin-1-yl)-6-methylpyrimidin-4-yl)amino)-5-(6-azaspiro[2.5]octan-6-yl)quinazolin-7-yl)-2-hydroxyethane-1-sulfonamide |

-continued

| Ex. # | Chemical Structure | Name |
|---|---|---|
| 105 | 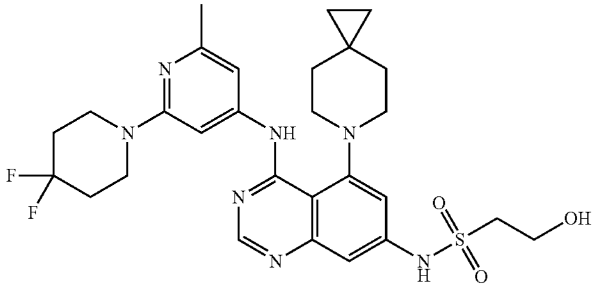 [SMILES: Cc1cc(Nc2ncnc3cc(NS(=O)(=O)CCO)cc(N4CCC5(CC4)CC5)c23)cc(N2CCC(F)(F)CC2)n1] | N-(4-((2-(4,4-Difluoropiperidin-1-yl)-6-methylpyridin-4-yl)amino)-5-(6-azaspiro[2.5]octan-6-yl)quinazolin-7-yl)-2-hydroxyethane-1-sulfonamide |
| 105-1 | 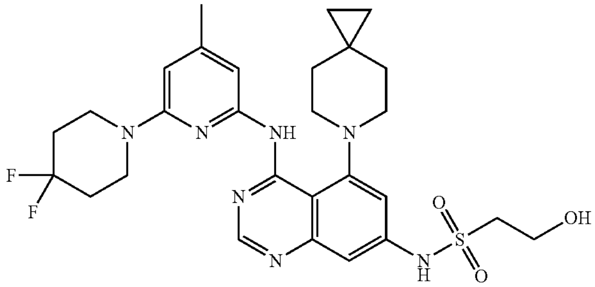 [SMILES: Cc1cc(Nc2ncnc3cc(NS(=O)(=O)CCO)cc(N4CCC5(CC4)CC5)c23)nc(N2CCC(F)(F)CC2)c1] | N-(4-((6-(4,4-Difluoropiperidin-1-yl)-4-methylpyridin-2-yl)amino)-5-(6-azaspiro[2.5]octan-6-yl)quinazolin-7-yl)-2-hydroxyethane-1-sulfonamide |
| 105-2 | 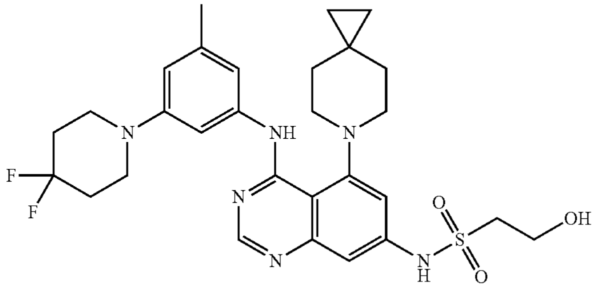 | N-(4-(3-(4,4-Difluoropiperidin-1-yl)-5-methylphenoxy)-5-(6-azaspiro[2.5]octan-6-yl)quinazolin-7-yl)-2-hydroxy-ethane-1-sulfonamide |
| 106 | 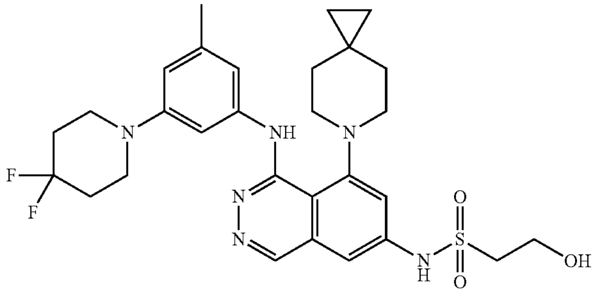 [SMILES: Cc1cc(Nc2nncc3cc(NS(=O)(=O)CCO)cc(N4CCC5(CC4)CC5)c23)cc(N2CCC(F)(F)CC2)c1] | N-(1-((3-(4,4-Difluoropiperidin-1-yl)-5-methylphenyl)amino)-8-(6-azaspiro[2.5]octan-6-yl)phthalazin-6-yl)-2-hydroxyethane-1-sulfonamide |

or any pharmaceutically-acceptable salt thereof.

Another aspect of the present invention is a pharmaceutical composition comprising anew class of compounds useful for modulating KIF18A protein alone or in a bound complex with microtubules or pharmaceutically acceptable salts thereof.

In embodiment 44, the present invention provides pharmaceutical compositions comprising a compound, or pharmaceutically acceptable salts thereof, in accordance with any one of embodiments 1-43, and a pharmaceutically acceptable diluent or carrier.

Yet another aspect of the present invention is a method of treating a condition that may be treated with KIF18a inhibitors, the method comprising administering to a patient in need thereof a therapeutically effective amount of a new class of compounds useful for modulating KIF18A protein alone or in a bound complex with microtubules or pharmaceutically acceptable salts thereof.

In embodiment 45, the present invention provides a method of treating a condition that may be treated with KIF18a inhibitors, the method comprising administering to a patient in need thereof a therapeutically effective amount of the compound in accordance with embodiments 1-43, or the composition according to embodiment 44.

In embodiment 46, the present invention provides the method of embodiment 45, wherein said condition is cancer selected from the group consisting of (a) a solid or hematologically derived tumor selected from cancer of the cancer of the bladder, endometrial, lung squamous cell, breast, colon, kidney, liver, lung, small cell lung cancer, esophagus, gall-bladder, brain, head and neck, ovary, pancreas, stomach, cervix, thyroid, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, or (f) a melanoma, seminoma, teratocarcinoma, osteosarcoma, xenoderoma pigmentosum, keratoctanthoma, thyroid follicular cancer or Kaposi's sarcoma.

In embodiment 46, the present invention provides the method of embodiment 45, wherein said condition is cancer selected from the group consisting of (a) a solid or hematologically derived tumor selected from cancer of the cancer of the bladder, endometrial, lung squamous cell, breast, colon, kidney, liver, lung, small cell lung cancer, esophagus, gall-bladder, brain, head and neck, ovary, pancreas, stomach, cervix, thyroid, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, or (f) a melanoma, seminoma, teratocarcinoma, osteosarcoma, xeroderma pigmentosum, keratoacanthoma, thyroid follicular cancer or Kaposi's sarcoma.

In embodiment 47, the present invention provides a method of reducing the size of a solid tumor in a subject, the method comprising administering to the subject in need thereof a therapeutically effective amount of the compound in accordance with embodiments 1-43, or the composition according to embodiment 44.

In embodiment 48, the present invention provides a method of treating a cell proliferation disorder in a subject, the method comprising administering to the subject in need thereof a therapeutically effective amount of the compound in accordance with embodiments 1-43, or the composition according to embodiment 44.

In embodiment 49, the present invention provides a method of inhibiting KIF18A in a cell, comprising contacting the cell with a compound, or pharmaceutically acceptable salts thereof, in accordance with embodiments 1-43, or the composition according to embodiment 44.

Yet another aspect of the present invention is a method of preparing a new class of compounds useful for modulating KIF18A protein alone or in a bound complex with microtubules or pharmaceutically acceptable salts thereof.

In embodiment 50, the invention provides a method of preparing a compound of Formula (I) as described herein.

In embodiment 51, the invention provides an intermediate compound used in the method of preparing a compound of Formula (I) as described herein.

DETAILED DESCRIPTION OF THE INVENTION

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^{2}H$ and $^{3}H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof.

Unless otherwise specified, the following definitions apply to terms found in the specification and claims:

"$C_{\alpha-\beta}$alk" means an alkyl group comprising a minimum of $\alpha$ and a maximum of $\beta$ carbon atoms in a branched or linear relationship or any combination of the three, wherein $\alpha$ and $\beta$ represent integers. The alkyl groups described in this section may also contain one or two double or triple bonds. A designation of $C_0$alk indicates a direct bond. Examples of $C_{1-6}$alkyl include, but are not limited to the following:

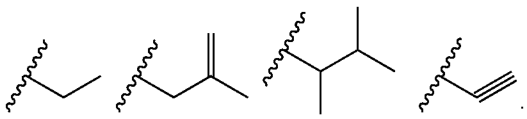

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atom selected from F, Cl, Br and I.

"$C_{\alpha\text{-}\beta}$haloalk" means an alk group, as described above, wherein any number—at least one—of the hydrogen atoms attached to the alk chain are replaced by F, Cl, Br or I.

The group $N(R^a)R^a$ and the like include substituents where the two $R^a$ groups together form a ring, optionally including a N, O or S atom, and include groups such as

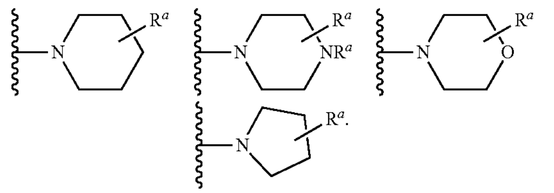

The group $N(C_{\alpha\text{-}\beta}alk)\ C_{\alpha\text{-}\beta}alk$, wherein α and β are as defined above, include substituents where the two $C_{\alpha\text{-}\beta}$alk groups together form a ring, optionally including a N, O or S atom, and include groups such as:

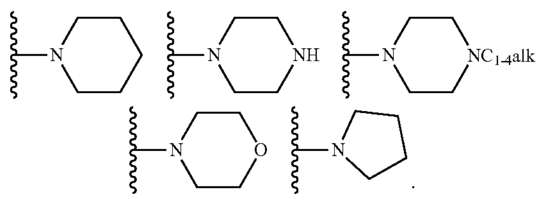

"Bicyclic ring" means a group that features two joined rings. A bicyclic ring can be carbocyclic (all of the ring atoms are carbons), or heterocyclic (the rings atoms consist, for example, 1, 2 or 3 heteroatoms, such as N, O, or S, in addition to carbon atoms). The two rings can both be aliphatic (e.g. decalin and norbornane), or can be aromatic (e.g. naphthalene), or a combination of aliphatic and aromatic (e.g. tetralin).

Bicyclic rings include:

(a) spirocyclic compounds, wherein the two rings share only one single atom, the spiro atom, which is usually a quaternary carbon. Examples of spirocyclic compound include, but are not limited to:

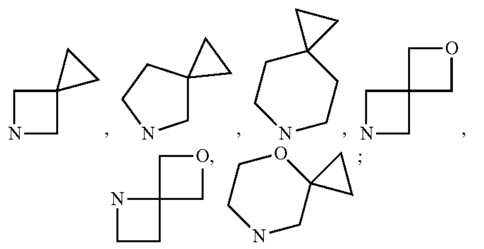

(b) fused bicyclic compounds, wherein two rings share two adjacent atoms. In other words, the rings share one covalent bond, i.e. the bridgehead atoms are directly connected (e.g. α-thujene and decalin). Examples of fused bicyclic rings include, but are not limited to:

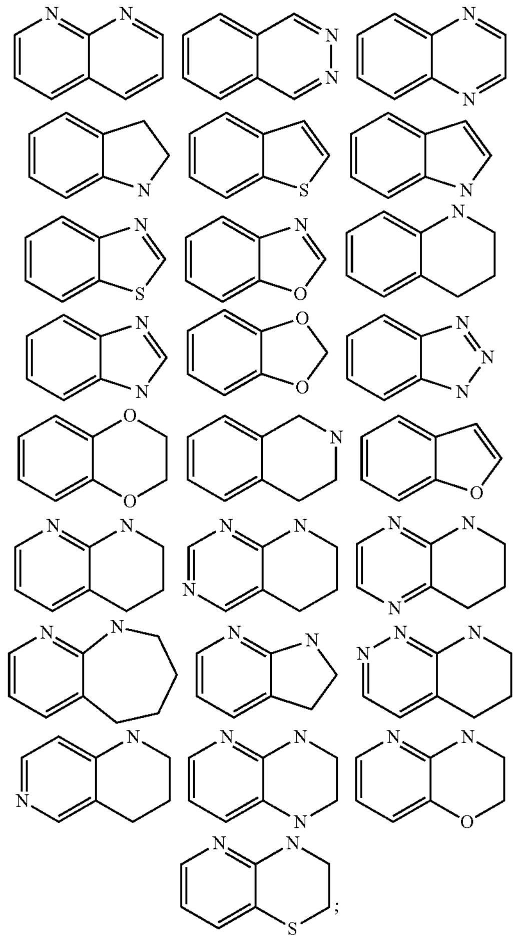

(c) bridged bicyclic compounds, wherein the two rings share three or more atoms, separating the two bridgehead atoms by a bridge containing at least one atom. For example, norbornane, also known as bicyclo[2.2.1]heptane, can be thought of as a pair of cyclopentane rings each sharing three of their five carbon atoms. Examples of bridged bicyclic rings include, but are not limited to:

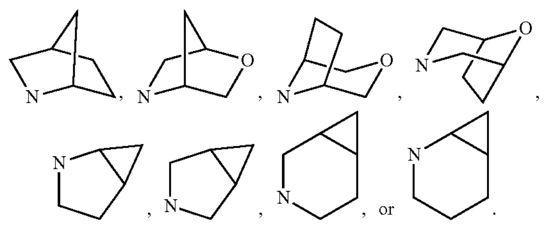

"Carbocycle" or "Carbocyclic" means a ring comprising by itself or in combination with other terms, represents, unless otherwise stated, cyclic version of "$C_{\alpha\text{-}\beta}$alk". Examples of carbocycle include cyclopentyl, cyclohexyl, 1-cyclohexenyl, 3-cyclohexenyl, cycloheptyl, cyclobutylene, cyclohexylene and the like.

"Heterocycle" or "Heterocyclic" means a ring comprising at least one carbon atom and at least one other atom selected from N, O and S. Examples of heterocycles that may be found in the claims include, but are not limited to, the following:

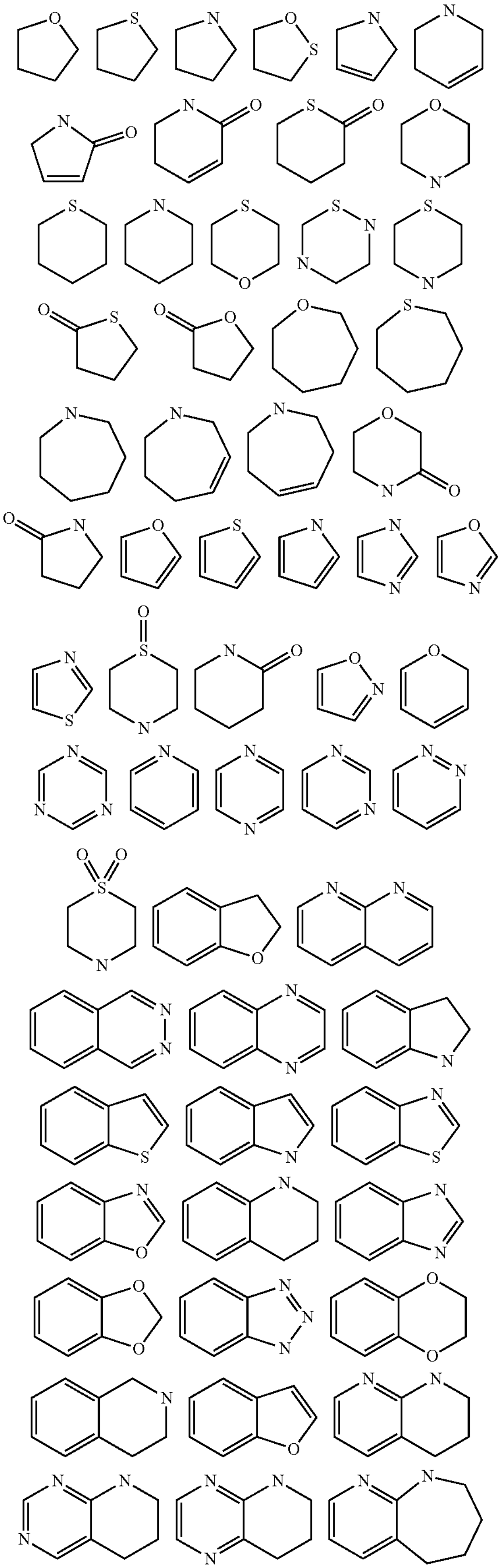

-continued

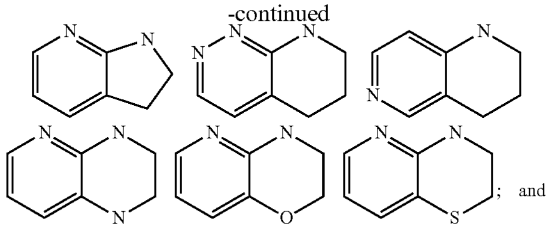

; and

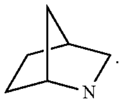

.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyldimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

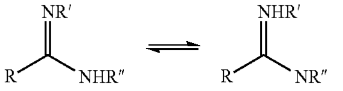

-continued

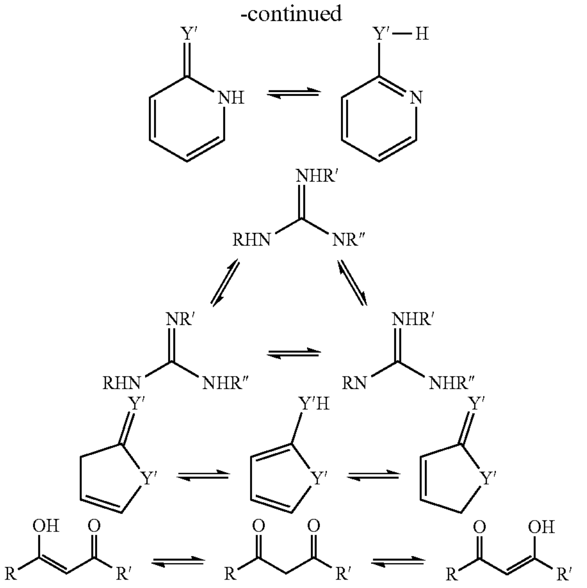

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, 4/11/81) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Pharmaceutical Compositions, Dosing, and Routes of Administration

Also provided herein are pharmaceutical compositions that includes a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pennsylvania, 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable e" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KIF18A-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A “therapeutically effective amount” means an amount effective to treat or to prevent development of, or to alleviate the existing symptoms of, the subject being treated. Determination of the effective amounts is well within the capability of those skilled in the art, especially in light of the detailed disclosure provided herein. Generally, a “therapeutically effective dose” refers to that amount of the compound that results in achieving the desired effect. For example, in one preferred embodiment, a therapeutically effective amount of a compound disclosed herein decreases KIF18A activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject’s age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. While individual needs vary, determination of optimal ranges of effective amounts of the compound is within the skill of the art. Such doses may be administered in a single dose or it may be divided into multiple doses.

The terms “cancer” and “cancerous” when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer, ovarian cancer, and endometrial cancer. While the term “cancer” as used herein is not limited to any one specific form of the disease, it is believed that the methods of the invention will be particularly effective for cancers which are found to be accompanied by unregulated levels of KIF18A or dependent on KIF18A for proper chromosome segregation and survival in the mammal.

The terms “treat”, “treating” and “treatment” as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term “patient”, “subject”, or “mammal” as used herein refers to any “patient”, “subject”, or “mammal” including humans, cows, horses, dogs and cats. In one embodiment of the invention, the mammal is a human.

The term “comprising” is meant to be open ended, including the indicated component(s) but not excluding other elements.

The terms “Formula I” include any sub formulas.

Methods of Using KIF18A Inhibitors

The present disclosure provides compounds having MT-based KIF18A modulatory activity in general, and inhibitory activity in particular. In one embodiment of the invention, there is provided a method of modulating KIF18A protein in a subject, the method comprising administering to the subject an effective dosage amount of a compound of Formulas I. As such, the compounds of the invention may be used to treat cellular proliferation disorders, including uncontrolled cell growth, aberrant cell cycle regulation, centrosome abnormalities (structural and or numeric, fragmentation). Other diseases or disorders associated with the accumulation of extra centrosomes (>2) include human papillomavirus (HPV) infection, including HPV-associated neoplasias. The compounds are also useful for cilia-related diseases as well as ablating haploid germ cell population which could be used as a male contraceptive.

In addition, compounds of the invention are useful for, but not limited to, the prevention or treatment of cancer and other KIF18A-mediated diseases or disorders. For example, compounds of the invention would be useful for the treatment of various solid and hematologically derived tumors, such as carcinomas, including, without limitation, cancer of the bladder, breast, colon, kidney, liver, lung (including squamous cell and small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin’s lymphoma, non-Hodgkin’s lymphoma, hairy cell lymphoma and Burkett’s lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

Based on the ability to modulate kinesin impacting angiogenesis, the compounds of the invention are also useful in treatment and therapy of proliferative diseases. Particularly, these compounds can be used for the treatment of an inflammatory disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer, such as with radiation therapy, small molecule targeted agents (e.g. PARP inhibitors, kinase inhibitors), therapeutic antibodies (e.g. naked and drug-conjugate) immunotherapy antibodies (checkpoint inhibitors, bi-specific T-cell engagers) with neoplastic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

There are large numbers of anticancer agents available in commercial use, in clinical evaluation and in pre-clinical development, which would be selected for treatment of neoplasia by combination drug chemotherapy. Such agents fall into several major categories such as antibiotic-type agents, alkylating and alkylating-like agents, antimitotic agents, targeted small molecule agents, antimetabolite agents, hormonal agents, immunological agents, anti-angiogenic agents, interferon-type agents and a category of miscellaneous agents.

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, targeted small molecule agents, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of antimitotic agents, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine;

nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel, Nab-paclitaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin, oxaliplatin, carboplatin; etoposide (VP-16); ifosfamide; mitomycin C; mitoxantrone; vinblastine vincristine; vinorelbine; navelbine; novantrone; teniposide; daunomycin; aminopterin; xeloda; ibandronate; topotecan; camptothecin-11 (CPT-11); topoisomerase inhibitor RFS 2000; difluoromethylornithine (DMFO), Where desired, the compounds or pharmaceutical composition of the present disclosure can be used in combination with commonly prescribed anti-cancer drugs such as Herceptin®, Avastin®, Erbitux®, Rituxan®, Taxol®, Abraxane, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Talazoparib, Niraparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl) amine, Troxacitabine, Uramustine, Vadimezan, Vinflunine, ZD6126 or Zosuquidar, CDK4/6 inhibitors (Palbociclib, Ibrance; Ribociclib, Kisqali; Abemaciclib, Verzenio).

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931 788, WO 90/05719, WO 99/52910, WO 99/52889, WO 99/29667, WO1999007675, European Patent Publication EP1786785, European Patent Publication No. EP1181017, United States Publication No. US20090012085, United States Publication U.S. Pat. No. 5,863,949, United States Publication U.S. Pat. No. 5,861,510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof Δn agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728, 813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (plNN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (plNN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237, AMG 900, AZD-1152), cell surface monoclonal antibodies (e.g., anti-CD38 (HUMAX-CD38), anti-CS1 (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torcl/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib, Talazoparib, Niraparib veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds or pharmaceutical compositions of the disclosure can also be used in combination with an amount of one or more substances selected from EGFR inhibitors, MEK inhibitors, PI3K inhibitors, AKT inhibitors, TOR inhibitors, and immune therapies, including anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., Pharmacogenetics and Pharmacogenomics In Oncology Therapeutic Antibody Development, BioTechniques 2005; 39(4): 565-8, and Paez J G, et. al., EGFR Mutations In Lung Cancer Correlation With Clinical Response To Gefitinib Therapy, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published Jan. 23, 1997; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12):1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Akt1) (Barnett et al. (2005) Biochem. J., 385 (Pt. 2), 399-408); Akt-1-1,2 (inhibits Ak1 and 2) (Barnett et al. (2005) Biochem. J. 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine (e.g., interferes with Akt membrane localization; Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); and triciribine (TCN or API-2 or NCI identifier: NSC 154020; Yang et al. (2004) Cancer Res. 64, 4394-9).

TOR inhibitors include, but are not limited to, inhibitors include AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

Immune therapies include, but are not limited to, anti-PD-1 agents, anti-PDL-1 agents, anti-CTLA-4 agents, anti-LAG1 agents, and anti-OX40 agents. Exemplary anti-PD-1 antibodies and methods for their use are described by Goldberg et al., Blood 110(1):186-192 (2007), Thompson et al., Clin. Cancer Res. 13(6):1757-1761 (2007), and Korman et al., International Application No. PCT/JP2006/309606 (publication no. WO 2006/121168 A1), each of which are expressly incorporated by reference herein. include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

GITR agonists include, but are not limited to, GITR fusion proteins and anti-GITR antibodies (e.g., bivalent anti-GITR antibodies), such as, a GITR fusion protein described in U.S. Pat. No. 6,111,090 box.c, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

EXPERIMENTAL

Abbreviations: The following abbreviations may be used herein:

AcOH acetic acid
$Ac_2O$ acetic anhydride
aq or aq. Aqueous
BINAP (2,2'-bis(diphenylphosphino)-1,1'-binaphthyl
DCM Dichloromethane
DEAD diethyl azodicarboxylate
DMAP 4-dimethylaminopyridine
DMF N,N-dimethylformamide
DMSO dimethyl sulfoxide
Dppf, DPPF or dppf 1,1'-bis(diphenylphosphino)ferrocene
ESI or ES electrospray ionization
Et Ethyl
$Et_2O$ diethyl ether
EtOH ethyl alcohol
EtOAc EtOAc
G Grams
H Hour
HPLC high pressure liquid chromatography
IPA isopropyl alcohol
iPr Isopropyl
$iPr_2NEt$ or DIPEA N-ethyl diisopropylamine (Hünig's base)
LAH lithium aluminium hydride
LC MS, LCMS, LC-MS or LC/MS liquid chromatography mass spectroscopy
LG leaving group (e.g., halogen, mesylate, triflate)
m/z mass divided by charge
Me Methyl
MeCN/CAN Acetonitrile
MeOH Methanol
Met metal species for cross-coupling (e.g., MgX, ZnX, $SnR_3$, $SiR_3$, $B(OR)_2$)
Mg Milligrams
Min Minutes
mL Milliliters
MS mass spectra
NMP 1-methyl-2-pyrrolidine
n-BuLi n-butyllithium
NMR nuclear magnetic resonance $Pd_2(dba)_3$ tris(dibenzylideneacetone)dipalladium(0)
$Pd(dppf)Cl_2$-DCM [1,1'-bis(diphenylphosphino)ferrocene] dichloropalladium(II),
complex with dichloromethane
$Pd(PPh_3)_4$ tetrakis(triphenylphosphine)palladium(0)
$Ph_3P$ Triphenylphosphine
PMB-$NH_2$ 4-methoxybenzylamine
Phen 1,10-phenanthroline
PR or PG or Prot. group protecting group
rbf round-bottom flask
RP-HPLC reverse phase high pressure liquid chromatography
RT or rt room temperature
sat. or satd. Saturated
SFC supercritical fluid chromatography
TBAB tetrabutylammonium bromide
TEA or $Et_3N$ Trimethylamine
TFA trifluoroacetic acid
THF Tetrahydrofuran
Xantphos 4,5-bis(diphenylphosphino)-9,9-dimethylxanthene Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. Mass spectral data was determined by electrospray ionization technique. All examples were purified to >9000 purity as determined by high-performance liquid chromatography. Unless otherwise stated, reactions were run at room temperature.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 μm, 5 to 100% $CH_3CN$ in $H_2O$ with 0.1% TFA for 15 min at 1.5 mL/min; System B: Zorbax SB-C8, 4.6×75 mm, 10 to 90% $CH_3CN$ in $H_2O$ with 0.1% formic acid for 12 min at 1.0 mL/min) (Agilent Technologies, Santa Clara, CA). Silica gel chromatography was generally performed with prepacked silica gel cartridges (Biotage, Uppsala, Sweden or Teledyne-Isco, Lincoln, NE). $^1H$ NMR spectra were recorded on a Bruker AV-400 (400 MHz) spectrometer (Bruker Corporation, Madison, WI) or a Varian (Agilent Technologies, Santa Clara, CA) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, CA) LC/MS with UV detection at 254 nm and 215 nm and a low resonance electrospray mode (ESI).

General Synthetic Scheme

Unless otherwise stated, starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

For the purpose of clarity in this general synthesis section, Compounds of Formula (I) as defined in the summary of the inventions can be schematically drawn to contain Ring $Ar^1$ and $Ar^2$ as follows:

(I)

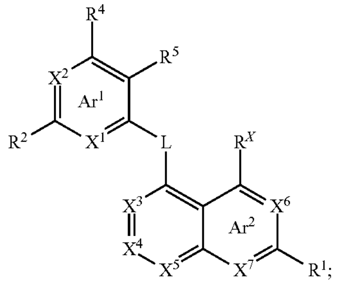

wherein the group L is $—NR^3$, —O—, —S—, S=O, or $S(=O)_2$; $X^1$ is N or $—CR^6$, $X^2$ is N or $—CR^{3a}$, $X^3$ is N or —$CR^{3a}$, $X^4$ is N or —$CR^{3c}$, $X^5$ is N or —$CR^{3d}$, $X^6$ is N or —$CR^{3e}$ and $X^7$ is N or —$CR^{3f}$; Ring $Ar^1$ is located to the left of the linker, and ring $Ar^2$ is located to the right of linker, fused to the ring containing the groups $X^3$; $X^4$; and $X^5$.

Generally, compounds of Formula (I), can be synthesized via three general steps as follows:

Step 1: Preparation of Ring $Ar^1$ compound.

Step 2: Preparation of Ring $Ar^2$ compound.

Step 3: Combination of Ring $Ar^1$ compound to Ring $Ar^2$ compound.

The generic Schemes A-C below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

In one embodiment, Schemes A-B below provide generic preparation of a compound of Formula (I); having the following formula:

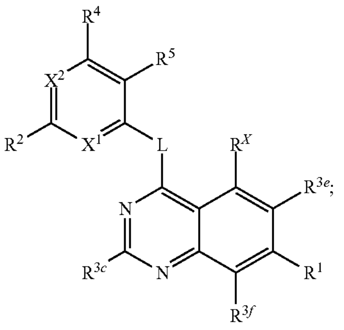

which embodies compounds of formulae (Ia), (Ib), (Ic), and (Id) as described herein:

(Ia)

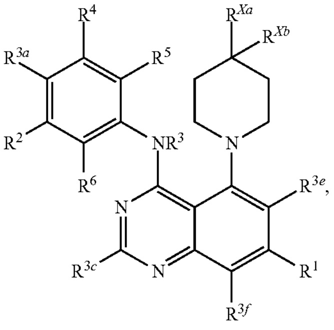

(Ib)

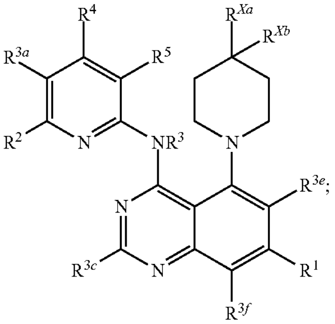

-continued (Ic)

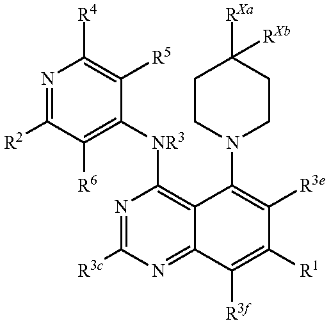

; and (Id)

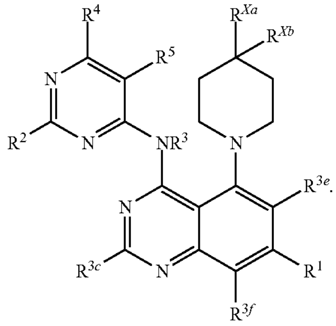

Scheme A: Preparation of Compounds (Ia), (Ib), (Ic), and (Id):

According to Scheme A, in one embodiment, a compound of Formulae (Ia), (Ib), (Ic), and (Id) as disclosed herein can be synthesized as follows:

Step A-1-a: Preparation of Ring $Ar^1$ Compounds Wherein $X^1$ is N or —$CR^6$ and $X^2$ is N or —$CR^{3a}$

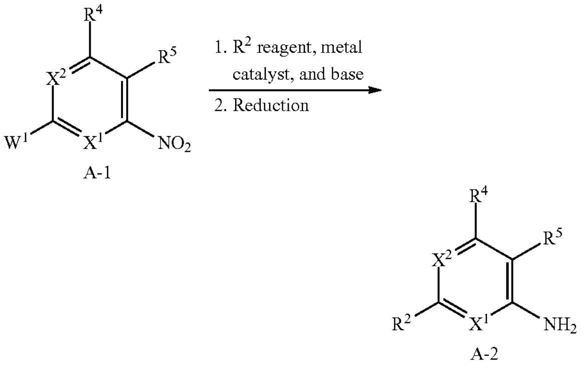

Compound A-1, wherein $W^1$ is a halogen, for example fluoro, chloro, bromo can be reacted with an $R^2$ group containing agent via metal catalyzed amination, where a suitable palladium or copper catalyst and a base are used, in the presence of a suitable base, in a suitable organic solvent such as NMP, dioxane, acetonitrile, tetrahydrofuran, DMF, toluene, and the like. Compound A-1 is commercially available or can be synthesized by known methods by those skilled in the art. Examples of compound A-1 include, but are not limited to, 1-bromo-3-methyl-5-nitrobenzene or 1-bromo-5-nitrobenzene. Examples of $R^2$ reagents include, but not limited to (1) (R)-2-methylmorpholine, (2) 4,4- difluoropiperidine hydrochloride, (3) 3,3-difluoroazetidine hydrochloride, (4) 3,3,3-trifluoropropan-1-ol, (5) 2-aminoethan-1-ol, or (6) 2-amino 3-methylpropan-1-ol. Examples of bases include, but are not limited to diisopropylethyl amine, potassium carbonate, or sodium tert-butoxide. This step is followed by a reduction with a suitable palladium catalyst and a hydrogen source, such as Pd/C in the presence of hydrogen gas, or reduction in the presence of iron to form compound A-2.

Step A-1-b: Preparation of Ring $Ar^1$ Compound Wherein $X^1$ is N or —$CR^6$ and $X^2$ is N

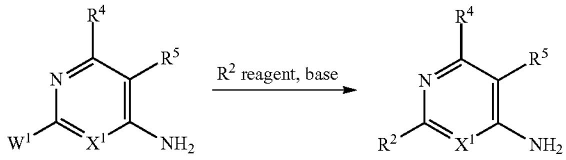

A-3 A-4

Compound A-3, wherein $W^1$ is a halogen, for example fluoro, chloro, bromo can be reacted with an $R^2$ group containing agent in the presence of a suitable base, in a suitable organic solvent such as NMP, dioxane, acetonitrile, tetrahydrofuran, DMF, and the like to form compound A-4. Compound A-3 is commercially available or can be synthesized by known methods by those skilled in the art. Examples of compound A-3 include, but are not limited to, 6-fluoropyridin-2-amine, 2-chloro-6-methylpyrimidin-4-amine or 2-chloro-6-methylpyridin-4-amine. Examples of $R^2$ reagents include, but not limited to (1) (R)-2-methylmorpholine, (2) 4,4-difluoropiperidine hydrochloride, (3) 3,3-difluoroazetidine hydrochloride, (4) 3,3,3-trifluoropropan-1-ol, (5) 2-aminoethan-1-ol, (6) 2-amino3-methylpropan-1-ol, or (7) 3,3,3-trifluoropropan-1-ol. Examples of bases include, but are not limited to diisopropylethyl amine, potassium carbonate, or sodium hydride.

Step A-1-c: Preparation of Ring $Ar^1$ Compound Wherein $X^1$ is —$CR^6$ and $X^2$ is N or —$CR^{3a}$

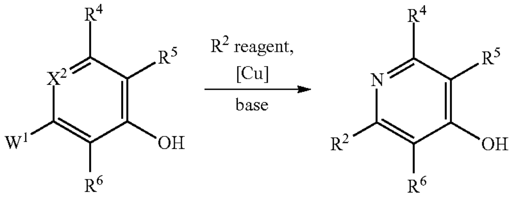

A-5 A-6

Alternatively, compound A-5, wherein $W^1$ is a halogen, for example chloro, bromo, or iodo can be reacted with an $R^2$ group having a formula of $R^{13}$—NH containing agent via metal catalyzed amination, where a suitable palladium or copper catalyst and a base are used, in the presence of a suitable base, in a suitable organic solvent such as NMP, dioxane, acetonitrile, tetrahydrofuran, DMF, DMSO, and the like to form compound A-6. Compound A-5 is commercially available or can be synthesized by known methods by those skilled in the art. Examples of compound A-5 include, but are not limited to, 3-bromo-5-methylphenol, 3-bromophenol, 3-bromo-4-methylphenol Examples of $R^2$ reagents include, but is not limited to (1) (R)-2-methylmorpholine, (2) 4,4-difluoropiperidine hydrochloride, (3) 3,3-difluoroazetidine hydrochloride, (4) 3,3,3-trifluoropropan-1-ol, (5) 2-aminoethan-1-ol, or (6) 2-amino3-methylpropan-1-ol.

Examples of bases include, but are not limited to diisopropylethyl amine, potassium carbonate, cesium carbonate, or sodium tert-butoxide.

Step A-2: Preparation of $Ar^2$ Compound

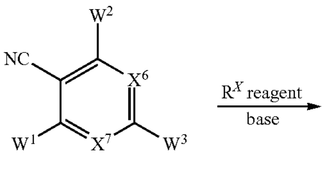

A-7

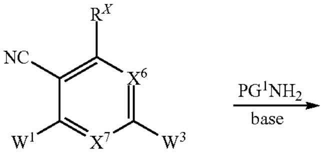

A-8

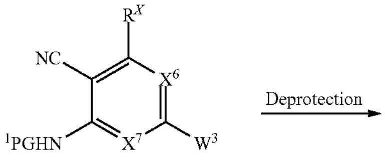

A-9

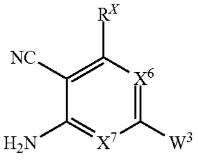

A-10

In Step A-2, Compound A-7, wherein each of $W^1$, $W^2$, and $W^3$ is independently a halogen, for example fluoro, chloro, bromo, or iodo, can be reacted with an $R^X$ reagent, such as (1) 6-azaspiro[2.5]octane hydrochloride, (2) 4,4-dimethylpiperidine hydrochloride, (3) 3,4,4-trimethylpiperidine hydrochloride, (4) 4-methyl-6-azaspiro[2.5]octane hydrochloride, or (5) 7-azaspiro[3.5]nonane hydrochloride, in a suitable organic solvent such as NMP, acetonitrile, tetrahydrofuran, DMF, methylene chloride, DMSO, and the like, to form Compound A-8, which is then treated with a protected amine compound, such as PMB protected amine compound, in the presence of a base, such as diisopropylethyl amine or triethyl amine, in a suitable organic solvent to give compound A-9. Compound A-9 is then reacted with a deprotecting agent, such as trifluoroacetic acid, to give compound A-10.

Step A-3-a: Coupling of Ring $Ar^1$ Compound to Ring $Ar^2$ Compound Followed by Introduction of $R^1$ to Form Compounds (Ia) or (Ib)

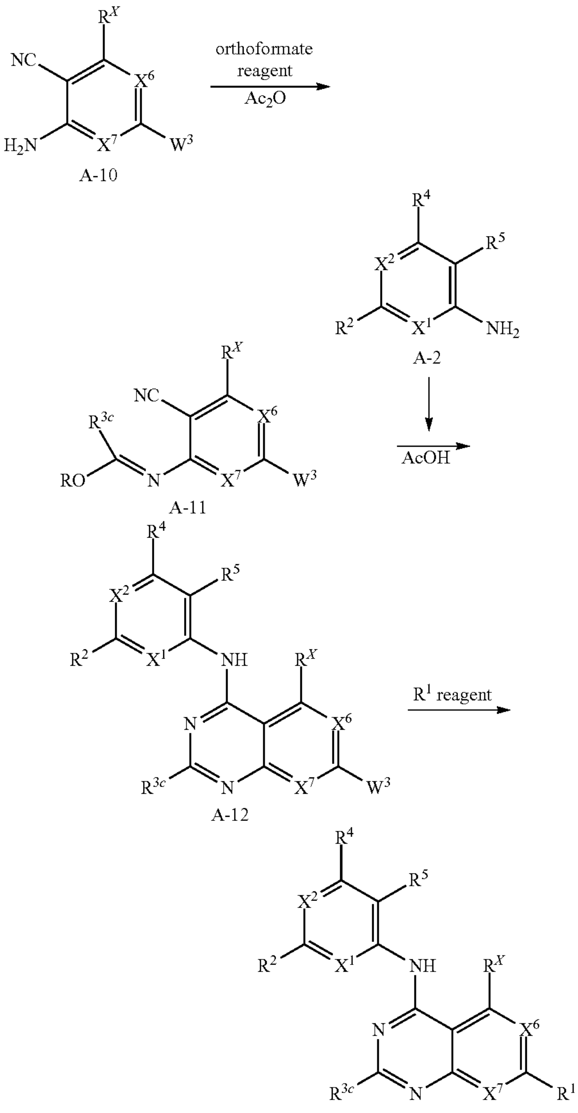

A-10
A-2
A-11
A-12
(Ia) or (Ib)

In Step A-3, compound A-10, which was obtained from Step A-2, can be reacted with an orthoformate reagent having formula $CR^{3c}(OR)_3$, wherein $R^{3c}$ is H or methyl, such as triethyl orthoformate in acetic anhydride to form compound A-11, which can be reacted with compound A-2 in the presence of acetic acid to form compound A-12. Those ordinary skilled synthetic chemists will readily understand that other cyclization agents can be used. Further manipulation of halogen group $W^3$ by transformation reactions such as, metal-catalyzed sulfoamidation, sulfination, or sulfonylation, in a suitable organic solvent such as DMSO, acetonitrile, tetrahydrofuran, DMF, methylene chloride, and the like, in the presence of a metal catalyst and an $R^1$ reagent, such as (1) 1-methylcyclopropane-1-sulfonamide, (2) 3-methyloxetan-3-amine, (3) tert-butyl 3-mercaptoazetidine-1-carboxylate, (4) ethyl 2-sulfamoylpropanoate, (5) 2-hydroxypropane-1-sulfonamide, (6) 2-hydroxyethane-1-sulfonamide, (7) ethyl iodoacetate, (8) 2-mercaptopropan-1-ol, (9) 2-mercapto-2-methylpropan-1-ol, (10) 2-aminoethan-1-ol, or (11) cyclopropanethiol can be used to form Compound (Ia) or (Ic). Those ordinary skilled in the art will readily understand that coupling reaction such as shown in Step A-3-a can be performed under various known conditions.

Step A-3-b: Coupling of Ring $Ar^1$ Compound to Ring $Ar^2$ Compound Followed by Introduction of $R^1$ to Form Compounds (Ic) or (Id)

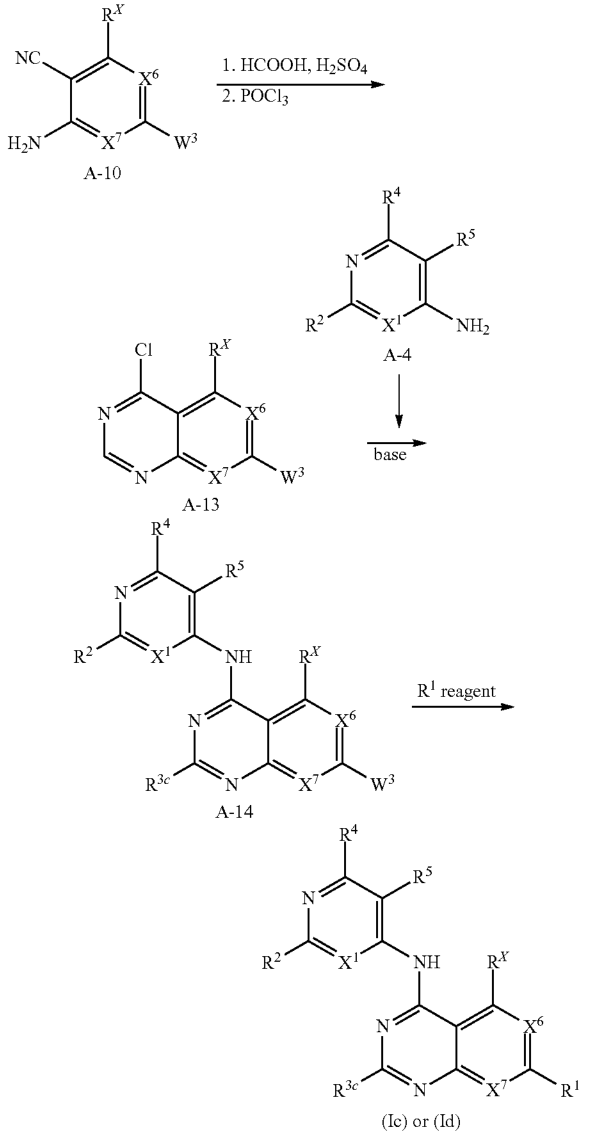

A-10
A-4
A-13
A-14
(Ic) or (Id)

Alternatively, Compound A-10 can be treated with formic acid at high temperature, ranging from 100° C. to 120° C., followed by chlorination reaction with a chlorinating agent, such as $POCl_3$, in organic solvent, such as toluene to form compound A-14, wherein $R^{3c}$ is H. Compound A-14 can then be treated with compound A-4 according to a similar procedure as described above in Step A-3-a to give Compound (Ic) or (Id).

Scheme B: Preparation of Compound (Ie):

In another embodiment, Scheme B provides generic preparation of a compound of Formula (I): having the following formula:

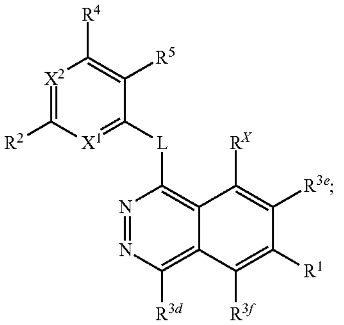

which embodies compounds of formulae (Ie) as described herein:

(Ie)

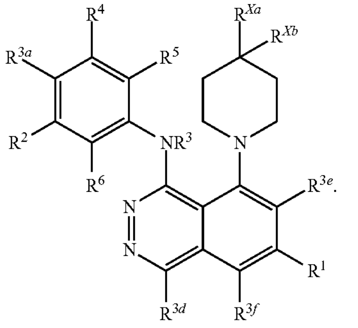

Step B-1: Preparation of Ring $Ar^1$ Compound

Ring $Ar^1$ compound of Compound (Ie) can be prepared according to the process described in Steps A-1-a to A-1-c of SCHEME A above.

Step B-2: Preparation of Ring $Ar^2$ Compound

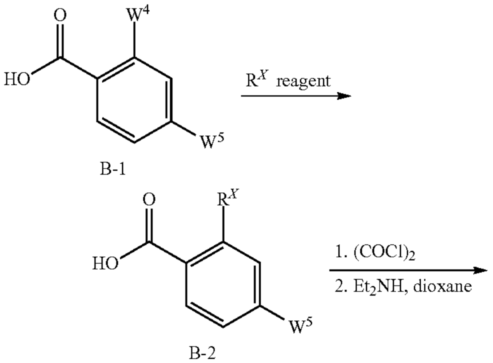

B-1

B-2

-continued

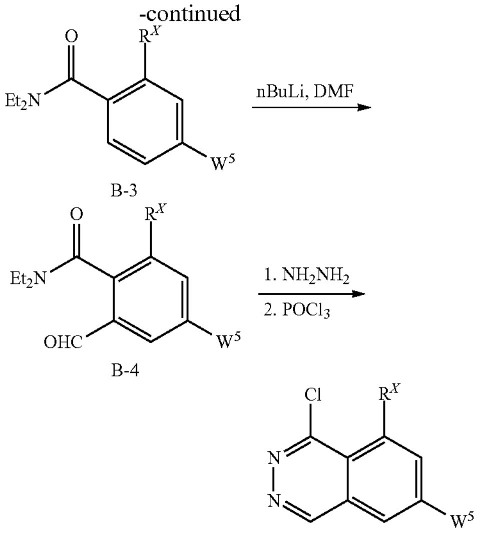

B-3

B-4

B-5

In Step B-2, Compound B-1, wherein each of $W^4$ and $W^5$ is independently halo, for example fluoro, chloro, bromo, or iodo, can be reacted with an $R^X$ reagent, such as (1) 6-azaspiro[2.5]octane hydrochloride, (2) 4,4-dimethylpiperidine hydrochloride, (3) 3,4,4-trimethylpiperidine hydrochloride, (4) 4-methyl-6-azaspiro[2.5]octane hydrochloride, or (5) 7-azaspiro[3.5]nonane hydrochloride, in a suitable organic solvent such as NMP, acetonitrile, tetrahydrofuran, DMF, methylene chloride, DMSO, and the like, to form Compound B-2, which is then treated with oxalyl chloride followed by diethyl amine to form the diethyl amide derivative B-3. Compound B-3 is then treated with nBuLi and DMF the aromatic aldehyde derivative B-4, which is then reacted with a cyclization agent, such as hydrazine, followed by chlorination with $POCl_3$ to give compound B-5.

Step B-3: Coupling of Ring $Ar^1$ Compound to Ring $Ar^2$ Compound Followed by Introduction of $R^1$ to Form Compounds (Ie)

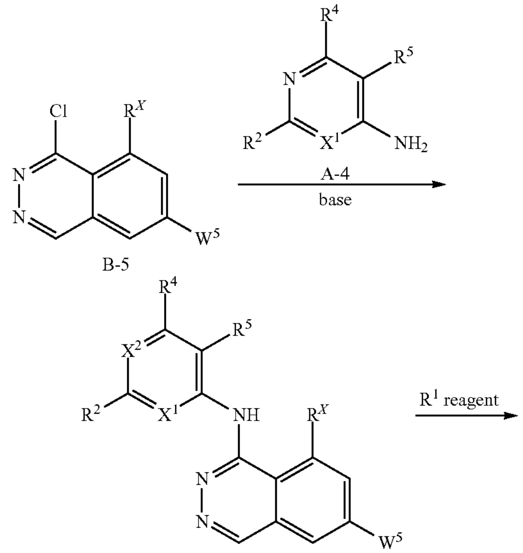

B-5

B-6

-continued

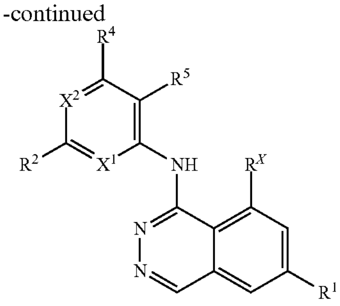

(Ie)

In step B-3 compound B-5 can be treated with compound A-4 according to analogous procedure and condition as described above in Step A-3-a to give Compound (Ie).

Preparation of Synthetic Intermediates

Preparation of Ring $Ar^1$ Intermediates

Intermediate 1: 3-(4,4-Difluoropiperidin-1-yl)-5-methylaniline

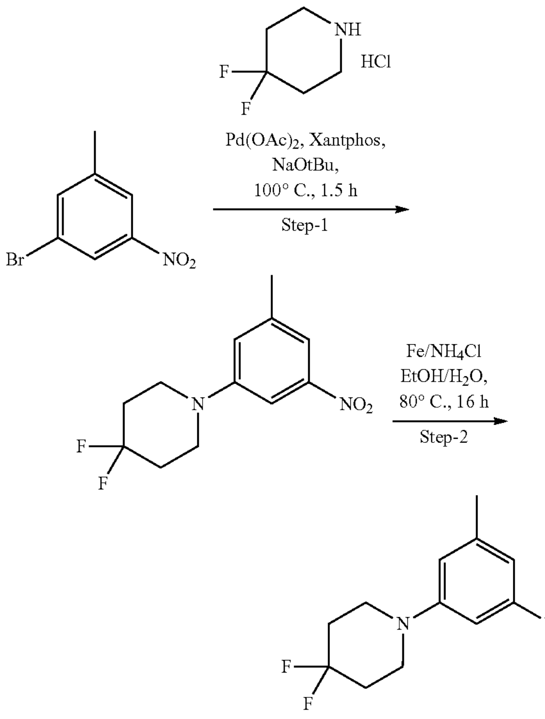

Intermediate 1

Step 1: To a solution of 1-bromo-3-methyl-5-nitrobenzene (10 g, 46.3 mmol) and 4,4-difluoropiperidine hydrochloride (10.9 g, 69.4 mmol) in toluene (50 mL), was added sodium tert-butoxide (13.3 g, 139 mmol), $Pd_2(dba)_3$ (4.24 g, 4.63 mmol) and xantphos (2.68 g, 4.63 mmol). The reaction mixture was heated at 100° C. for 1.5 h and allowed to cool to room temperature. The reaction mixture was diluted with water, passed through a bed of CELITE®, and washed with EtOAc. The organic extracts were washed with brine, dried over $Na_2SO_4$, filtered, and concentrated in vacuo. The crude product was purified by flash column chromatography eluting with 10% to 20% EtOAc in petroleum ether to provide 4,4-difluoro-1-(3-methyl-5-nitrophenyl)piperidine (2.3 g, 9.0 mmol, 19% yield) as a grey solid. $^1H$ NMR (400 MHz, DMSO-$d_6$): δ ppm 7.55 (t, J=2.3 Hz, 1H), 7.45 (s, 1H), 7.32 (d, J=2.3 Hz, 1H), 3.46 (t, J=5.8 Hz, 4H), 2.38 (s, 3H), 2.05 (tt, J=14.1, 5.8 Hz, 4H).

Step 2: To a solution of 4,4-difluoro-1-(3-methyl-5-nitrophenyl)piperidine (2.3 g, 9.0 mmol) in EtOH (23 mL) and water (4.6 mL) were added iron powder (5.01 g, 90 mmol) and ammonium chloride (4.80 g, 90 mmol) at rt and then heated at 80° C. for 16 h. The reaction mixture was cooled to rt, filtered through a CELITE® pad, and washed with MeOH. The filtrate was evaporated to dryness and purified by flash column chromatography eluting with 30% to 40% EtOAc in petroleum ether to provide 3-(4,4-difluoropiperidin-1-yl)-5-methylaniline (1.8 g, 8.0 mmol, 89% yield) as a brown solid. $^1H$ NMR (400 MHz, DMSO-$d_6$): δ ppm 6.00 (d, J=1.7 Hz, 2H), 5.89 (q, J=1.4 Hz, 1H), 4.81 (s, 2H), 3.20 (d, J=11.5 Hz, 4H), 2.09 (s, 3H), 1.94-2.04 (m, 4H). m/z (ESI): 227.2 $(M+H)^+$.

Intermediate 2: 3-Methyl-5-(3,3,3-trifluoropropoxy)aniline

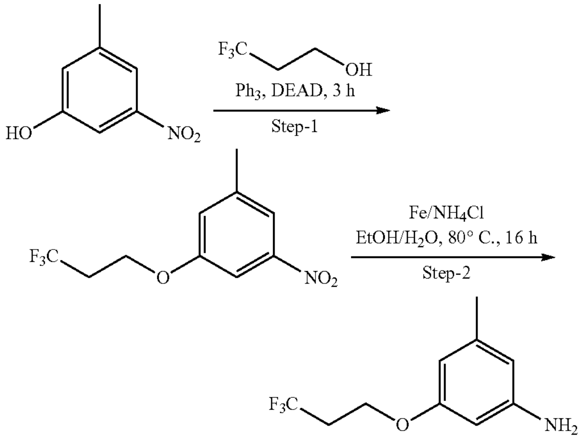

Intermediate 2

Step 1: To a solution of 3-methyl-5-nitrophenol (2.0 g, 13.1 mmol) and 3,3,3-trifluoropropan-1-ol (6.0 g, 52.2 mmol) in THF (30 mL) was added $PPh_3$ (13.70 g, 52.2 mmol) followed by diethyl (E)-diazene-1,2-dicarboxylate (8.27 mL, 52.2 mmol) at 0° C. The reaction mixture was stirred at rt for 3 h before it was diluted with water and extracted with EtOAc. The organic extracts were washed with brine, dried over $Na_2SO_4$, filtered, and concentrated in vacuo to give the crude material as an orange oil. Purification by flash column chromatography eluting with a gradient of 0% to 20% EtOAc in petroleum ether provided 1-methyl-3-nitro-5-(3,3,3-trifluoropropoxy)benzene (2.3 g, 8.8 mmol, 67% yield) as yellow oil. $^1H$ NMR (400 MHz, DMSO-$d_6$) δ ppm 7.63-7.66 (m, 1H), 7.51 (t, J=2.4 Hz, 1H), 7.24 (dt, J=2.4, 0.9 Hz, 1H), 4.29 (t, J=5.8 Hz, 2H), 2.79 (m, 2H), 2.37-2.41 (s, 3H).

Step 2: To a solution of 1-methyl-3-nitro-5-(3,3,3-trifluoropropoxy)benzene (1.3 g, 5.22 mmol) in EtOH (20 mL) and water (2 mL) were added ammonium chloride (1.67 g, 31.3 mmol), iron powder (1.75 g, 31.3 mmol) and HCl (12 N, 2.0 mL, 5.22 mmol). The reaction mixture was heated at 80° C. for 4 h before it was filtered through a CELITE® pad and washed with EtOAc. The organic layer was washed with brine, dried over $Na_2SO_4$, filtered, and concentrated in vacuo to give the crude material as orange oil. The crude material was purified by flash column chromatography eluting with 5% to 50% EtOAc in petroleum ether to provide 3-methyl-5-(3,3,3-trifluoropropoxy)aniline (0.6 g, 2.7 mmol, 52% yield) as a brown oil. $^1H$ NMR (400 MHz, DMSO-$d_6$): δ ppm 6.01 (q, J=1.3 Hz, 1H), 5.96 (t, J=2.2 Hz, 1H), 5.93 (t, J=2.0 Hz, 1H), 4.05 (t, J=5.9 Hz, 2H), 2.69 (qt, J=11.5, 5.9 Hz, 2H), 2.10 (s, 3H). m/z (ESI): 220.1 $(M+H)^+$.

Intermediate 3: 6-(3,3,3-Trifluoropropoxy)pyridin-2-amine

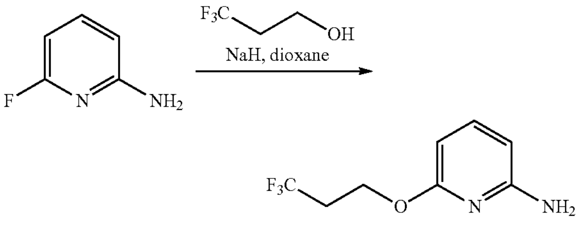

Intermediate 3

A mixture of 6-fluoropyridin-2-amine (1.00 g, 8.92 mmol) and 3,3,3-trifluoropropan-1-ol (2.03 g, 17.84 mmol) in dioxane (15 mL) was treated with NaH (0.86 g, 35.7 mmol) at 0° C. under nitrogen atmosphere and then heated at 90° C. for 2 h. The reaction mixture was quenched with cold water and extracted with EtOAc. The organic extract was washed with brine, dried over $Na_2SO_4$, filtered, and concentrated in vacuo. The crude material was purified by flash column chromatography eluting with 10% to 20% EtOAc in petroleum ether to provide the title compound (1.30 g, 6.31 mmol, 71% yield) as a light-yellow oil. $^1H$ NMR (400 MHz, DMSO-$d_6$): δ ppm 7.29 (t, J=7.8 Hz, 1H), 6.01 (dd, J=7.8, 0.7 Hz, 1H), 5.80-5.91 (m, 3H), 4.34 (t, J=6.2 Hz, 2H), 2.74 (dtd, J=17.7, 11.6, 6.2 Hz, 2H). m/z (ESI): 207.2 $(M+H)^+$.

Intermediate 4: 2-(4,4-Difluoropiperidin-1-yl)-6-methylpyrimidin-4-amine

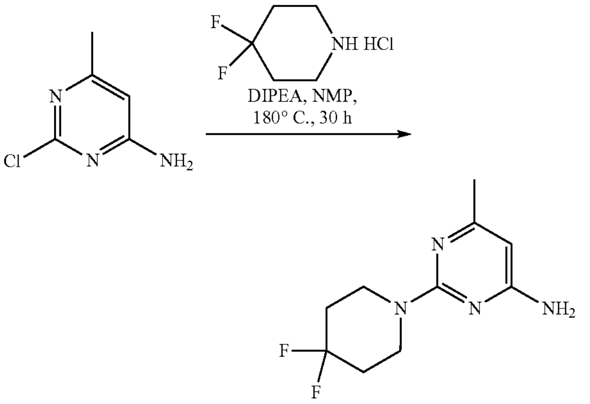

Intermediate 4

A mixture of 2-chloro-6-methylpyrimidin-4-amine (46 g, 320 mmol, Combi-Blocks, San Diego, CA), 4,4-difluoropiperidine hydrochloride (76 g, 481 mmol, Combi-Blocks, San Diego, CA) and DIPEA (166 mL, 961 mmol) in NMP (460 mL, 10.00 mL/g) was taken in an autoclave (1 L) and heated at 180° C. for 30 h. The reaction mixture was cooled to room temperature and quenched with water (500 mL), extracted with EtOAc (2×1000 mL). The organic layer was washed with brine (500 mL), dried ($Na_2SO_4$), filtered, and concentrated under reduced pressure. The crude material was adsorbed onto a plug of silica gel and purified by column chromatography over silica gel, eluting with 50% to 100% EtOAc in hexanes. The product was re-dissolved in EtOAc (500 mL) and washed with water (2×500 mL). The organic layer was dried ($Na_2SO_4$), filtered, and concentrated under reduced pressure. The yellow solid was once again suspended in hexanes (400 mL) and stirred for 30 min. The slurry was filtered, washed with hexanes (100 mL), dried under vacuum to provide the title compound (58 g, 79% yield) as a pale-yellow solid. $^1H$ NMR (400 MHz, DMSO-$d_6$) δ ppm 6.33 (s, 2H), 5.63 (s, 1H), 3.80-3.78 (dd, J=6.8, 4.7 Hz, 4H), 2.06 (s, 3H), 1.95-1.85 (tt, J=14.2, 5.7 Hz, 4H). m/z (ESI): 229.2 $(M+H)^+$.

Intermediate 5: 2-(4,4-Difluoropiperidin-1-yl)-6-methylpyridin-4-amine

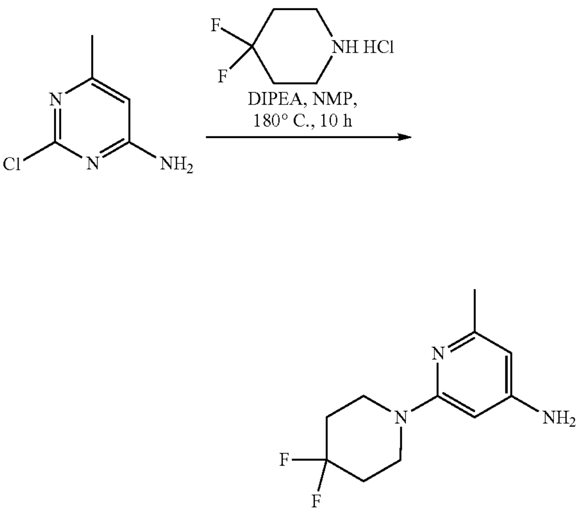

Intermediate 5

A mixture of 2-bromo-6-methylpyridin-4-amine (1.70 g, 9.09 mmol) and 4,4-difluoropiperidine hydrochloride (2.86 g, 18.18 mmol) in NMP (10 mL) was heated at 180° C. for 10 h. The reaction mixture was diluted with $H_2O$ and extracted with EtOAc. The organic layer was washed with brine, dried over $Na_2SO_4$, and concentrated under reduced pressure. The crude material was purified by SFC [method: Greensep Silica (250×30 mm, 5 μm), 70:30 (Liquid $CO_2$:20 mM $NH_3$ in MeOH)] to provide 2-(4,4-difluoropiperidin-1-yl)-6-methylpyridin-4-amine (1.00 g, 4.40 mmol, 49% yield) as a brown oil. $^1H$ NMR (400 MHz, DMSO-$d_6$): δ ppm 5.85 (s, 1H), 5.79-5.91 (m, 3H), 3.45-3.59 (m, 4H), 2.13 (s, 3H), 1.90-2.01 (m, 4H). m/z (ESI): 228.2 $(M+H)^+$.

Intermediate 6: 6-(4,4-Difluoropiperidin-1-yl)-4-methylpyridin-2-amine

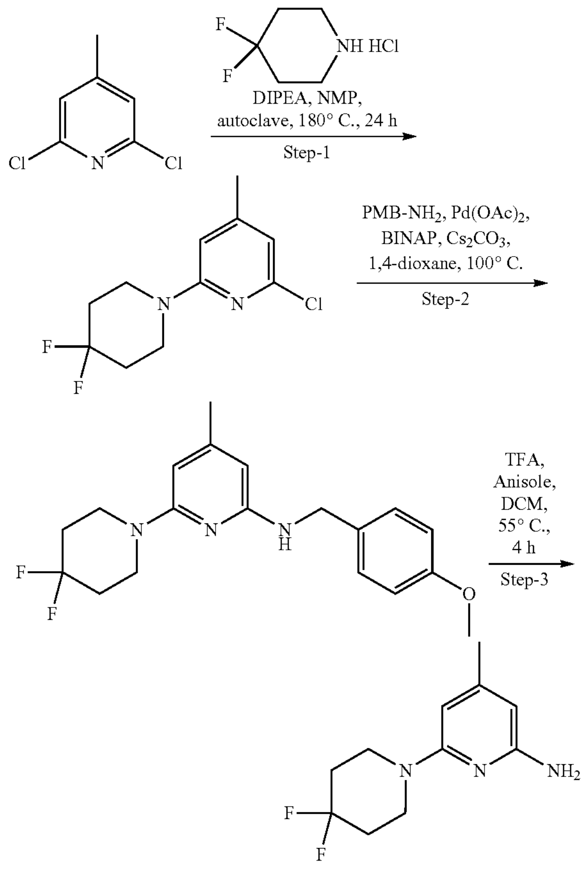

Intermediate 6

Step 1: In an autoclave (3 L) were added 2,6-dichloro-4-methylpyridine (80 g, 490 mmol), 4,4-difluoropiperidine hydrochloride (86 g, 540 mmol), and DIPEA (342 mL, 1980 mmol) in NMP (800 mL). The reaction mixture was heated at 180° C. for 24 h. The reaction mixture was cooled to room temperature and basified to pH-9 using 10% aq. $NaHCO_3$ solution. The reaction mixture was extracted with EtOAc (2×1500 mL), washed with water (1500 mL), dried ($Na_2SO_4$), filtered and concentrated under reduced pressure. The crude material was purified by column chromatography over silica gel (60-120 mesh) using 5-10% EtOAc in hexanes to give the mixture of 2,6-dichloro-4-methylpyridine and 2-chloro-6-(4,4-difluoropiperidin-1-yl)-4-methylpyridine in 1:3 ratio (102 g) as a pale brown oil. This mixture (102 g) was further purified by reverse phase chromatography using 60% $CH_3CN/H_2O$ as an eluent to give 2-chloro-6-(4,4-difluoropiperidin-1-yl)-4-methylpyridine (70 g, 58% yield) as a pale brown liquid. $^1$H NMR (400 MHz, DMSO-$d_6$): δ 6.76 (s, 1H), 6.57 (s, 1H), 3.66 (t, J=5.6 Hz, 4H), 2.22 (s, 3H), 2.03-1.91 (m, 4H). m/z (ESI): 247.1 $(M+H)^+$.

Step 2: To a solution of 2-chloro-6-(4,4-difluoropiperidin-1-yl)-4-methylpyridine (30.0 g, 122 mmol) in 1,4-dioxane (300 mL) were added (4-methoxyphenyl)methanamine (23.8 mL, 182 mmol) and $Cs_2CO_3$ (79 g, 240 mmol). The reaction mixture was degassed and purged with nitrogen for 30 min. BINAP (7.57 g, 12.2 mmol) and $Pd(OAc)_2$ (2.73 g, 12.2 mmol) were added and the reaction mixture was stirred at 100° C. for 16 h. The reaction mixture was cooled to room temperature, filtered through a CELITE® bed, and washed with EtOAc (100 mL). The filtrate was concentrated under reduced pressure. The residue was extracted with EtOAc (2×500 mL), washed with water (500 mL) followed by brine (500 mL). The organic layer was dried ($Na_2SO_4$), filtered, and concentrated under reduced pressure. The crude residue was purified by column chromatography over silica gel using 5-8% EtOAc in hexanes to give 6-(4,4-difluoropiperidin-1-yl)-N-(4-methoxybenzyl)-4-methylpyridin-2-amine (48 g, 76% yield) as a yellow oil. $^1$H NMR (400 MHz, DMSO-$d_6$): δ 7.22 (d, J=7.2 Hz, 2H), 6.85 (d, J=7.2 Hz, 2H), 6.64 (t, J=6.0 Hz, 1H), 5.84 (s, 1H), 5.68 (s, 1H), 4.31 (d, J=6.0 Hz, 2H), 3.71 (s, 3H), 3.56 (t, J=5.6 Hz, 4H), 2.05 (s, 3H), 1.90-1.80 (m, 4H). m/z (ESI): 348.1 $(M+H)^+$.

Step 3: To a solution of 6-(4,4-difluoropiperidin-1-yl)-N-(4-methoxybenzyl)-4-methylpyridin-2-amine (48.0 g, 138 mmol) in dry DCM (480 mL) were added anisole (30.2 mL, 276 mmol) and TFA (240 mL, 3120 mmol). The reaction mixture was stirred at 55° C. for 4 h and concentrated under reduced pressure. The residue was dissolved in water (200 mL) and basified with 10% aq. sodium bicarbonate solution to pH-8 and extracted with EtOAc (2×500 mL). The combined organic layers were washed with water (200 mL) followed by brine (200 mL), dried ($Na_2SO_4$), filtered, and concentrated under reduced pressure. The crude residue was purified by column chromatography over silica gel using 25% to 35% EtOAc in hexanes to give 6-(4,4-difluoropiperidin-1-yl)-4-methylpyridin-2-amine as a brown oil. This material was further purified by reverse phase chromatography using 50-60% $CH_3CN/H_2O$ to give 6-(4,4-difluoropiperidin-1-yl)-4-methylpyridin-2-amine (16.5 g, 72 mmol, 53% yield) as a brown oil. $^1$H NMR (400 MHz, DMSO-$d_6$): δ 5.86 (s, 1H), 5.65 (s, 1H), 5.48 (s, 2H), 3.56 (t, J=5.2 Hz, 4H), 2.06 (s, 3H), 1.96-1.87 (m, 4H). m/z (ESI): 228.2 $(M+H)^+$.

Intermediate 7: 3-(4,4-Difluoropiperidin-1-yl)-5-methylphenol

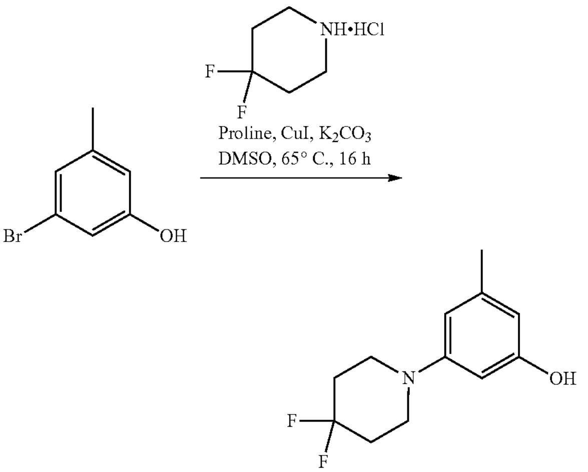

Intermediate 7

A mixture of 3-bromo-5-methylphenol (1.00 g, 5.35 mmol), 4,4-difluoropiperidine hydrochloride (1.26 g, 8.02 mmol), $K_2CO_3$ (1.48 g, 10.69 mmol), copper(I) iodide (0.20 g, 1.07 mmol) and L-proline (0.25 g, 2.14 mmol) in DMSO (10 mL) was heated at 65° C. for 16 h. The reaction mixture was filtered through a CELITE® bed and washed with EtOAc. The organic layer was washed with brine, dried over $Na_2SO_4$, filtered, and concentrated in vacuo. The crude material was purified by flash column chromatography eluting with 0% to 15% EtOAc in petroleum ether to provide 3-(4,4-difluoropiperidin-1-yl)-5-methylphenol (0.20 g, 0.88 mmol, 16% yield) as a brown oil. $^1H$ NMR (400 MHz, DMSO-$d_6$): δ ppm 9.06 (s, 1H), 6.26 (t, J=2.0 Hz, 1H), 6.16 (t, J=2.3 Hz, 1H), 5.95-6.11 (m, 1H), 3.12-3.28 (m, 4H), 2.15 (s, 3H), 1.85-2.09 (m, 4H). m/z (ESI): 228.3 $(M+H)^+$.

Preparation of Ring $Ar^2$ Intermediates

Intermediate 8: 2-Amino-4-bromo-6-(6-azaspiro[2.5]octan-6-yl)benzonitrile

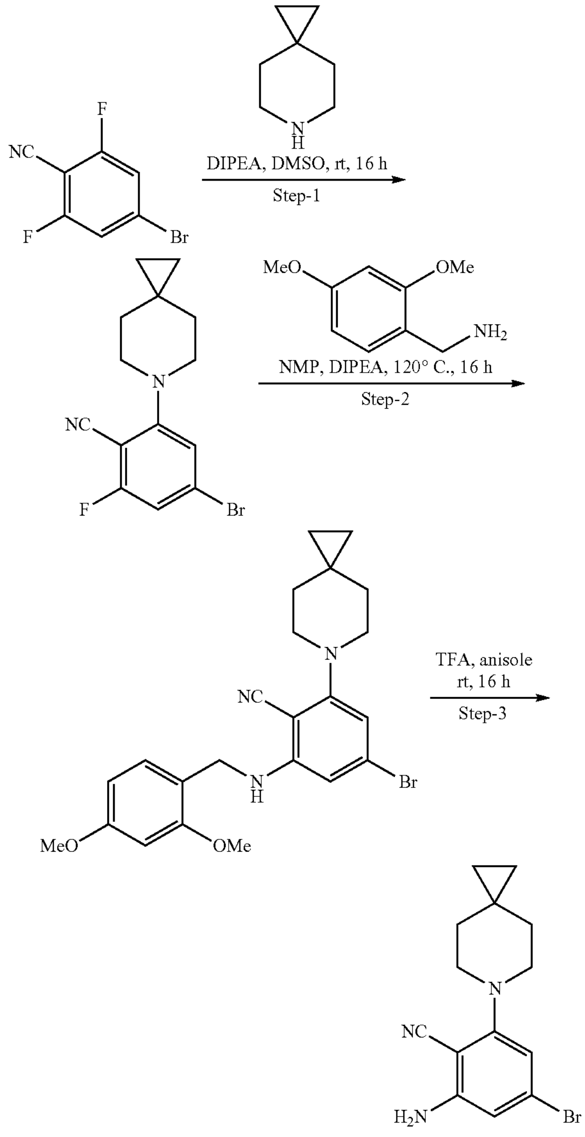

Intermediate 8

Step 1: A solution of 4-bromo-2,6-difluorobenzonitrile (10 g, 46 mmol) and DIPEA (16 mL, 92 mmol) in DMSO (100 mL) was cooled to 0° C. and then treated with 6-azaspiro[2.5]octane (4.1 g, 36.7 mmol). The reaction mixture was stirred at rt for 16 h before it was diluted with water and extracted with EtOAc. The organic extracts were washed with brine, dried over $Na_2SO_4$, filtered, and concentrated in vacuo. The crude product was purified by reverse-phase preparative HPLC (0.1% TFA in $CH_3CN/H_2O$) to provide 4-bromo-2-fluoro-6-(6-azaspiro[2.5]octan-6-yl)benzonitrile (12 g, 39 mmol, 85% yield) as an off-white solid. $^1H$ NMR (400 MHz, Chloroform-d): δ ppm 6.93 (t, J=1.4 Hz, 1H), 6.88 (dd, J=8.1, 1.6 Hz, 1H), 3.31-3.40 (m, 4H), 1.59 (d, J=1.5 Hz, 4H), 0.40 (s, 4H). m/z (ESI): 309.2 (M)+.

Step 2: To a solution of 4-bromo-2-fluoro-6-(6-azaspiro[2.5]octan-6-yl)benzonitrile (1.0 g, 3.2 mmol) and DIPEA (1.13 mL, 6.47 mmol) in NMP (8 mL) was added (2,4-dimethoxyphenyl)methanamine (0.52 g, 3.10 mmol) at rt and the resulting solution was heated at 120° C. for 16 h. The reaction mixture was diluted with water and extracted with EtOAc. The organic extracts were washed with brine, dried over $Na_2SO_4$, filtered, and concentrated in vacuo. The crude product was purified by flash column chromatography using a gradient of 10% to 60% EtOAc in petroleum ether to afford 4-bromo-2-((2,4-dimethoxybenzyl)amino)-6-(6-azaspiro[2.5]octan-6-yl)benzonitrile (1.05 g, 2.30 mmol, 71% yield) as a white solid. $^1H$ NMR (400 MHz, DMSO-$d_6$): δ ppm 7.11 (d, J=8.4 Hz, 1H), 6.52-6.61 (m, 2H), 6.49 (dd, J=8.4, 2.4 Hz, 1H), 6.35-6.42 (m, 2H), 4.26 (d, J=6.0 Hz, 2H), 3.85 (s, 3H), 3.74 (s, 3H), 3.10 (t, J=5.3 Hz, 4H), 1.47 (t, J=5.2 Hz, 4H), 0.33 (s, 4H). m/z (ESI): 456.1/458.1 $(M+H)^+$.

Step 3: A solution of 4-bromo-2-((2,4-dimethoxybenzyl)amino)-6-(6-azaspiro[2.5]octan-6-yl)benzonitrile (1.0 g, 2.2 mmol) and anisole (0.60 mL, 5.48 mmol) in TFA (5 mL) was stirred at rt for 16 h. Then the reaction mixture was quenched with a satd. aq. $NaHCO_3$ and extracted with EtOAc. The organic layer was washed with brine, dried over $Na_2SO_4$, filtered, and concentrated under reduced pressure. The crude product was purified by flash column chromatography using, 20% EtOAc in petroleum ether, to afford 2-amino-4-bromo-6-(6-azaspiro[2.5]octan-6-yl)benzonitrile (0.61 g, 1.99 mmol, 91% yield) as a pale-yellow solid. $^1H$ NMR (400 MHz, DMSO-$d_6$): δ ppm 6.87-7.01 (s, 2H), 6.42 (s, 1H), 6.32 (d, J=1.8 Hz, 1H), 3.04-3.11 (m, 4H), 1.47 (t, J=5.3 Hz, 4H), 0.33 (s, 4H). m/z (ESI): 306.0/308.0 $(M+H)^+$.

Intermediate 9: Ethyl (E)-N-(5-bromo-2-cyano-3-(6-azaspiro[2.5]octan-6-yl)phenyl)formimidate

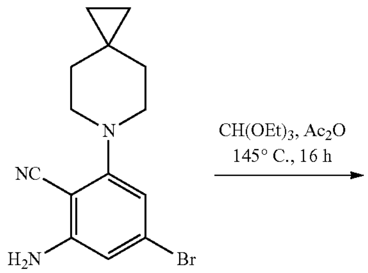

-continued

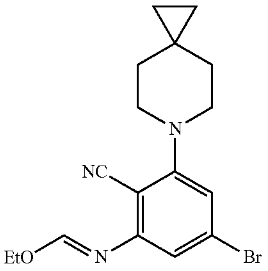

Intermediate 9

A solution of 2-amino-4-bromo-6-(6-azaspiro[2.5]octan-6-yl)benzonitrile (0.4 g, 1.3 mmol, Intermediate 8) in triethyl orthoformate (5 mL, 30 mmol) was treated with $Ac_2O$ (0.1 mL, 1.1 mmol) at rt and then heated at 145° C. for 16 h. Then the reaction mixture was concentrated under reduced pressure and ice-cold water was added to get a solid, which was filtered, to provide the title compound (0.4 g, 1.1 mmol, 85% yield) as a brown solid. The compound was directly taken without further purification. $^1H$ NMR (400 MHz, DMSO-$d_6$): δ ppm 8.11 (s, 1H), 6.88-7.14 (m, 2H), 4.29 (q, J=7.1 Hz, 2H), 3.64-3.83 (m, 4H), 1.49 (t, J=5.3 Hz, 4H), 1.33 (t, J=7.1 Hz, 3H), 0.35 (s, 4H). m/z (ESI): 362.0/364.0 $(M)^+$.

TABLE 1

Intermediate 9-1 was prepared analogous to preparation of Intermediate 9:

| Ex. # | Chemical Structure | Name | LRMS: (ESI + ve ion) m/z |
|---|---|---|---|
| 9-1 | 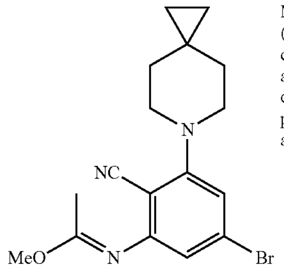 | Methyl (E)-N-(5-bromo-2-cyano-3-(6-azaspiro[2.5]octan-6-yl)phenyl)acetimidate | 363.1 |

Intermediate 10: 2-Amino-4-(methylsulfonyl)-6-(6-azaspiro[2.5]octan-6-yl)benzonitrile

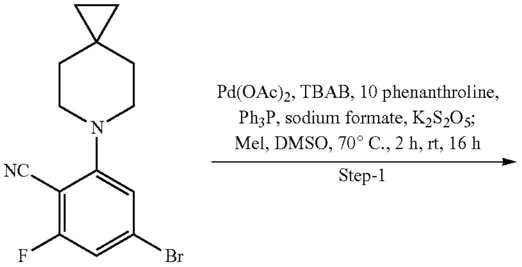

-continued

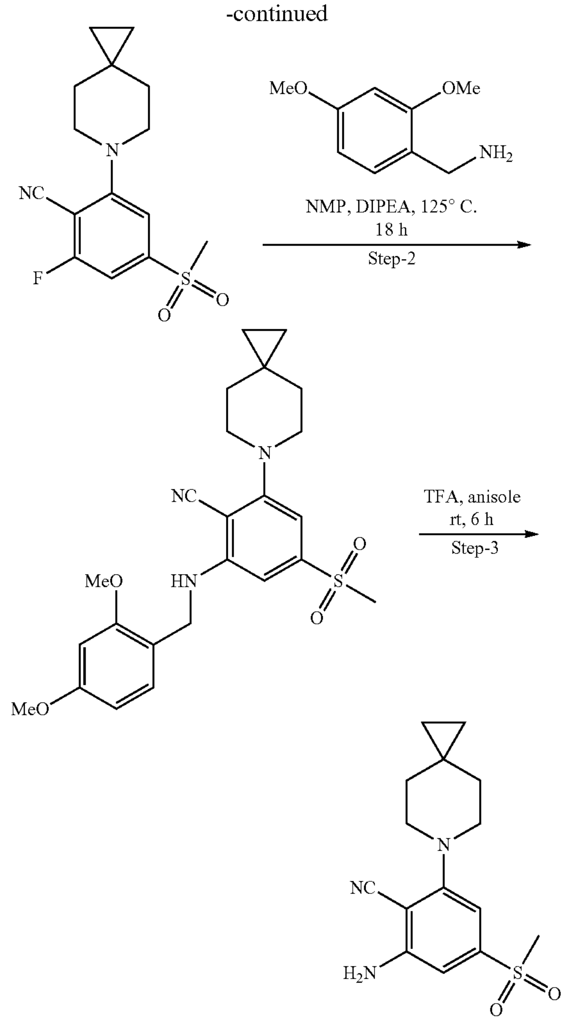

Intermediate 10

Step 1: To a solution of 4-bromo-2-fluoro-6-(6-azaspiro[2.5]octan-6-yl)benzonitrile (2.1 g, 6.8 mmol) in DMSO (1.6 mL) were added tetrabutylammonium bromide (2.41 g, 7.47 mmol), 1,10-phenanthroline (0.184 g, 1.019 mmol), palladium(II) acetate (0.076 g, 0.340 mmol), triphenylphosphine (0.267 g, 1.019 mmol), sodium formate (1.02 g, 14.94 mmol), and di-potassium disulphite (3.02 g, 13.58 mmol) at rt and was heated at 70° C. for 2 h. The reaction mixture was cooled to rt and then iodomethane (0.64 mL, 10.19 mmol) was added to it and stirred for 16 h at rt. The resultant reaction mixture was filtered through a CELITE® pad and washed with EtOAc. The organic layer was washed with brine, filtered, and concentrated to get the crude material which was purified by flash column chromatography eluting with a gradient of 20% to 25% EtOAc in petroleum ether to provide 2-fluoro-4-(methylsulfonyl)-6-(6-azaspiro[2.5]octan-6-yl)benzonitrile (0.68 g, 2.21 mmol, 32% yield) as an off-white solid. $^1H$ NMR (400 MHz, DMSO-$d_6$): δ ppm 7.36-7.46 (m, 2H), 3.37-3.46 (m, 4H), 3.34 (s, 3H), 1.49-1.56 (m, 4H), 0.39 (s, 4H). m/z (ESI): 309.1 $(M+H)^+$.

Step 2: To a mixture of 2-fluoro-4-(methylsulfonyl)-6-(6-azaspiro[2.5]octan-6-yl)benzonitrile (0.65 g, 2.11 mmol) and DIPEA (1.11 mL, 6.32 mmol) in NMP (6.5 mL) was added (2,4-dimethoxyphenyl)methanamine (0.38 g, 2.27 mmol) at rt and then heated at 125° C. for 18 h. The reaction mixture was diluted with water and extracted with EtOAc. The organic layer was washed with brine, filtered, and concentrated to get the crude material which was purified by flash column chromatography eluting with a gradient of 0% to 20% EtOAc in petroleum ether to provide 2-((2,4-dimethoxybenzyl)amino)-4-(methylsulfonyl)-6-(6-azaspiro[2.5]octan-6-yl)benzonitrile (0.68 μg, 1.49 mmol, 71% yield) as a pale-yellow solid. $^1$H NMR (400 MHz, DMSO-$d_6$): δ ppm 7.14 (d, J=8.4 Hz, 1H), 6.85 (t, J=6.1 Hz, 1H), 6.69 (dd, J=17.5, 1.5 Hz, 2H), 6.57 (d, J=2.4 Hz, 1H), 6.49 (dd, J=8.4, 2.4 Hz, 1H), 4.34 (d, J=6.0 Hz, 2H), 3.84 (s, 3H), 3.74 (s, 3H), 3.20-3.18 (m, 4H), 2.70 (s, 3H), 1.50 (t, J=5.3 Hz, 4H), 0.36 (s, 4H). m/z (ESI): 456.1 $(M+H)^+$.

Step 3: To a solution of 2-((2,4-dimethoxybenzyl)amino)-4-(methylsulfonyl)-6-(6-azaspiro[2.5]octan-6-yl)benzonitrile (0.66 g, 1.45 mmol) in TFA (3.3 mL, 42.8 mmol) was added anisole (0.37 mL, 3.62 mmol) at rt and stirred for 6 h. The reaction mixture was evaporated to dryness, quenched with satd. $NaHCO_3$ solution, and extracted with EtOAc. The organic layer was dried over $Na_2SO_4$, filtered, and concentrated under vacuum. The crude product was purified by flash column chromatography using 20% EtOAc in petroleum ether to afford 2-amino-4-(methylsulfonyl)-6-(6-azaspiro[2.5]octan-6-yl)benzonitrile (0.41 g, 1.31 mmol, 90% yield) as a pale-yellow solid. $^1$H NMR (400 MHz, DMSO-d6): δ ppm 6.89 (d, J=1.5 Hz, 1H), 6.60 (d, J=1.6 Hz, 1H), 6.49 (s, 2H), 3.18 (d, J=7.4 Hz, 7H), 1.50 (t, J=5.3 Hz, 4H), 0.35 (s, 4H). m/z (ESI): 306.0 $(M+H)^+$.

Intermediate 11: 2-Amino-6-(6-azaspiro[2.5]octan-6-yl)benzonitrile

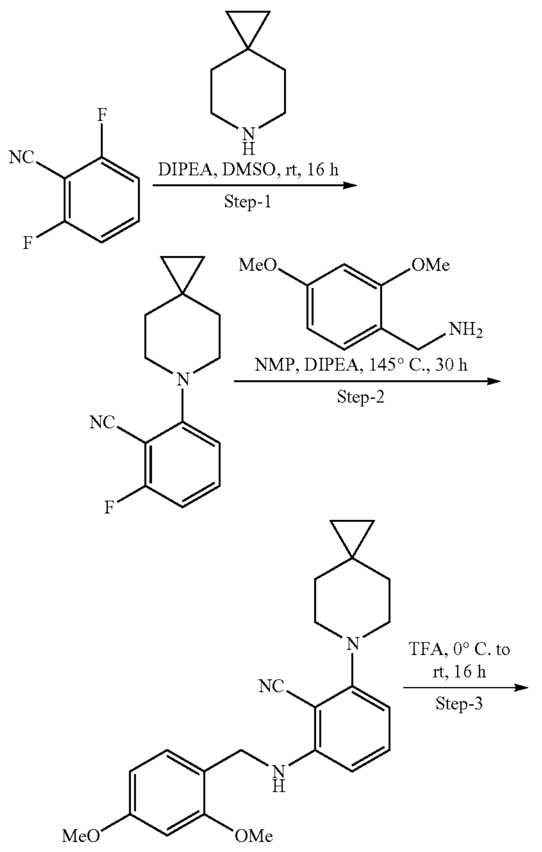

-continued

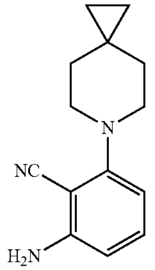

Intermediate 11

Step 1: To a solution of 2,6-difluorobenzonitrile (2.0 g, 14.4 mmol) in DMSO (50 mL) was added DIPEA (5.0 mL, 28.8 mmol) and 6-azaspiro[2.5]octane (1.28 g, 11.50 mmol) at 0° C. and then stirred at rt for 16 h. The reaction mixture was diluted with water and extracted in EtOAc. The organic extract was washed with brine, dried over $Na_2SO_4$, filtered, and concentrated in vacuo. The crude material was purified by flash column chromatography eluting with a gradient of 0% to 5% EtOAc in petroleum ether to provide 2-fluoro-6-(6-azaspiro[2.5]octan-6-yl)benzonitrile (1.86 g, 8.08 mmol, 56% yield) as a colorless sticky liquid. $^1$H NMR (400 MHz, DMSO-$d_6$): δ ppm 7.60 (td, J=8.4, 7.1 Hz, 1H), 6.91-7.03 (m, 2H), 3.22-3.30 (m, 4H), 1.47-1.54 (m, 4H), 0.36 (s, 4H). m/z (ESI): 231.2 $(M+H)^+$.

Step 2: To a solution of 2-fluoro-6-(6-azaspiro[2.5]octan-6-yl)benzonitrile (1.81 g, 7.82 mmol) in NMP (20 mL) were added DIPEA (4.10 mL, 23.45 mmol) and (2,4-dimethoxyphenyl)methanamine (1.44 g, 8.60 mmol) at rt and then heated at 145° C. for 30 h. The reaction mixture was diluted with ice cold water and extracted with EtOAc. The organic extract was washed with brine (100 mL), dried over $Na_2SO_4$, filtered, and concentrated in vacuo to give the crude material as an orange oil. This material was purified by flash column chromatography eluting with a gradient of 0% to 4% EtOAc in petroleum ether to provide 2-((2,4-dimethoxybenzyl)amino)-6-(6-azaspiro[2.5]octan-6-yl)benzonitrile (1.7 g, 4.5 mmol, 58% yield) as alight-yellow solid. $^1$H NMR (400 MHz, DMSO-$d_6$): δ ppm 7.18 (t, J=8.2 Hz, 1H), 7.08 (d, J=8.4 Hz, 1H), 6.57 (d, J=2.4 Hz, 1H), 6.46 (dd, J=8.4, 2.4 Hz, 1H), 6.28 (d, J=7.9 Hz, 1H), 6.11-6.21 (m, 2H), 4.27 (d, J=6.0 Hz, 2H), 3.83 (s, 3H), 3.73 (s, 3H), 3.03-3.11 (m, 4H), 1.49 (t, J=5.3 Hz, 4H), 0.33 (s, 4H). m/z (ESI): 378.2 $(M+H)^+$.

Step 3: To a solution of 2-((2,4-dimethoxybenzyl)amino)-6-(6-azaspiro[2.5]octan-6-yl)benzonitrile (1.7 g, 4.50 mmol) in DCM (20 mL) was dropwise added TFA (1.74 mL, 22.52 mmol) at 0° C. and stirred at rt for 16 h. Then the reaction mixture was evaporated to dryness, diluted with water, neutralized with a satd. $NaHCO_3$ solution, and extracted with DCM. The organic layer was separated, dried over $Na_2SO_4$, filtered, and evaporated to give 2-amino-6-(6-azaspiro[2.5]octan-6-yl)benzonitrile as an orange semi solid which was used for the next step without any purification. $^1$H NMR (400 MHz, DMSO-$d_6$): δ ppm 7.15 (t, J=8.1 Hz, 1H), 6.37 (dd, J=8.4, 0.9 Hz, 1H), 6.22 (dd, J=8.0, 0.9 Hz, 1H), 5.85 (s, 2H), 3.22-3.30 (m, 4H), 1.47-1.54 (m, 4H), 0.36 (s, 4H). m/z (ESI): 228.1 $(M+H)^+$.

Intermediate 12: 7-Bromo-N-(3-(4,4-difluoropiperidin-1-yl)-5-methylphenyl)-5-(6-azaspiro[2.5]octan-6-yl)quinazolin-4-amine

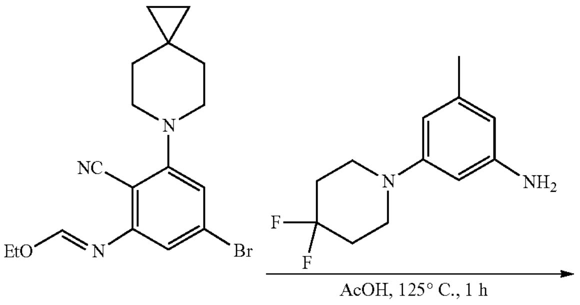

-continued

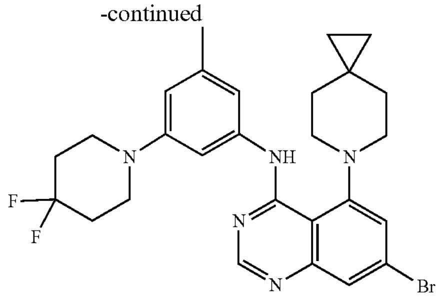

Intermediate 12

To a solution of ethyl (E)-N-(5-bromo-2-cyano-3-(6-azaspiro[2.5]octan-6-yl)phenyl)formimidate (0.2 g, 0.55 mmol, Intermediate 9) in acetic acid (1.9 mL) was added 3-(4,4-difluoropiperidin-1-yl)-5-methylaniline (0.125 g, 0.55 mmol, Intermediate 1) at rt and then was stirred at 125° C. for 1 h. The reaction mixture was diluted with water and extracted with EtOAc (2×). The combined organic extracts were washed with brine, dried over $Na_2SO_4$, filtered, and evaporated under vacuum. The crude product was purified through flash column chromatography eluting with 20% EtOAc in petroleum ether to provide 7-bromo-N-(3-(4,4-difluoropiperidin-1-yl)-5-methylphenyl)-5-(6-azaspiro[2.5]octan-6-yl)quinazolin-4-amine as a yellow solid (54 mg, 18% yield). $^1H$ NMR (400 MHz, DMSO-$d_6$): δ ppm 12.73 (s, 1H), 8.55 (s, 1H), 7.76 (d, J=1.9 Hz, 1H), 7.65 (d, J=2.0 Hz, 1H), 7.42 (s, 1H), 7.15 (t, J=2.0 Hz, 1H), 6.66 (s, 1H), 3.35-3.43 (m, 4H), 2.98 (td, J=11.8, 2.5 Hz, 2H), 2.52 (s, 3H), 2.23 (d, J=9.5 Hz, 2H), 2.03-2.14 (m, 6H), 1.93-2.05 (m, 2H), 0.35-0.48 (m, 4H). m/z (ESI): 542.1/544.1 $(M+H)^+$.

TABLE 2

Intermediate 12-1 was prepared analogous to preparation of Intermediate 12:

| Ex. # | Chemical Structure | Name | LRMS: (ESI + ve ion) m/z |
|---|---|---|---|
| 12-1 | 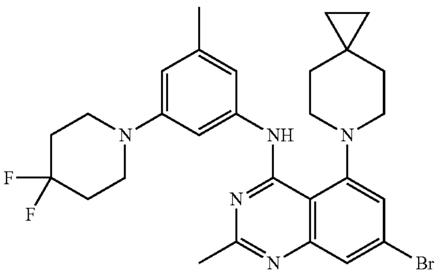 [SMILES: Cc1cc(Nc2nc(C)nc3cc(Br)cc(N4CCC5(CC4)CC5)c23)cc(N2CCC(F)(F)CC2)c1] | 7-Bromo-N-(3-(4,4-difluoropiperidin-1-yl)-5-methylphenyl)-2-methyl-5-(6-azaspiro[2.5]octan-6-yl)quinazolin-4-amine | 556.1/558.1 |

Example 100: N-(4-((3-(4,4-Difluoropiperidin-1-yl)-5-methylphenyl)amino)-5-(6-azaspiro[2.5]octan-6-yl)quinazolin-7-yl)-2-hydroxyethane-1-sulfonamide

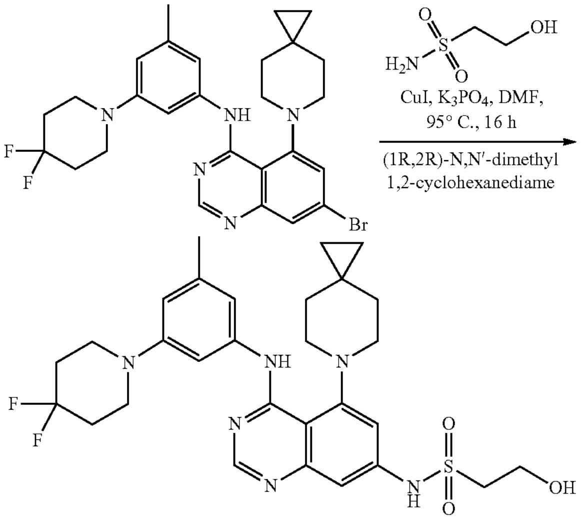

To a solution of 7-bromo-N-(3-(4,4-difluoropiperidin-1-yl)-5-methylphenyl)-5-(6-azaspiro[2.5]octan-6-yl)quinazolin-4-amine (0.125 g, 0.230 mmol, Intermediate 12) and 2-hydroxyethane-1-sulfonamide (0.058 g, 0.461 mmol) in DMF (2 mL) were added potassium phosphate tribasic (0.147 g, 0.691 mmol), copper(I) iodide (0.088 g, 0.461 mmol) and (1R,2R)—N,N-dimethyl-1,2-cyclohexanediamine (0.033 g, 0.230 mmol) at rt and was heated at 95° C. for 16 h. The reaction mixture was filtered through a CELITE® pad and washed with EtOAc. The combined organic extracts were washed with brine, dried over $Na_2SO_4$, filtered, and evaporated to get the crude compound. The crude product was purified by preparative HPLC [Sun fire C-18 (150×19) mm, 5.0 μm, 0.1% TFA in $CH_3CN/H_2O$] to afford N-(4-((3-(4,4-difluoropiperidin-1-yl)-5-methylphenyl)amino)-5-(6-azaspiro[2.5]octan-6-yl)quinazolin-7-yl)-2-hydroxyethane-1-sulfonamide 2,2,2-trifluoroacetate (0.03 g, 0.04 mmol, 19% yield) as a yellow solid. $^1H$ NMR (400 MHz, DMSO-$d_6$): δ ppm 13.28 (s, 1H), 10.86 (s, 1H), 8.84 (s, 1H), 7.39-7.47 (m, 2H), 7.25 (s, 1H), 7.11 (t, J=2.1 Hz, 1H), 6.83 (s, 1H), 4.98 (s, 1H), 3.81 (t, J=6.1 Hz, 2H), 3.50 (t, J=6.1 Hz, 2H), 3.41 (t, J=5.7 Hz, 4H), 3.26 (d, J=11.0 Hz, 2H), 2.87 (dd, J=12.8, 10.2 Hz, 2H), 2.33 (s, 3H), 1.99-2.22 (m, 6H), 1.10 (d, J=13.3 Hz, 2H), 0.42 (q, J=3.2 Hz, 4H). m/z (ESI): 587.2 $(M+H)^+$.

TABLE 3

Example 100-1 was prepared analogous to preparation of Example 100:

| Ex. # | Chemical Structure | Name | LRMS: (ESI + ve ion) m/z |
|---|---|---|---|
| 100-1 | 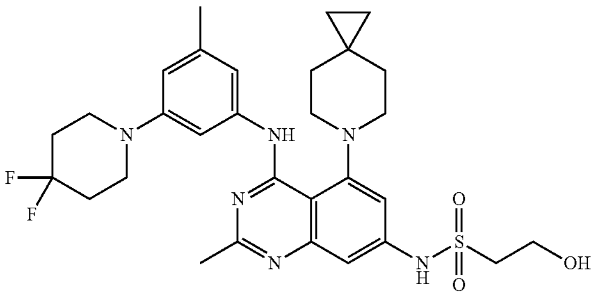 [SMILES: Cc1cc(Nc2nc(C)nc3cc(NS(=O)(=O)CCO)cc(N4CCC5(CC4)CC5)c23)cc(N2CCC(F)(F)CC2)c1] | N-(4-((3-(4,4-Difluoropiperidin-1-yl)-5-methylphenyl)amino)-2-methyl-5-(6-azaspiro[2.5]octan-6-yl)quinazolin-7-yl)-2-hydroxyethane-1-sulfonamide | 601.3 |

Example 101: N-(3-(4,4-Difluoropiperidin-1-yl)-5-methylphenyl)-7-(methylsulfonyl)-5-(6-azaspiro[2.5]octan-6-yl)quinazolin-4-amine

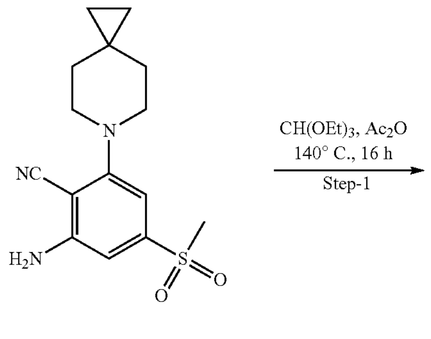

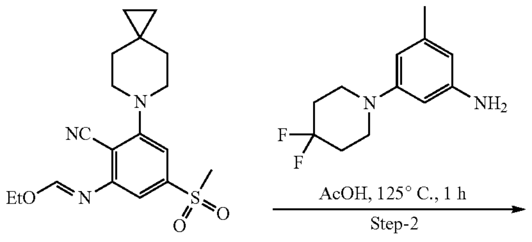

-continued

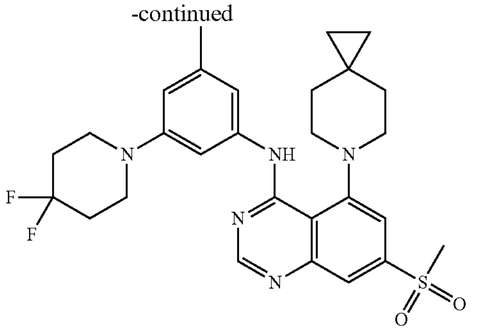

Step 1: To a solution of 2-amino-4-(methylsulfonyl)-6-(6-azaspiro[2.5]octan-6-yl)benzonitrile (0.41 g, 1.34 mmol, Intermediate 10) in triethyl orthoformate (2.0 mL, 12 mmol) was added $Ac_2O$ (0.1 mL, 1.06 mmol) at rt and then heated at 140° C. for 16 h. The reaction mixture was evaporated to dryness and ice-cold water was added. The solid obtained was filtered and dried under suction to get the ethyl (E)-N-(2-cyano-5-(methylsulfonyl)-3-(6-azaspiro[2.5]octan-6-yl)phenyl)formimidate (0.41 g, 1.13 mmol, 84% yield) as a brown solid. $^1H$ NMR (400 MHz, DMSO-$d_6$): δ ppm 8.21 (s, 1H), 7.28 (d, J=1.5 Hz, 1H), 7.22 (d, J=1.5 Hz, 1H), 4.33 (q, J=7.0 Hz, 2H), 3.29 (s, 3H), 3.28 (dd, J=6.4, 4.5 Hz, 4H), 1.53 (t, J=5.3 Hz, 4H), 1.35 (t, J=7.1 Hz, 3H), 0.37 (s, 4H). m/z (ESI): 362.1 $(M+H)^+$.

Step 2: To a solution of ethyl (E)-N-(2-cyano-5-(methylsulfonyl)-3-(6-azaspiro[2.5]octan-6-yl)phenyl)formimidate (0.19 g, 0.54 mmol) in AcOH (2 mL) was added 3-(4,4-difluoropiperidin-1-yl)-5-methylaniline (0.121 g, 0.537 mmol, Intermediate 1) at rt and heated at 125° C. for 1 h. Then water was added to the reaction mixture and extracted with EtOAc. The organic layer dried over $Na_2SO_4$, filtered, and evaporated. The crude product was purified by preparative HPLC [X-Select C18 (250×19) mm, 5 μm, 0.1% TFA in $CH_3CN/H_2O$) to get the N-(3-(4,4-difluoropiperidin-1-yl)-5-methylphenyl)-7-(methylsulfonyl)-5-(6-azaspiro[2.5]octan-6-yl)quinazolin-4-amine 2,2,2-trifluoroacetate (0.18 g, 0.27 mmol, 51% yield) as a yellow solid. $^1H$ NMR (400 MHz, DMSO-$d_6$): δ ppm 13.44 (s, 1H), 8.88 (s, 1H), 8.03-8.09 (m, 2H), 7.37 (s, 1H), 7.17 (t, J=2.0 Hz, 1H), 6.80 (s, 1H), 3.39-3.43 (m, 7H), 3.25-3.32 (m, 2H), 3.10 (dd, J=12.7, 10.1 Hz, 2H), 2.34 (s, 3H), 2.18-2.28 (m, 2H), 2.07 (tt, J=14.0, 5.6 Hz, 4H), 1.11 (d, J=13.3 Hz, 2H), 0.44-0.42 (m, 4H). m/z (ESI): 542.2 $(M+H)^+$.

TABLE 4

Example 101-1 was prepared analogous to preparation of Example 101:

| Ex. # | Chemical Structure | Name | LRMS: (ESI + ve ion) m/z |
|---|---|---|---|
| 101-1 | 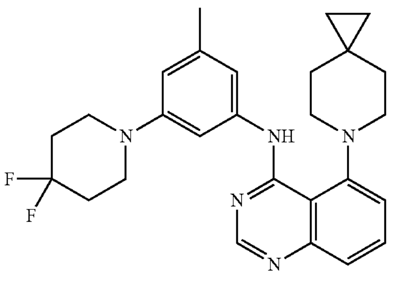 [SMILES: Cc1cc(Nc2ncnc3cccc(N4CCC5(CC4)CC5)c23)cc(N2CCC(F)(F)CC2)c1] | N-(3-(4,4-Difluoropiperidin-1-yl)-5-methylphenyl)-5-(6-azaspiro[2.5]octan-6-yl)quinazolin-4-amine | 464.2 |

Examples 102-1 and 102-2: (R)-cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone (Example 102-1) and (S)-cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone (Example 102-2)

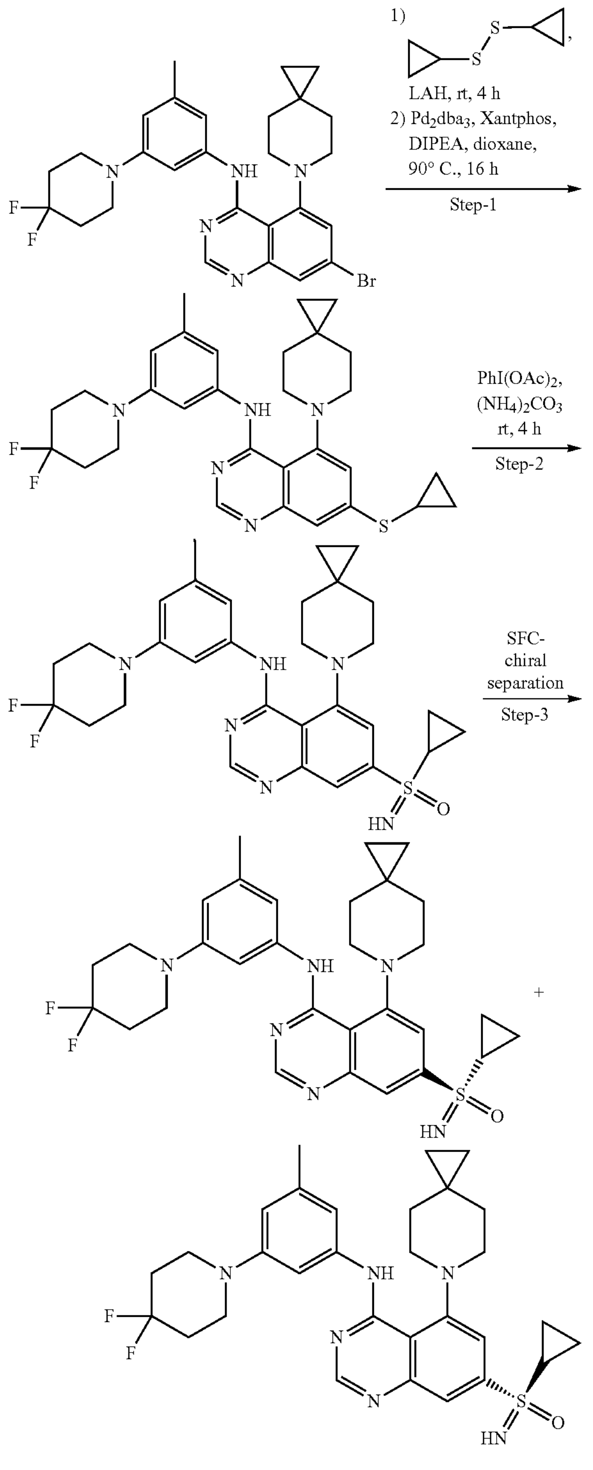

Step 1: To a solution of 1,2-dicyclopropyldisulfane (2.0 g, 13.7 mmol) in $Et_2O$ (20 mL) was dropwise added $LiAlH_4$ (4.0 M in $Et_2O$, 3.42 mL, 13.67 mmol) at 0° C. under a nitrogen atmosphere and stirred for 1 h at 0° C. The reaction mixture was diluted with $Et_2O$ and quenched with a satd. aq. $NH_4Cl$ solution and extracted with $Et_2O$ (2×). The combined organic extracts were dried over $Na_2SO_4$, filtered, and concentrated in vacuo to give the crude cyclopropanethiol (0.44 g, 5.90 mmol) as a colorless liquid which was used for the next reaction. To a solution of 7-bromo-N-(3-(4,4-difluoropiperidin-1-yl)-5-methylphenyl)-5-(6-azaspiro[2.5]octan-6-yl)quinazolin-4-amine (0.32 g, 0.59 mmol, Intermediate 12) and DIPEA (0.41 mL, 2.36 mmol) in dioxane (3.2 mL) were added xantphos (0.068 g, 0.118 mmol), $Pd_2(dba)_3$ (0.054 g, 0.059 mmol) and cyclopropanethiol (0.437 g, 5.90 mmol) and the resulting mixture was heated at 90° C. for 16 h. The reaction mixture was diluted with EtOAc, passed through a CELITE® bed, and washed with EtOAc. The organic layer was dried over $Na_2SO_4$, filtered, and concentrated. The crude product was purified by flash column chromatography using a gradient of 20% EtOAc in petroleum ether to get the 7-(cyclopropylthio)-N-(3-(4,4-difluoropiperidin-1-yl)-5-methylphenyl)-5-(6-azaspiro[2.5]octan-6-yl)quinazolin-4-amine (0.30 g, 0.56 mmol, 95% yield) as a light brown solid. $^1H$ NMR (400 MHz, DMSO-$d_6$): δ ppm 12.74 (s, 1H), 8.50 (s, 1H), 7.53 (d, J=1.8 Hz, 1H), 7.44 (s, 1H), 7.36 (d, J=1.9 Hz, 1H), 7.15 (s, 1H), 6.63 (s, 1H), 3.39 (t, J=5.7 Hz, 4H), 3.30 (d, J=10.0 Hz, 2H), 3.17 (d, J=11.0 Hz, 2H), 2.20-2.33 (m, 5H), 2.07 (tt, J=14.0, 5.5 Hz, 4H), 1.16-1.29 (m, 2H), 1.06 (t, J=11.4 Hz, 2H), 0.78-0.89 (m, 1H), 0.67 (dt, J=6.7, 4.4 Hz, 2H), 0.35-0.47 (m, 4H). m/z (ESI): 536.2 $(M+H)^+$.

Step 2: To a solution of 7-(cyclopropylthio)-N-(3-(4,4-difluoropiperidin-1-yl)-5-methylphenyl)-5-(6-azaspiro[2.5]octan-6-yl)quinazolin-4-amine (0.27 g, 0.50 mmol) in MeOH (2.7 mL) were added phenyl-13-iodanediyl diacetate (0.49 g, 1.51 mmol) and ammonium carbonate (0.29 g, 3.02 mmol) at rt and stirred for 4 h. The reaction mixture was evaporated, diluted with water, and extracted in EtOAc. The combined organic extracts were washed with brine, dried over $Na_2SO_4$, filtered, and concentrated to get crude product as black sticky oil. This material was purified by flash column chromatography eluting with 60% to 70% EtOAc in petroleum ether to provide cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone (0.08 g, 0.14 mmol, 28% yield) as a yellow solid. $^1H$ NMR (400 MHz, DMSO-$d_6$): δ ppm 12.87 (s, 1H), 8.65 (s, 1H), 7.99 (d, J=1.8 Hz, 1H), 7.87 (d, J=1.8 Hz, 1H), 7.45 (s, 1H), 7.18 (t, J=2.1 Hz, 1H), 6.68 (s, 1H), 4.61 (s, 1H), 3.41-3.40 (s, 4H), 3.25 (d, J=11.0 Hz, 2H), 3.00 (t, J=11.4 Hz, 2H), 2.89 (m, 1H), 2.54 (s, 3H), 2.43-2.48 (m, 2H), 2.08 (td, J=13.9, 7.0 Hz, 4H), 0.96-1.13 (m, 2H), 0.91-1.00 (m, 2H), 0.44 (s, 4H). m/z (ESI): 567.3 $(M+H)^+$. The racemic mixture was separated via chiral preparative SFC using a Chiralpak AD (250×21 mm, 5 mm) column with a mobile phase of 50% liquid $CO_2$ and 50% IPA to give mg of (R)-cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone (peak 1, Example 102-1). $^1H$ NMR (400 MHz, DMSO-$d_6$): δ ppm 12.87 (s, 1H), 8.65 (s, 1H), 7.99 (d, J=1.8 Hz, 1H), 7.87 (d, J=1.8 Hz, 1H), 7.45 (s, 1H), 7.18 (t, J=2.1 Hz, 1H), 6.68 (s, 1H), 4.61 (s, 1H), 3.41-3.40 (s, 4H), 3.25 (d, J=11.0 Hz, 2H), 3.00 (t, J=11.4 Hz, 2H), 2.89 (m, 1H), 2.54 (s, 3H), 2.43-2.48 (m, 2H), 2.08 (td, J=13.9, 7.0 Hz, 4H), 0.96-1.13 (m, 2H), 0.91-1.00 (m, 2H), 0.44 (s, 4H). m/z (ESI): 567.3 $(M+H)^+$ and 24 mg of (S)-cyclopropyl(4-((3-

(4,4-difluoropiperidin-1-yl)-5-methylphenyl)amino)-5-(6-azaspiro[2.5]octan-6-yl)quinazolin-7-yl)(imino)-16-sulfanone (peak 2, Example 102-2), $^1$H NMR (400 MHz, DMSO-$d_6$): δ ppm 12.87 (s, 1H), 8.65 (s, 1H), 7.99 (d, J=1.8 Hz, 1H), 7.87 (d, J=1.8 Hz, 1H), 7.44 (s, 1H), 7.17 (t, J=2.1 Hz, 1H), 6.68 (s, 1H), 4.61 (s, 1H), 3.43-3.40 (s, 4H), 3.26 (d, J=11.0 Hz, 2H), 3.00 (t, J=11.4 Hz, 2H), 2.85 (m, 1H), 2.55 (s, 3H), 2.41-2.48 (m, 2H), 2.08 (td, J=13.9, 7.0 Hz, 4H), 0.96-1.13 (m, 2H), 0.91-1.00 (m, 4H), 0.44 (s, 4H). m/z (ESI): 567.3 $(M+H)^+$.

The stereochemistry of Examples 102-1 and 102-2 was assigned arbitrarily.

Example 103: 2-Hydroxy-N-(4-((3-methyl-5-(3,3,3-trifluoropropoxy)phenyl)amino)-5-(6-azaspiro[2.5]octan-6-yl)quinazolin-7-yl)ethane-1-sulfonamide)

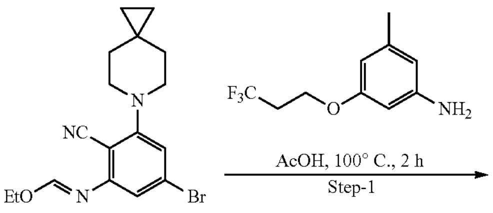

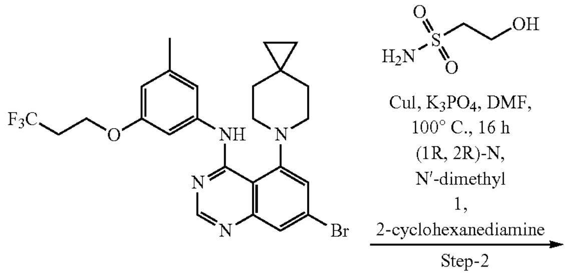

-continued

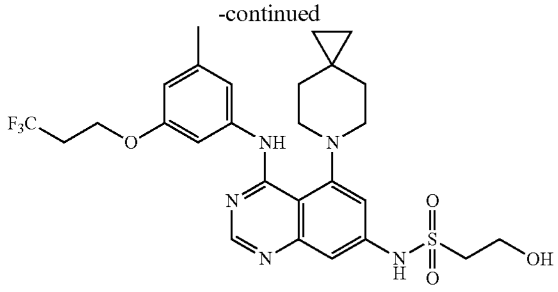

Step 1: To a solution of ethyl 1-N-(5-bromo-2-cyano-3-(6-azaspiro[2.5]octan-6-yl)phenyl)formimidate (0.35 g, 0.97 mmol, Intermediate 9) and 3-methyl-5-(3,3,3-trifluoropropoxy)aniline (0.21 g, 0.97 mmol, Intermediate 2) in AcOH (2 mL, 35 mmol) was heated at 100° C. for 2 h. Then the reaction mixture was concentrated under reduced pressure and the residue was dissolved in EtOAc. The organic layer was washed with water, brine, dried over $Na_2SO_4$, filtered, and evaporated to dryness. The crude material was purified by flash column chromatography eluting with a gradient of 30% to 35% EtOAc in petroleum ether to provide 7-bromo-N-(3-methyl-5-(3,3,3-trifluoropropoxy)phenyl)-5-(6-azaspiro[2.5]octan-6-yl)quinazolin-4-amine (220 mg, 31% yield). m/z (ESI): 535.1 (M)+.

Step 2: To a solution of 7-bromo-N-(3-methyl-5-(3,3,3-trifluoropropoxy)phenyl)-5-(6-azaspiro[2.5]octan-6-yl)quinazolin-4-amine (0.220 g, 0.411 mmol) and 2-hydroxyethane-1-sulfonamide (0.062 g, 0.493 mmol) in DMF (4 mL) were added tripotassium phosphate (0.174 g, 0.822 mmol) and copper (I) iodide (0.078 g, 0.411 mmol), followed by (1R,2R)—N,N'-dimethyl-1,2-cyclohexanediamine (0.029 g, 0.205 mmol) at rt and the reaction mixture was heated at 100° C. for 16 h. The reaction mixture passed through a bed of CELITE® and washed with EtOAc. The organic layer was washed with water, brine, dried over $Na_2SO_4$, filtered, and evaporated to dryness. The crude product was purified by reverse-phase preparative HPLC (C-18 gold column, $CH_3CN/H_2O$, gradient 65% to 70%) to provide 2-hydroxy-N-(4-((3-methyl-5-(3,3,3-trifluoropropoxy)phenyl)amino)-5-(6-azaspiro[2.5]octan-6-yl)quinazolin-7-yl)ethane-1-sulfonamide (0.040 g, 0.069 mmol, 17% yield) as an off-white solid. $^1$H NMR (400 MHz, DMSO-$d_6$): δ ppm 10.78 (s, 1H), 8.79 (s, 1H), 7.35-7.45 (m, 2H), 7.31 (t, J=2.2 Hz, 1H), 7.24 (d, J=2.0 Hz, 1H), 6.76 (s, 1H), 5.02 (s, 1H), 4.24 (t, J=5.9 Hz, 2H), 3.80 (t, J=6.2 Hz, 2H), 3.21-3.25 (m, 5H), 2.84 (m, 4H), 2.36 (s, 3H), 2.16 (t, J=12.0 Hz, 2H), 1.09 (d, J=13.3 Hz, 2H), 0.43 (m, 4H). m/z (ESI): 580.2 $(M+H)^+$.

TABLE 5

Examples 103-1 and 103-2 were prepared analogous to preparation of Example 103:

| Ex. # | Chemical Structure | Name | LRMS: (ESI + ve ion) m/z |
|---|---|---|---|
| 103-1 | 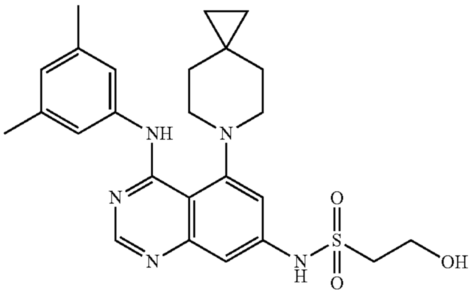 [SMILES: Cc1cc(C)cc(Nc2ncnc3cc(NS(=O)(=O)CCO)cc(N4CCC5(CC4)CC5)c23)c1] | N-(4-((3,5-Dimethylphenyl)amino)-5-(6-azaspiro[2.5]octan-6-yl)quinazolin-7-yl)-2-hydroxyethane-1-sulfonamide | 482.2 |

TABLE 5-continued

| Examples 103-1 and 103-2 were prepared analogous to preparation of Example 103: | | | |
|---|---|---|---|
| Ex. # | Chemical Structure | Name | LRMS: (ESI + ve ion) m/z |
| 103-2 | 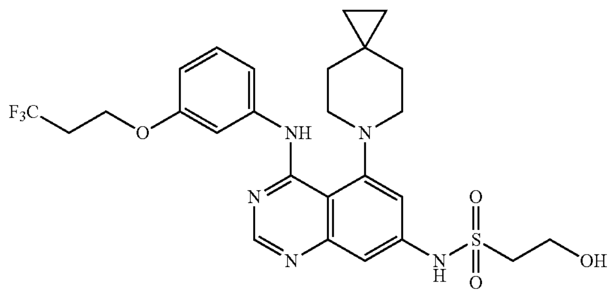 [SMILES: O=S(=O)(CCO)Nc1cc(N2CCC3(CC2)CC3)c2c(Nc3cccc(OCCC(F)(F)F)c3)ncnc2c1] | N-(5-(6-Azaspiro[2.5]octan-6-yl)-4-((3-(3,3,3-trifluoropropoxy)phenyl)amino)quinazolin-7-yl)-2-hydroxyethane-1-sulfonamide | 566.1 |

Example 104: N-(4-((2-(4,4-Difluoropiperidin-1-yl)-6-methylpyrimidin-4-yl)amino)-5-(6-azaspiro[2.5]octan-6-yl)quinazolin-7-yl)-2-hydroxyethane-1-sulfonamide

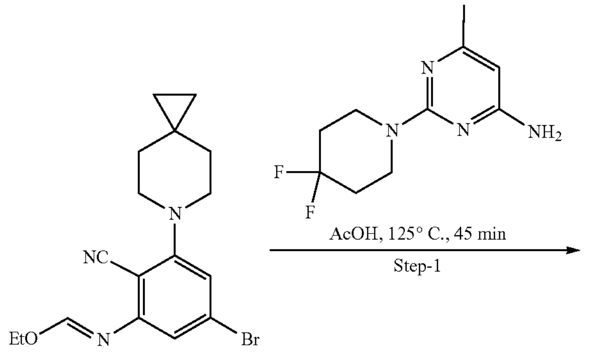

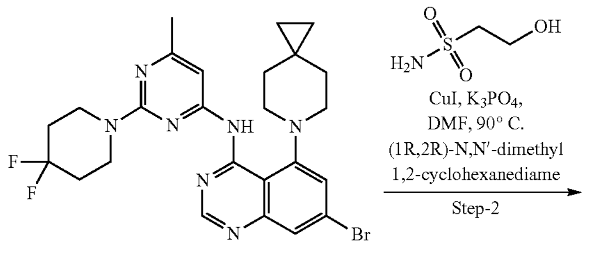

-continued

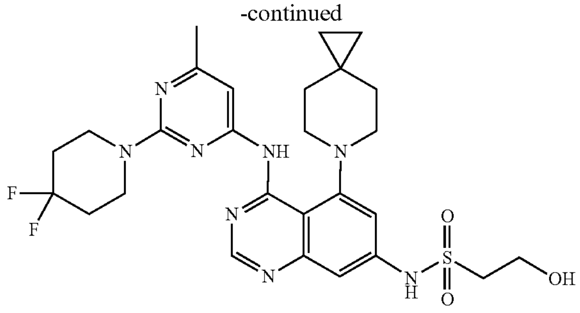

Step 1: A solution of ethyl (E)-N-(5-bromo-2-cyano-3-(6-azaspiro[2.5]octan-6-yl)phenyl)formimidate (0.50 g, 1.38 mmol, Intermediate 9) and 2-(4,4-difluoropiperidin-1-yl)-6-methylpyrimidin-4-amine (0.31 g, 1.38 mmol, Intermediate 4) in AcOH (2 mL) was heated at 125° C. for 45 min. The reaction mixture was diluted with water and extracted with EtOAc. The organic layer was washed with brine, dried over $Na_2SO_4$, filtered, and concentrated in vacuo. The crude material was purified by flash column chromatography eluting with 0% to 30% EtOAc in petroleum ether to provide 7-bromo-N-(2-(4,4-difluoropiperidin-1-yl)-6-methylpyrimidin-4-yl)-5-(6-azaspiro[2.5]octan-6-yl)quinazolin-4-amine (0.15 g, 0.28 mmol, 20% yield) as a pale-yellow solid. $^1H$ NMR (400 MHz, DMSO-$d_6$): δ ppm 13.67 (s, 1H), 8.76 (s, 1H), 7.89-7.88 (m, 2H), 7.76 (s, 1H), 3.95 (t, J=5.8 Hz, 4H), 3.19 (d, J=11.1 Hz, 2H), 3.05 (q, J=12.2, 11.3 Hz, 2H), 2.36 (s, 3H), 1.96-2.05 (m, 4H), 1.14-1.26 (m, 4H), 0.38 (s, 4H). m/z (ESI): 544.2/546.2 $(M+H)^+$.

Step 2: A mixture of 7-bromo-N-(2-(4,4-difluoropiperidin-1-yl)-6-methylpyrimidin-4-yl)-5-(6-azaspiro[2.5]octan-6-yl)quinazolin-4-amine (0.14 g, 0.26 mmol), 2-hydroxyethane-1-sulfonamide (0.048 g, 0.386 mmol), potassium phosphate tribasic (0.164 g, 0.771 mmol), copper(I) iodide (0.098 g, 0.514 mmol) and (1R,2R)—N,N-dimethyl-1,2-cyclohexanediamine (0.037 g, 0.257 mmol) in DMF (2 mL) was heated at 90° C. for 16 h. The reaction mixture was filtered through a CELITE® pad and washed with EtOAc. The organic layers were washed with brine, dried over $Na_2SO_4$, filtered, and evaporated to dryness. The crude product was purified by preparative HPLC [Kinetex Evo C-18 (250×30) mm, 5 μm, 0.1% TFA, $CH_3CN/H_2O$] to afford N-(4-((2-(4,4-difluoropiperidin-1-yl)-6-methylpyrimidin-4-yl)amino)-5-(6-azaspiro[2.5]octan-6-yl)quinazolin-7-yl)-2-hydroxyethane-1-sulfonamide 2,2,2-trifluoroacetate (0.07 g, 0.10 mmol, 39% yield) as a pale yellow solid. $^1$H NMR (400 MHz, DMSO-$d_6$): δ ppm 13.86 (s, 1H), 10.74 (s, 1H), 8.90 (s, 1H), 7.86 (s, 1H), 7.46 (s, 2H), 3.95 (t, J=5.8 Hz, 4H), 3.80 (t, J=6.2 Hz, 2H), 3.48 (d, J=12.4 Hz, 2H), 3.22 (d, J=10.8 Hz, 2H), 2.88 (t, J=11.5 Hz, 2H), 2.43-2.48 (m, 2H), 2.38 (s, 3H), 2.02 (m, 4H), 1.03 (d, J=12.9 Hz, 2H), 0.40-0.46 (m, 4H). m/z (ESI): 589.2 $(M+H)^+$.

Example 105: N-(4-((2-(4,4-Difluoropiperidin-1-yl)-6-methylpyridin-4-yl)amino)-5-(6-azaspiro[2.5]octan-6-yl)quinazolin-7-yl)-2-hydroxyethane-1-sulfonamide

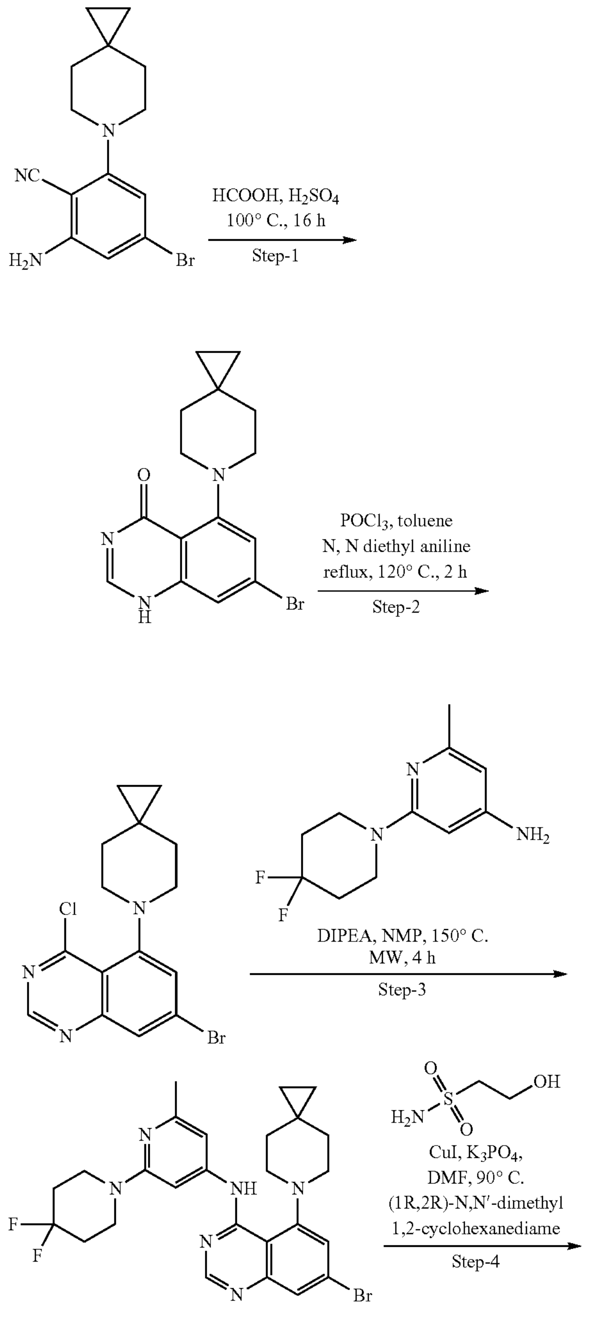

-continued

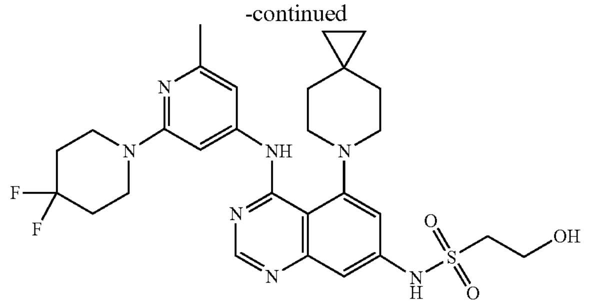

Step 1: A mixture of formic acid (5 mL) and sulfuric acid (0.2 mL, 3.75 mmol) was heated at 100° C. for 5 min. A solution of 2-amino-4-bromo-6-(6-azaspiro[2.5]octan-6-yl)benzonitrile (1.6 g, 5.2 mmol, Intermediate 8) in formic acid (5 mL) was added dropwise to the above mixture for 5 min at the same temperature and heating was continued for 16 h. The reaction mixture was treated with ice and neutralized with an aq. satd. $NaHCO_3$ solution and extracted with EtOAc (2×). The combined organic extracts were washed with brine, dried over $Na_2SO_4$, filtered, and concentrated under reduced pressure. The residue was triturated with $Et_2O$ to provide 7-bromo-5-(6-azaspiro[2.5]octan-6-yl)quinazolin-4(3H)-one (1.6 g, 4.8 mmol, 92% yield) as a light-yellow solid. $^1$H NMR (400 MHz, DMSO-$d_6$): δ ppm 11.96 (s, 1H), 7.99 (s, 1H), 7.27 (d, J=1.9 Hz, 1H), 7.02 (d, J=2.0 Hz, 1H), 3.04 (s, 4H), 1.53 (s, 4H), 0.32 (s, 4H). m/z (ESI): 334.1/336.1 $(M+H)^+$.

Step 2: A solution of 7-bromo-5-(6-azaspiro[2.5]octan-6-yl)quinazolin-4(3H)-one (0.35 g, 1.05 mmol) in toluene (7 mL) was treated with phosphorus oxychloride (0.195 mL, 2.094 mmol) and N,N-diethylaniline (0.313 g, 2.094 mmol) at rt and was heated at 120° C. for 2 h. It was cooled to rt, volatiles were evaporated under reduced pressure to get crude residue which was further co-distilled with toluene to afford 7-bromo-4-chloro-5-(6-azaspiro[2.5]octan-6-yl)quinazoline as a brown solid (0.43 g). It was directly used for the next step without further purification. m/z (ESI): 352.1/354.1 $(M+H)^+$.

Step 3: A glass microwave vial was successively charged with 7-bromo-4-chloro-5-(6-azaspiro[2.5]octan-6-yl)quinazoline (0.21 g, 0.57 mmol), 2-(4,4-difluoropiperidin-1-yl)-6-methylpyridin-4-amine (0.16 g, 0.68 mmol, Intermediate 5) and DIPEA (0.099 mL, 0.567 mmol) in NMP (6 mL) and was subjected to microwave irradiation at 150° C. for 4 h. The reaction mixture was quenched with water and extracted with EtOAc (2×). The combined organic extracts were washed with brine, dried over $Na_2SO_4$, and concentrated under reduced pressure. The crude material was absorbed onto a plug of silica gel and purified by flash column chromatography eluting with a gradient of 0% to 30% EtOAc in petroleum ether to provide 7-bromo-N-(2-(4,4-difluoropiperidin-1-yl)-6-methylpyridin-4-yl)-5-(6-azaspiro[2.5]octan-6-yl)quinazolin-4-amine (0.045 g, 0.083 mmol, 15% yield) as a pale-yellow solid. $^1$H NMR (400 MHz, DMSO-$d_6$): δ ppm 12.92 (s, 1H), 8.68 (s, 1H), 7.83 (d, J=2.0 Hz, 1H), 7.71 (d, J=1.9 Hz, 1H), 7.27 (d, J=7.6 Hz, 1H), 7.18 (s, 1H), 3.70 (s, 4H), 2.99 (t, J=12.0 Hz, 2H), 2.56 (q, J=1.9 Hz, 2H), 2.43-2.48 (m, 2H), 2.27 (s, 3H), 2.02-2.04 (s, 4H), 0.85 (s, 2H), 0.42 (d, J=8.9 Hz, 4H). m/z (ESI): 543.1/545.1 $(M+H)^+$.

Step 4: A solution of 7-bromo-N-(2-(4,4-difluoropiperidin-1-yl)-6-methylpyridin-4-yl)-5-(6-azaspiro[2.5]octan-6-yl)quinazolin-4-amine (0.04 g, 0.07 mmol), 2-hydroxyethane-1-sulfonamide (0.014 g, 0.110 mmol), potassium phosphate tribasic (0.047 g, 0.221 mmol), copper(I) iodide (0.028 g, 0.147 mmol) and (1R,2R)—N,N'-dimethyl-1,2-cyclohexanediamine (10 mg, 0.074 mmol) in DMF (2 mL) was heated at 95° C. for 16 h. The reaction mixture was filtered through a CELITE® pad and washed with EtOAc. The combined organic extracts were washed with brine, dried over $Na_2SO_4$, filtered, and evaporated under vacuum. The crude product was purified by preparative HPLC [Kinetex EVO C18 (250×21.2) mm, 5 μm, 0.1% TFA $CH_3CN/H_2O$] to afford N-(4-((2-(4,4-difluoropiperidin-1-yl)-6-methylpyridin-4-yl)amino)-5-(6-azaspiro[2.5]octan-6-yl)quinazolin-7-yl)-2-hydroxyethane-1-sulfonamide 2,2,2-trifluoroacetate (0.014 g, 0.020 mmol, 27% yield) as a yellow solid. $^1H$ NMR (400 MHz, DMSO-$d_6$): δ ppm 13.23 (s, 1H), 10.70 (s, 1H), 8.83 (s, 1H), 7.45 (q, J=2.1 Hz, 3H), 7.27 (s, 1H), 3.69-3.84 (m, 6H), 3.47 (t, J=6.2 Hz, 2H), 3.23 (d, J=10.9 Hz, 2H), 2.86 (t, J=11.5 Hz, 2H), 2.46 (dq, J=3.7, 2.1 Hz, 2H), 2.23 (t, J=11.9 Hz, 2H), 2.12-2.18 (m, 6H), 1.09 (d, J=13.3 Hz, 2H), 0.39-0.48 (m, 4H). m/z (ESI): 588.3 $(M+H)^+$.

TABLE 6

Examples 105-1 and 105-2 were prepared analogous to preparation of Example 105:

| Ex. # | Chemical Structure | Name | LRMS: (ESI + ve ion) m/z |
|---|---|---|---|
| 105-1 | 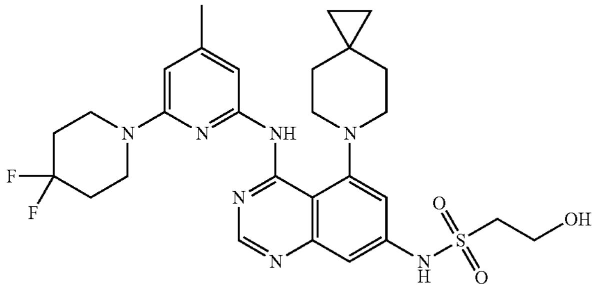 | N-(4-((6-(4,4-Difluoropiperidin-1-yl)-4-methylpyridin-2-yl)amino)-5-(6-azaspiro[2.5]octan-6-yl)quinazolin-7-yl)-2-hydroxyethane-1-sulfonamide | 588.3 |
| 105-2 | 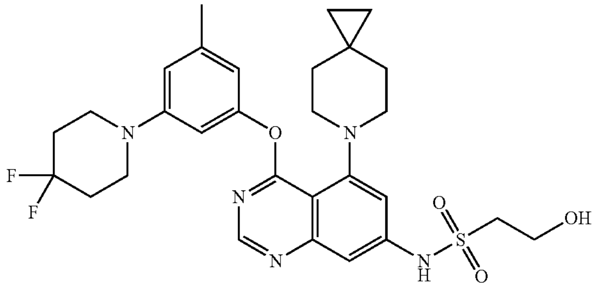 [SMILES: Cc1cc(Oc2ncnc3cc(NS(=O)(=O)CCO)cc(N4CCC5(CC4)CC5)c23)cc(N2CCC(F)(F)CC2)c1] | N-(4-(3-(4,4-Difluoropiperidin-1-yl)-5-methylphenoxy)-5-(6-azaspiro[2.5]octan-6-yl)quinazolin-7-yl)-2-hydroxyethane-1-sulfonamide | 588.2 |

Example 106: N-(1-((3-(4,4-Difluoropiperidin-1-yl)-5-methylphenyl)amino)-8-(6-azaspiro[2.5]octan-6-yl)phthalazin-6-yl)-2-hydroxyethane-1-sulfonamide

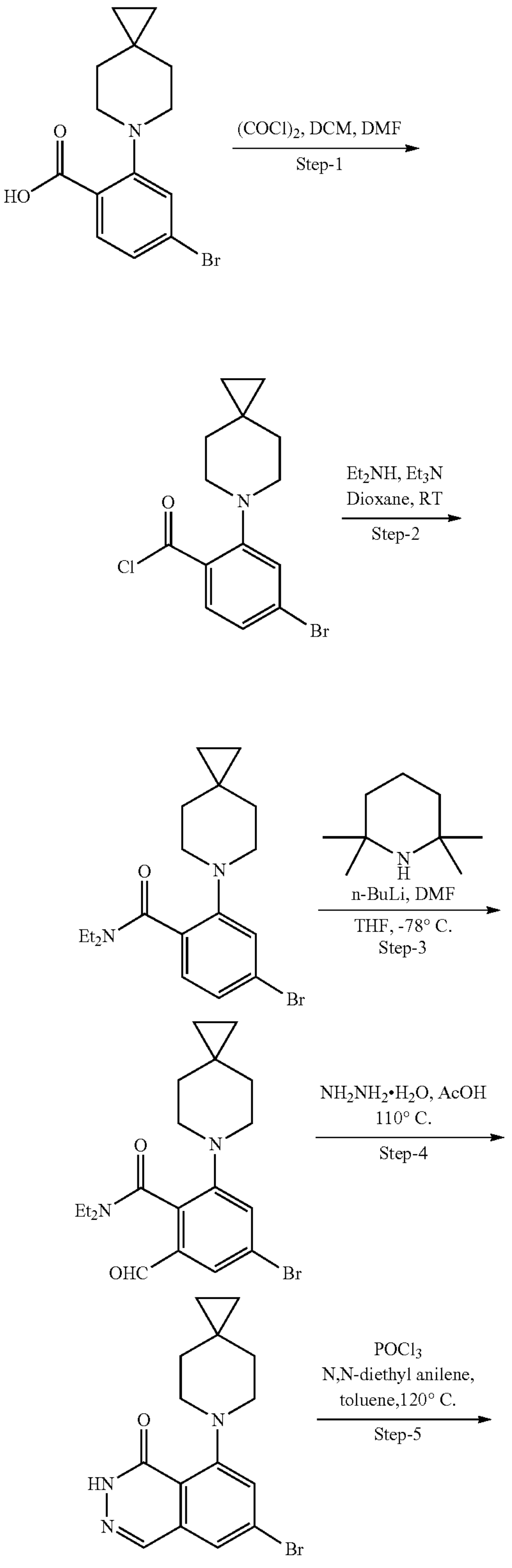

-continued

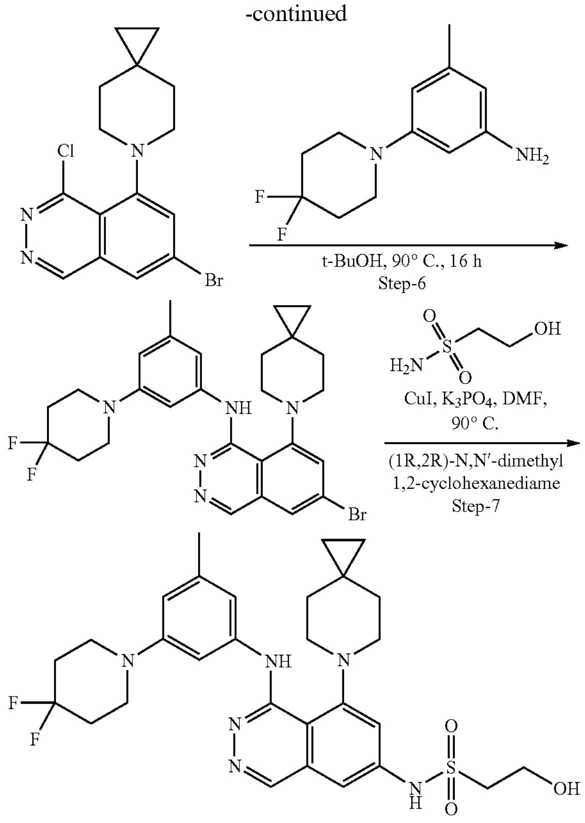

Step 1: To a solution of 4-bromo-2-(6-azaspiro[2.5]octan-6-yl)benzoic acid (4 g, 12.9 mmol) in DCM (100 mL) were added oxalyl chloride (2.26 mL, 25.8 mmol) dropwise at 0° C. followed by DMF (0.20 mL, 2.58 mmol). The reaction mixture was stirred at rt for 1 h. The reaction mixture was evaporated under reduced pressure and was co-distilled with toluene to afford crude 4-bromo-2-(6-azaspiro[2.5]octan-6-yl)benzoyl chloride (4.2 g, 12.8 mmol, 99% yield) as a yellow solid. This was taken to the next step without further purification.

Step 2: To a solution of diethylamine (1.87 g, 25.6 mmol) in dioxane (100 mL) was added $Et_3N$ (7.13 mL, 51.1 mmol) followed by 4-bromo-2-(6-azaspiro[2.5]octan-6-yl)benzoyl chloride (4.2 g, 12.8 mmol) at 0° C. The reaction mixture was stirred at rt for 16 h before it was quenched with cold water and extracted with EtOAc. The organic layer was washed with water, brine, dried over $Na_2SO_4$, filtered, and concentrated under reduced pressure to afford 4-bromo-N,N-diethyl-2-(6-azaspiro[2.5]octan-6-yl)benzamide (4.5 g, 12.3 mmol, 96% yield) as a light brown syrup. It was taken to the next step without further purification. $^1$H NMR (400 MHz, DMSO-$d_6$): δ ppm 7.21 (d, J=7.7 Hz, 2H), 7.03-7.08 (m, 1H), 3.55 (s, 3H), 3.07-3.22 (m, 3H), 2.82 (ddd, J=11.0, 7.0, 3.6 Hz, 2H), 1.32-1.48 (m, 4H), 1.17 (t, J=7.1 Hz, 3H), 0.94 (t, J=7.1 Hz, 3H), 0.31 (d, J=1.9 Hz, 4H).

Step 3: A solution of 2,2,6,6-tetramethylpiperidine (0.97 g, 6.84 mmol) in THF (20 mL) was cooled to −78° C. and treated with n-BuLi (2.5 M solution in hexanes, 2.74 mL, 6.84 mmol). The reaction mixture was stirred at the same temperature for 30 min and then a solution of 4-bromo-N,N-diethyl-2-(6-azaspiro[2.5]octan-6-yl)benzamide (1.0 g, 2.7 mmol) in THF (10 mL) was dropwise added to it. The resulting brown solution was stirred at the same temperature for 45 minutes and then DMF (1.06 mL, 13.69 mmol) was added dropwise to it at the same temperature. The reaction mixture was stirred for 1 h and quenched with an aq. satd. $NH_4Cl$ solution. The aqueous layer was extracted with EtOAc, washed with brine, dried over $Na_2SO_4$, and concentrated under reduced pressure to afford 4-bromo-N, N-diethyl-2-formyl-6-(6-azaspiro[2.5]octan-6-yl)benzamide (1.1 g crude) as a light brown gum. The crude product was taken for next step without further purification. m/z (ESI): 393.1/395.1 $(M+H)^+$.

Step 4: To a solution of 4-bromo-N, N-diethyl-2-formyl-6-(6-azaspiro[2.5]octan-6-yl)benzamide (3.4 g, 8.6 mmol) in AcOH (12 mL) was added hydrazine hydrate (0.86 g, 17.29 mmol) at rt and heated to 110° C. for 24 h. The reaction mixture was quenched with water and extracted with EtOAc. The organic layer was washed with 10% $NaHCO_3$ solution, brine, dried over $Na_2SO_4$, filtered, and concentrated under reduced pressure. The crude product was purified by flash column chromatography using 20% EtOAc in petroleum ether to afford 6-bromo-8-(6-azaspiro[2.5]octan-6-yl)phthalazin-1(2H)-one (0.5 g, 1.5 mmol, 17% yield) as a pale-yellow solid. $^1H$ NMR (400 MHz, DMSO-$d_6$): δ ppm 12.29 (s, 1H), 8.11 (s, 1H), 7.32 (d, J=1.9 Hz, 2H), 3.10-3.20 (m, 4H), 1.55 (br s, 4H), 0.34 (s, 4H). m/z (ESI): 334.1/336.1 (M)+.

Step 5: To solution of 6-bromo-8-(6-azaspiro[2.5]octan-6-yl)phthalazin-1(2H)-one (0.4 g, 1.2 mmol) in toluene (8 mL) were added phosphorus oxychloride (0.223 mL, 2.394 mmol) and N,N-diethylaniline (0.357 g, 2.394 mmol) at rt. The resulting mixture was heated at 120° C. for 2 h before it was evaporated under reduced pressure and the residue was co-distilled with toluene to afford 6-bromo-1-chloro-8-(6-azaspiro[2.5]octan-6-yl)phthalazine as a brown solid (0.6 g). The crude material taken for next step without further purification.

Step 6: A mixture of 6-bromo-1-chloro-8-(6-azaspiro[2.5]octan-6-yl)phthalazine (0.30 g, 0.85 mmol) and 3-(4,4-difluoropiperidin-1-yl)-5-methylaniline (0.385 g, 1.701 mmol) in tert-butanol (2.5 mL) was heated for 90° C. for 16 h. The reaction mixture was concentrated under reduced pressure and purified by preparative HPLC purification [Kinetex EVO C-18 (250×21.2) mm, 5 μm, 0.1% TFA in $CH_3CN/H_2O$] to afford 6-bromo-N-(3-(4,4-difluoropiperidin-1-yl)-5-methylphenyl)-8-(6-azaspiro[2.5]octan-6-yl)phthalazin-1-amine (0.06 g, 0.11 mmol, 13% yield) as a light brown solid. $^1H$ NMR (400 MHz, DMSO-$d_6$): δ ppm 13.34 (s, 1H), 8.99 (s, 1H), 8.34 (q, J=1.9 Hz, 2H), 7.05 (s, 1H), 6.93 (s, 1H), 6.89 (s, 1H), 3.43 (t, J=5.7 Hz, 4H), 3.27 (d, J=11.4 Hz, 2H), 3.10 (t, J=11.4 Hz, 2H), 2.34 (s, 3H), 2.08-2.15 (m, 6H), 1.07 (d, J=13.5 Hz, 2H), 0.40 (s, 4H). m/z (ESI): 542.1/544.1 (M)+.

Step 7: A mixture of 6-bromo-N-(3-(4,4-difluoropiperidin-1-yl)-5-methylphenyl)-8-(6-azaspiro[2.5]octan-6-yl)phthalazin-1-amine (0.06 g, 0.111 mmol), 2-hydroxyethane-1-sulfonamide (0.021 g, 0.166 mmol), potassium phosphate tribasic (0.047 g, 0.221 mmol), copper(I) iodide (0.021 g, 0.111 mmol) and (1R,2R)—N,N-dimethyl-1,2-cyclohexanediamine (8 mg, 0.055 mmol) in DMF (2 mL) was heated at 95° C. for 16 h. The reaction mixture was filtered through a CELITE® bed and washed with EtOAc. The organic layer was washed with brine, dried over $Na_2SO_4$, filtered, and concentrated under reduced pressure. The crude product was purified by preparative HPLC [Kinetex EVO C-18 (250×21.2) mm, 5 μm, 0.1% TFA in $CH_3CN/H_2O$] to afford N-(1-((3-(4,4-difluoropiperidin-1-yl)-5-methylphenyl)amino)-8-(6-azaspiro[2.5]octan-6-yl)phthalazin-6-yl)-2-hydroxyethane-1-sulfonamide as a white solid. $^1H$ NMR (400 MHz, DMSO-$d_6$): δ ppm 12.97 (s, 1H), 10.93 (s, 1H), 9.05 (s, 1H), 7.72-7.78 (m, 2H), 7.03 (t, J=2.1 Hz, 1H), 6.89 (d, J=14.3 Hz, 2H), 3.82 (t, J=6.1 Hz, 3H), 3.55 (t, J=6.1 Hz, 2H), 3.43 (d, J=11.5 Hz, 4H), 3.31 (d, J=11.1 Hz, 2H), 2.84-2.95 (m, 2H), 2.34 (s, 3H), 1.99-2.12 (m, 6H), 1.09 (d, J=13.2 Hz, 2H), 0.36-0.46 (m, 4H). m/z (ESI): 587.2 $(M+H)^+$.

Additional Examples

The following Examples 107-140 can be made according to the procedure similar to the above examples by using starting commercially available materials or can be made according to procedure familiar to those skilled in the art.

| Ex. # | Chemical Structure | Name |
|---|---|---|
| 107 | 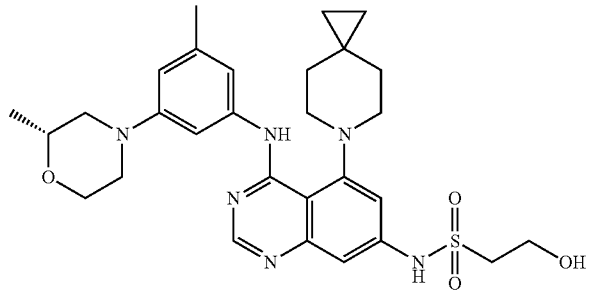 [SMILES: Cc1cc(Nc2ncnc3cc(NS(=O)(=O)CCO)cc(N4CCC5(CC4)CC5)c23)cc(N2CCO[C@H](C)C2)c1] | (R)-2-Hydroxy-N-(4-((3-methyl-5-(2-methylmorpholino)phenyl)amino)-5-(6-azaspiro[2.5]octan-6-yl)quinazolin-7-yl)ethane-1-sulfonamide |
| 108 | 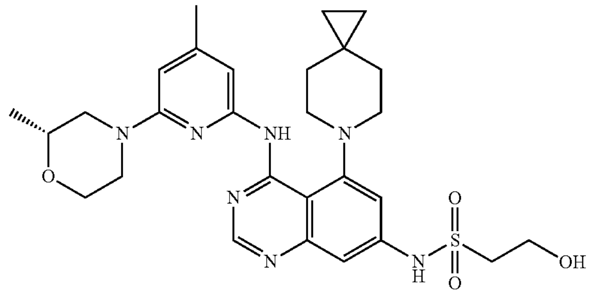 [SMILES: Cc1cc(Nc2ncnc3cc(NS(=O)(=O)CCO)cc(N4CCC5(CC4)CC5)c23)nc(N2CCO[C@H](C)C2)c1] | (R)-2-Hydroxy-N-(4-((4-methyl-6-(2-methylmorpholino)pyridin-2-yl)amino)-5-(6-azaspiro[2.5]octan-6-yl)quinazolin-7-yl)ethane-1-sulfonamide |

-continued

| Ex. # | Chemical Structure | Name |
|---|---|---|
| 109 | 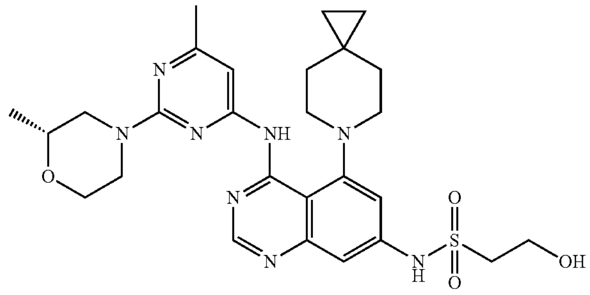 [SMILES: Cc1cc(Nc2ncnc3cc(NS(=O)(=O)CCO)cc(N4CCC5(CC4)CC5)c23)nc(N2CCO[C@H](C)C2)n1] | (R)-2-Hydroxy-N-(4-((6-methyl-2-(2-methylmorpholino)pyrimidin-4-yl) amino)-5-(6-azaspiro[2.5]octan-6-yl) quinazolin-7-yl)ethane-1-sulfonamide |
| 110 | 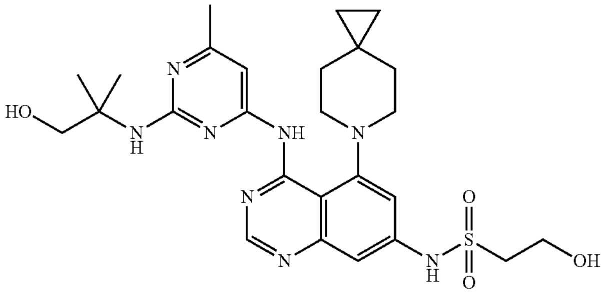 [SMILES: Cc1cc(Nc2ncnc3cc(NS(=O)(=O)CCO)cc(N4CCC5(CC4)CC5)c23)nc(NC(C)(C)CO)n1] | 2-Hydroxy-N-(4-((2-((1-hydroxy-2-methylpropan-2-yl)amino)-6-methylpyrimidin-4-yl)amino)-5-(6-azaspiro[2.5]octan-6-yl)quinazolin-7-yl)ethane-1-sulfonamide |
| 111 | 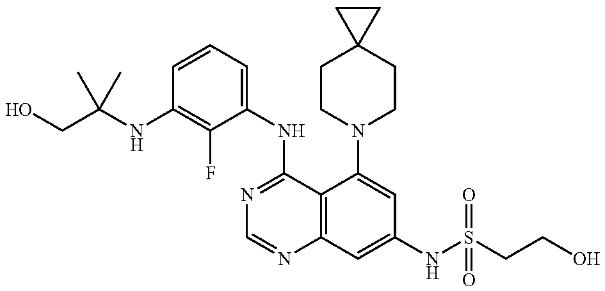 [SMILES: CC(C)(CO)Nc1cccc(Nc2ncnc3cc(NS(=O)(=O)CCO)cc(N4CCC5(CC4)CC5)c23)c1F] | N-(4-((2-Fluoro-3-((1-hydroxy-2-methylpropan-2-yl)amino)phenyl) amino)-5-(6-azaspiro[2.5]octan-6-yl)quinazolin-7-yl)-2-hydroxyethane-1-sulfonamide |
| 112 | 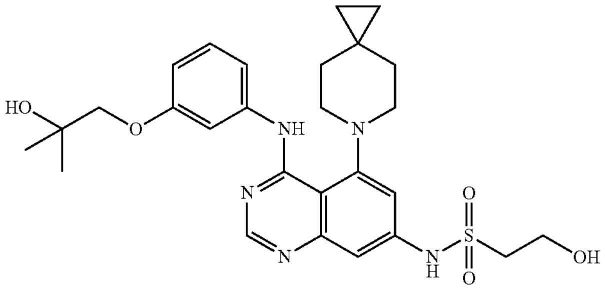 [SMILES: CC(C)(O)COc1cccc(Nc2ncnc3cc(NS(=O)(=O)CCO)cc(N4CCC5(CC4)CC5)c23)c1] | 2-Hydroxy-N-(4-((3-(2-hydroxy-2-methylpropoxy)phenyl)amino)-5-(6-azaspiro[2.5]octan-6-yl)quinazolin-7-yl)ethane-1-sulfonamide |
| 113 | 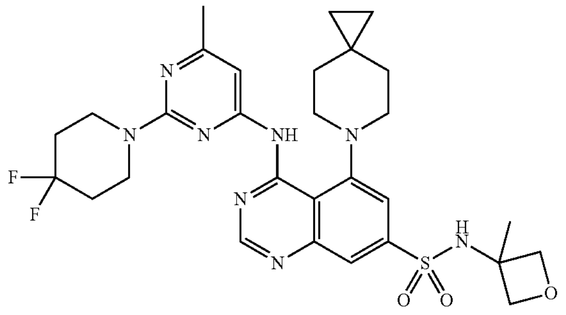 [SMILES: Cc1cc(Nc2ncnc3cc(S(=O)(=O)NC4(C)COC4)cc(N4CCC5(CC4)CC5)c23)nc(N2CCC(F)(F)CC2)n1] | 4-((2-(4,4-Difluoropiperidin-1-yl)-6-methylpyrimidin-4-yl)amino)-N-(3-methyloxetan-3-yl)-5-(6-azaspiro[2.5] octan-6-yl)quinazoline-7-sulfonamide |

-continued

| Ex. # | Chemical Structure | Name |
|---|---|---|
| 114 | 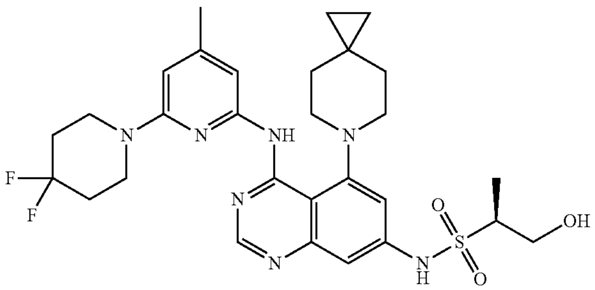 [SMILES: Cc1cc(Nc2ncnc3cc(NS(=O)(=O)[C@@H](C)CO)cc(N4CCC5(CC4)CC5)c23)nc(N2CCC(F)(F)CC2)c1] | (S)-N-(4-((6-(4,4-Difluoropiperidin-1-yl)-4-methylpyridin-2-yl)amino)-5-(6-azaspiro[2.5]octan-6-yl)quinazolin-7-yl)-1-hydroxypropane-2-sulfonamide |
| 115 | 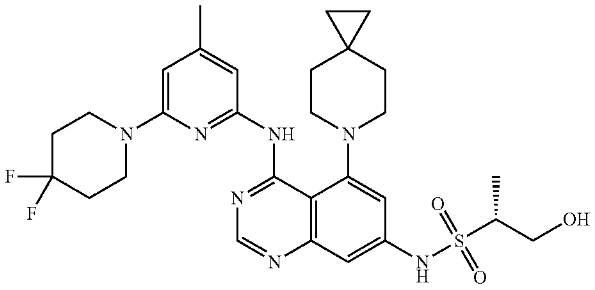 [SMILES: Cc1cc(Nc2ncnc3cc(NS(=O)(=O)[C@H](C)CO)cc(N4CCC5(CC4)CC5)c23)nc(N2CCC(F)(F)CC2)c1] | (R)-N-(4-((6-(4,4-Difluoropiperidin-1-yl)-4-methylpyridin-2-yl)amino)-5-(6-azaspiro[2.5]octan-6-yl)quinazolin-7-yl)-1-hydroxypropane-2-sulfonamide |
| 116 | 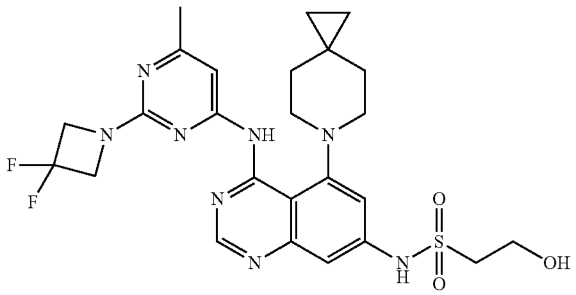 [SMILES: Cc1cc(Nc2ncnc3cc(NS(=O)(=O)CCO)cc(N4CCC5(CC4)CC5)c23)nc(N2CC(F)(F)C2)n1] | N-(4-((2-(3,3-Difluoroazetidin-1-yl)-6-methylpyrimidin-4-yl)amino)-5-(6-azaspiro[2.5]octan-6-yl)quinazolin-7-yl)-2-hydroxyethane-1-sulfonamide |
| 117 | 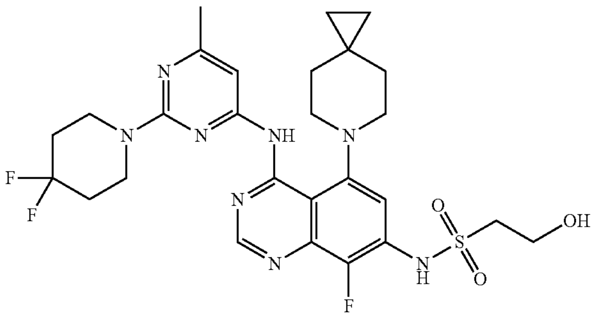 [SMILES: Cc1cc(Nc2ncnc3c(F)c(NS(=O)(=O)CCO)cc(N4CCC5(CC4)CC5)c23)nc(N2CCC(F)(F)CC2)n1] | N-(4-((2-(4,4-Difluoropiperidin-1-yl)-6-methylpyrimidin-4-yl)amino)-8-fluoro-5-(6-azaspiro[2.5]octan-6-yl)quinazolin-7-yl)-2-hydroxyethane-1-sulfonamide |
| 118 | 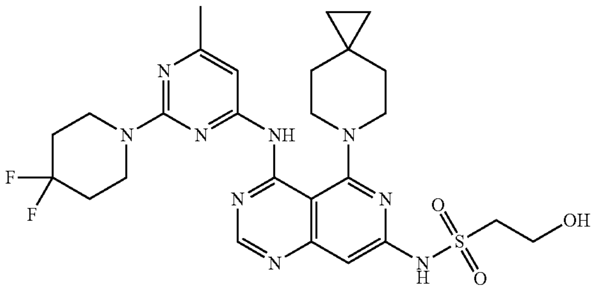 [SMILES: Cc1cc(Nc2ncnc3cc(NS(=O)(=O)CCO)nc(N4CCC5(CC4)CC5)c23)nc(N2CCC(F)(F)CC2)n1] | N-(4-((2-(4,4-Difluoropiperidin-1-yl)-6-methylpyrimidin-4-yl)amino)-5-(6-azaspiro[2.5]octan-6-yl)pyrido[4,3-d]pyrimidin-7-yl)-2-hydroxyethane-1-sulfonamide |

-continued

| Ex. # | Chemical Structure | Name |
| --- | --- | --- |
| 119 | 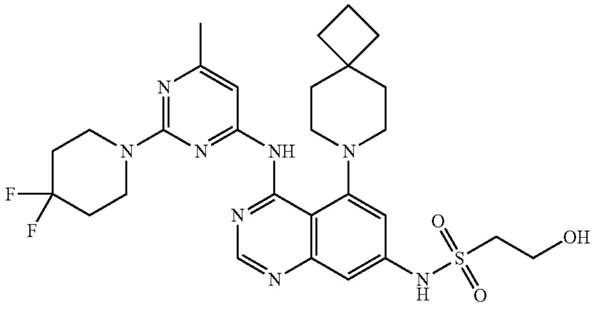 [SMILES: Cc1cc(Nc2ncnc3cc(NS(=O)(=O)CCO)cc(N4CCC5(CCC5)CC4)c23)nc(N2CCC(F)(F)CC2)n1] | N-(4-((2-(4,4-Difluoropiperidin-1-yl)-6-methylpyrimidin-4-yl)amino)-5-(7-azaspiro[3.5]nonan-7-yl)quinazolin-7-yl)-2-hydroxyethane-1-sulfonamide |
| 120 | 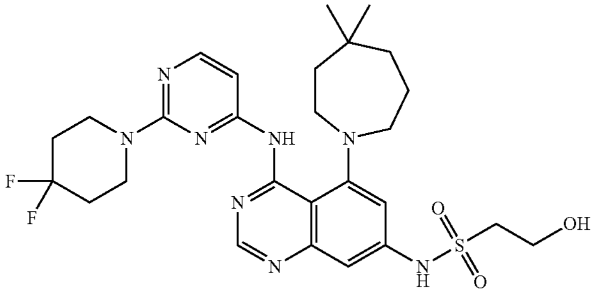 [SMILES: CC1(C)CCCN(c2cc(NS(=O)(=O)CCO)cc3ncnc(Nc4ccnc(N5CCC(F)(F)CC5)n4)c23)CC1] | N-(4-((2-(4,4-Difluoropiperidin-1-yl)pyrimidin-4-yl)amino)-5-(4,4-dimethylazepan-1-yl)quinazolin-7-yl)-2-hydroxyethane-1-sulfonamide |
| 121 | 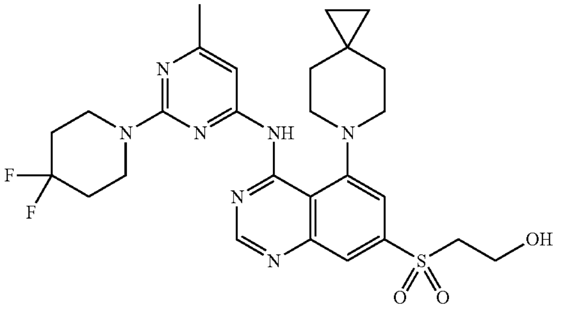 [SMILES: Cc1cc(Nc2ncnc3cc(S(=O)(=O)CCO)cc(N4CCC5(CC4)CC5)c23)nc(N2CCC(F)(F)CC2)n1] | 2-((4-((2-(4,4-Difluoropiperidin-1-yl)-6-methylpyrimidin-4-yl)amino)-5-(6-azaspiro[2.5]octan-6-yl)quinazolin-7-yl)sulfonyl)ethan-1-ol |
| 122 | 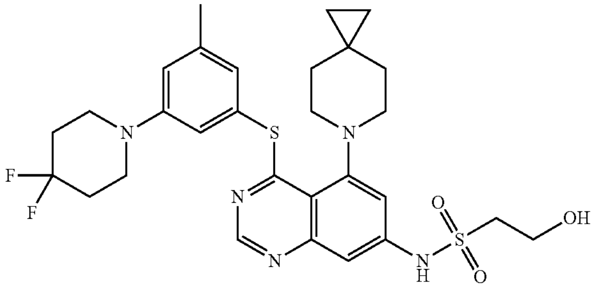 | N-(4-((3-(4,4-Difluoropiperidin-1-yl)-5-methylphenyl)thio)-5-(6-azaspiro[2.5]octan-6-yl)quinazolin-7-yl)-2-hydroxyethane-1-sulfonamide |
| 123 | 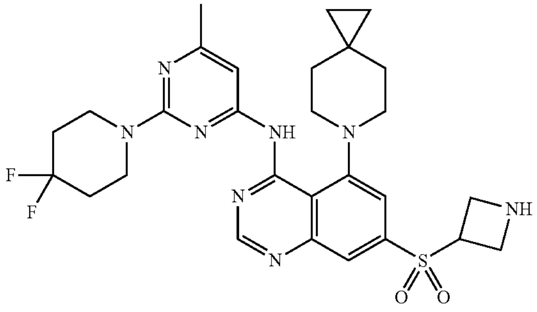 [SMILES: Cc1cc(Nc2ncnc3cc(S(=O)(=O)C4CNC4)cc(N4CCC5(CC4)CC5)c23)nc(N2CCC(F)(F)CC2)n1] | 7-(Azetidin-3-ylsulfonyl)-N-(2-(4,4-difluoropiperidin-1-yl)-6-methylpyrimidin-4-yl)-5-(6-azaspiro[2.5]octan-6-yl)quinazolin-4-amine |

-continued

| Ex. # | Chemical Structure | Name |
| --- | --- | --- |
| 124 | 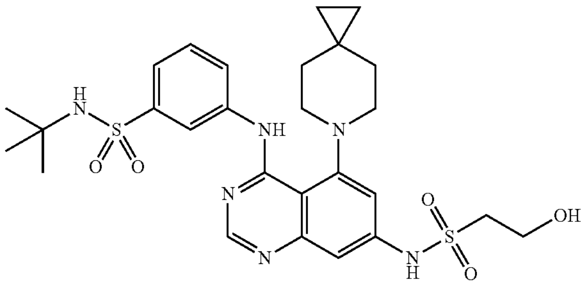 [SMILES: CC(C)(C)NS(=O)(=O)c1cccc(Nc2ncnc3cc(NS(=O)(=O)CCO)cc(N4CCC5(CC4)CC5)c23)c1] | N-(tert-Butyl)-3-((7-((2-hydroxyethyl)sulfonamido)-5-(6-azaspiro[2.5]octan-6-yl)quinazolin-4-yl)amino)benzenesulfonamide |
| 125 | 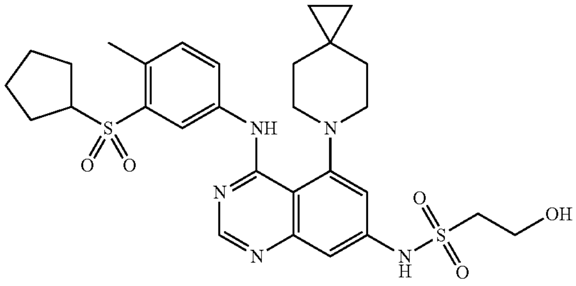 [SMILES: Cc1ccc(Nc2ncnc3cc(NS(=O)(=O)CCO)cc(N4CCC5(CC4)CC5)c23)cc1S(=O)(=O)C1CCCC1] | N-(4-((3-(Cyclopentylsulfonyl)-4-methylphenyl)amino)-5-(6-azaspiro[2.5]octan-6-yl)quinazolin-7-yl)-2-hydroxyethane-1-sulfonamide |
| 126 | 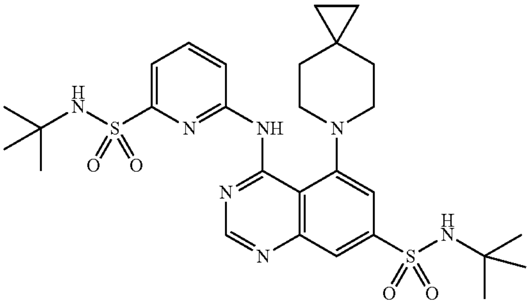 [SMILES: CC(C)(C)NS(=O)(=O)c1cc(N2CCC3(CC2)CC3)c2c(Nc3cccc(S(=O)(=O)NC(C)(C)C)n3)ncnc2c1] | N-(tert-Butyl)-4-((6-(N-(tert-butyl)sulfamoyl)pyridin-2-yl)amino)-5-(6-azaspiro[2.5]octan-6-yl) quinazoline-7-sulfonamide |
| 127 | 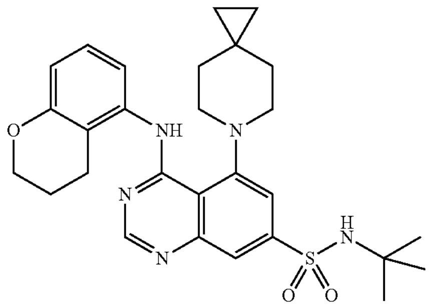 [SMILES: CC(C)(C)NS(=O)(=O)c1cc(N2CCC3(CC2)CC3)c2c(Nc3cccc4c3CCCO4)ncnc2c1] | N-(tert-Butyl)-4-(chroman-5-ylamino)-5-(6-azaspiro[2.5]octan-6-yl) quinazoline-7-sulfonamide |
| 128 | 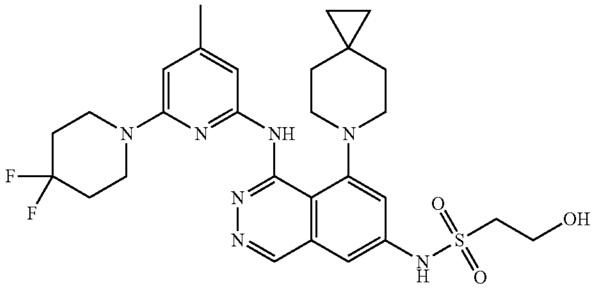 | N-(1-((6-(4,4-Difluoropiperidin-1-yl)-4-methylpyridin-2-yl)amino)-8-(6-azaspiro[2.5]octan-6-yl)phthalazin-6-yl)-2-hydroxyethane-1-sulfonamide |

-continued

| Ex. # | Chemical Structure | Name |
| --- | --- | --- |
| 129 | 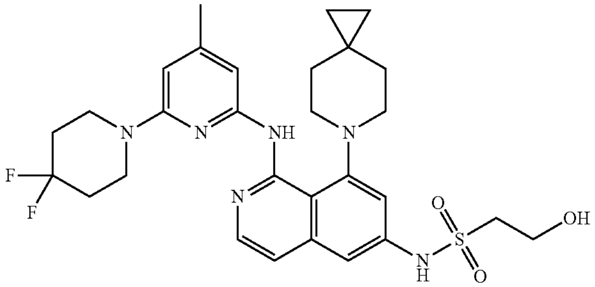 | N-(1-((6-(4,4-Difluoropiperidin-1-yl)-4-methylpyridin-2-yl)amino)-8-(6-azaspiro[2.5]octan-6-yl)isoquinolin-6-yl)-2-hydroxyethane-1-sulfonamide |
| 130 | 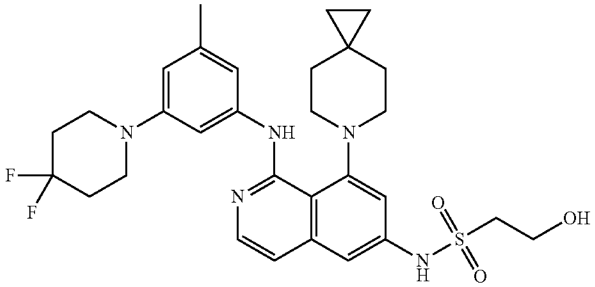 | N-(1-((3-(4,4-Difluoropiperidin-1-yl)-5-methylphenyl)amino)-8-(6-azaspiro[2.5]octan-6-yl)isoquinolin-6-yl)-2-hydroxyethane-1-sulfonamide |
| 131 | 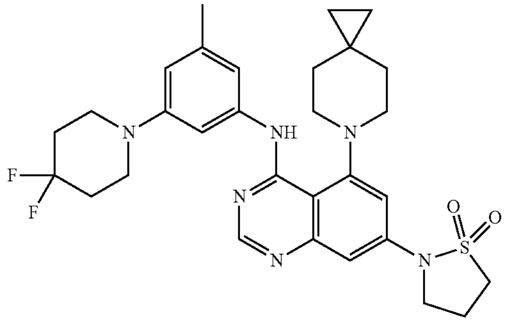 [SMILES: Cc1cc(Nc2ncnc3cc(N4CCCS4(=O)=O)cc(N4CCC5(CC4)CC5)c23)cc(N2CCC(F)(F)CC2)c1] | 2-(4-((3-(4,4-Difluoropiperidin-1-yl)-5-methylphenyl)amino)-5-(6-azaspiro[2.5]octan-6-yl)quinazolin-7-yl)isothiazolidine 1,1-dioxide |
| 132 | 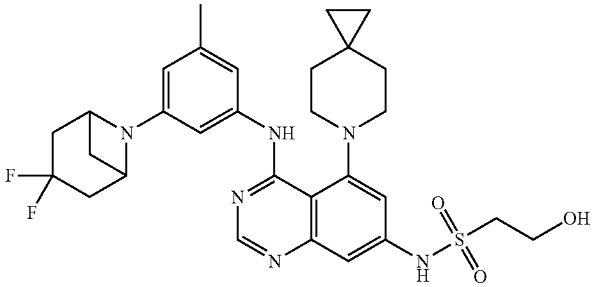 [SMILES: Cc1cc(Nc2ncnc3cc(NS(=O)(=O)CCO)cc(N4CCC5(CC4)CC5)c23)cc(N2C3CC2CC(F)(F)C3)c1] | N-(4-((3-(3,3-Difluoro-6-azabicyclo[3.1.1]heptan-6-yl)-5-methylphenyl)amino)-5-(6-azaspiro[2.5]octan-6-yl)quinazolin-7-yl)-2-hydroxyethane-1-sulfonamide |
| 133 | 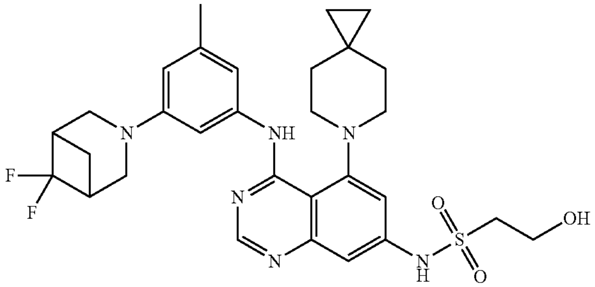 [SMILES: Cc1cc(Nc2ncnc3cc(NS(=O)(=O)CCO)cc(N4CCC5(CC4)CC5)c23)cc(N2CC3CC(C2)C3(F)F)c1] | N-(4-((3-(6,6-Difluoro-3-azabicyclo[3.1.1]heptan-3-yl)-5-methylphenyl)amino)-5-(6-azaspiro[2.5]octan-6-yl)quinazolin-7-yl)-2-hydroxyethane-1-sulfonamide |

-continued

| Ex. # | Chemical Structure | Name |
|---|---|---|
| 134 | 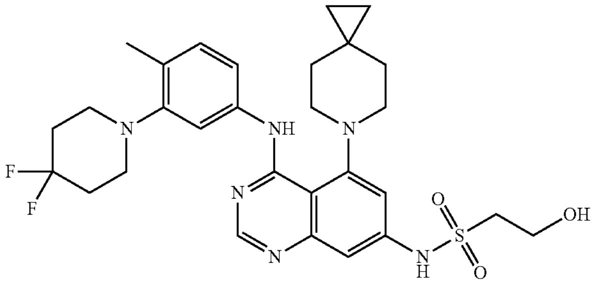 [SMILES: Cc1ccc(Nc2ncnc3cc(NS(=O)(=O)CCO)cc(N4CCC5(CC4)CC5)c23)cc1N1CCC(F)(F)CC1] | N-(4-((3-(4,4-Difluoropiperidin-1-yl)-4-methylphenyl)amino)-5-(6-azaspiro[2.5]octan-6-yl)quinazolin-7-yl)-2-hydroxyethane-1-sulfonamide |
| 135 | 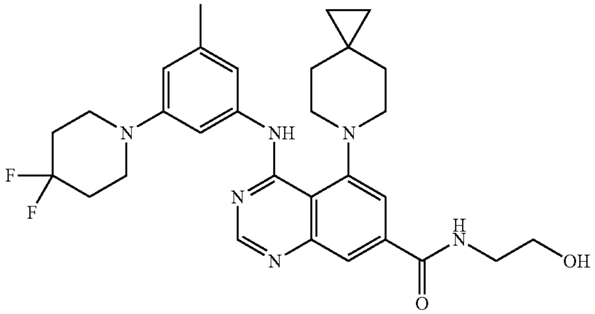 [SMILES: Cc1cc(Nc2ncnc3cc(C(=O)NCCO)cc(N4CCC5(CC4)CC5)c23)cc(N2CCC(F)(F)CC2)c1] | 4-((3-(4,4-Difluoropiperidin-1-yl)-5-methylphenyl)amino)-N-(2-hydroxyethyl)-5-(6-azaspiro[2.5]octan-6-yl)quinazoline-7-carboxamide |
| 136 | 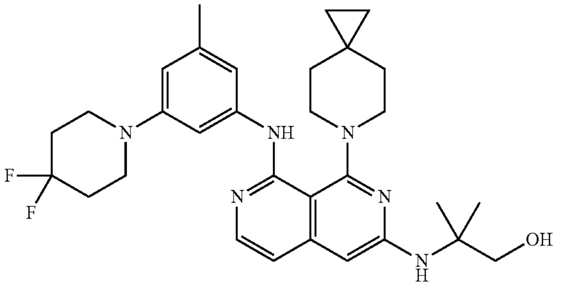 [SMILES: Cc1cc(Nc2nccc3cc(NC(C)(C)CO)nc(N4CCC5(CC4)CC5)c23)cc(N2CCC(F)(F)CC2)c1] | 2-((8-((3-(4,4-Difluoropiperidin-1-yl)-5-methylphenyl)amino)-1-(6-azaspiro[2.5]octan-6-yl)-2,7-naphthyridin-3-yl)amino)-2-methylpropan-1-ol |
| 137 | 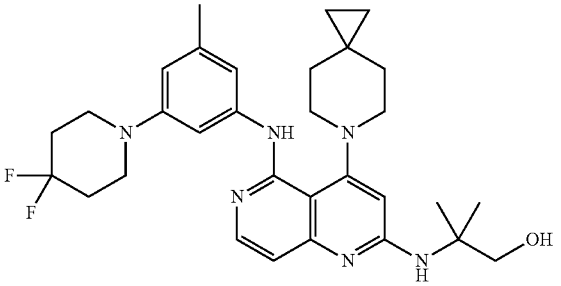 [SMILES: Cc1cc(Nc2nccc3nc(NC(C)(C)CO)cc(N4CCC5(CC4)CC5)c23)cc(N2CCC(F)(F)CC2)c1] | 2-((5-((3-(4,4-Difluoropiperidin-1-yl)-5-methylphenyl)amino)-4-(6-azaspiro[2,5]octan-6-yl)-1,6-naphthyridin-2-yl)amino)-2-methylpropan-1-ol |
| 138 | 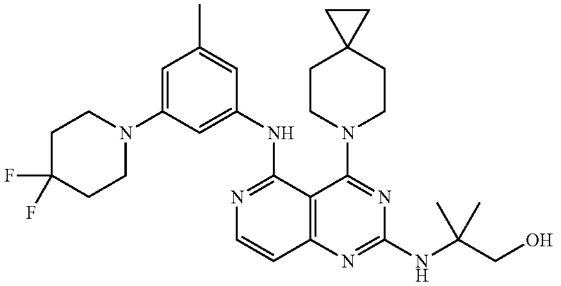 [SMILES: Cc1cc(Nc2nccc3nc(NC(C)(C)CO)nc(N4CCC5(CC4)CC5)c23)cc(N2CCC(F)(F)CC2)c1] | 2-((5-((3-(4,4-Difluoropiperidin-1-yl)-5-methylphenyl)amino)-4-(6-azaspiro[2.5]octan-6-yl)pyrido[4,3-d]pyrimidin-2-yl)amino)-2-methylpropan-1-ol |

-continued

| Ex. # | Chemical Structure | Name |
|---|---|---|
| 139 | 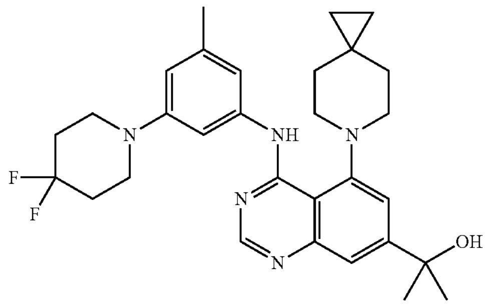 [SMILES: Cc1cc(Nc2ncnc3cc(C(C)(C)O)cc(N4CCC5(CC4)CC5)c23)cc(N2CCC(F)(F)CC2)c1] | 2-(4-((3-(4,4-Difluoropiperidin-1-yl)-5-methylphenyl)amino)-5-(6-azaspiro[2.5]octan-6-yl)quinazolin-7-yl)propan-2-ol |
| 140 | 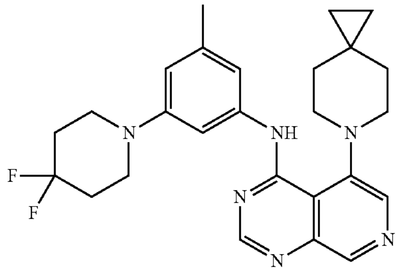 [SMILES: Cc1cc(Nc2ncnc3cncc(N4CCC5(CC4)CC5)c23)cc(N2CCC(F)(F)CC2)c1] | N-(3-(4,4-Difluoropiperidin-1-yl)-5-methylphenyl)-5-(6-azaspiro[2.5]octan-6-yl)pyrido[3,4-d]pyrimidin-4-amine |

Biological Examples

The following assays were used in testing the exemplary compounds of the invention. Data for those examples tested in accordance with the procedures described below are presented in Table A below.

KIF18A Enzyme Assay: Microtubule-stimulated ATPase activity assay is used to measure KIF18A enzyme activity after treatment with compound. Compounds were 2-fold serially diluted in DMSO (Sigma Inc) over 22-point concentration range. Recombinant human KIF18A (1-467 His-tagged) protein was expressed using a baculovirus system and purified by affinity chromatography by Amgen Inc. Concentrations of KIF18A protein, microtubules (MT), and ATP in the reaction were optimized for standardized homogenous enzyme assay using ADP-Glo™ Kinase/ATPase Assay Kit (Promega Inc). The assay measures ADP formed from the ATPase reaction. Prepare reaction buffer [(15 mM Tris, pH 7.5 (Teknova Inc), 10 mM MgCl2 (IT Baker Inc), 0.01% Pluronic F-68 (Life Technologies Inc), 1 μM Taxol (Cytoskeleton Inc), and 30 μg/mL pig microtubules (Cytoskeleton Inc)]. Add compound and KIF18A protein (30 nM) to prepared reaction buffer and incubated for 15 minutes at room temperature, next add ATP (at Kin, 75 μM) to the reaction mixture and incubated for an additional 15 minutes at room temperature. Mix 5 μl of ADP-Glor™ Reagent and 2.5 μl of the reaction mixture and incubate for 40 minutes at room temperature. Add 10 μl ADP-Glorh Detection Reagent and incubate for 40 minutes at room temperature. Read luminescence using EnVision microplate reader with ultra-luminescence module (Perkin Elmer Inc). Concentration-response curve-fitting and $IC_{50}$ determination was performed using Genedata Screener Software (Standard 15.0.1, Genedata Inc) with a four-parameter logistic regression fit model.

Table A provides data for compounds exemplified in the present application and priority document thereof, as representative compounds of the present invention, as follows: chemical name (as named by either ACD software or ChemDraw (Professional 15.0)) and biological data ($IC_{50}$ in μM). Ex. # refers to Example No.

TABLE A

BIOLOGICAL DATA

| Ex. # | Compound Name | KIF18A ATPase $IC_{50}$ (μM) |
|---|---|---|
| 100 | N-(4-((3-(4,4-Difluoropiperidin-1-yl)-5-methylphenyl)amino)-5-(6-azaspiro[2.5]octan-6-yl)quinazolin-7-yl)-2-hydroxyethane-1-sulfonamide | 0.049 |
| 100-1 | N-(4-((3-(4,4-Difluoropiperidin-1-yl)-5-methylphenyl)amino)-2-methyl-5-(6-azaspiro[2.5]octan-6-yl)quinazolin-7-yl)-2-hydroxyethane-1-sulfonamide | 0.955 |
| 101 | N-(3-(4,4-Difluoropiperidin-1-yl)-5-methylphenyl)-7-(methylsulfonyl)-5-(6-azaspiro[2.5]octan-6-yl)quinazolin-4-amine | 0.940 |
| 101-1 | N-(3-(4,4-Difluoropiperidin-1-yl)-5-methylphenyl)-5-(6-azaspiro[2.5]octan-6-yl)quinazolin-4-amine | 3.340 |
| 102-1 | (R)-Cyclopropyl(4-((3-(4,4-difluoropiperidin-1-yl)-5-methylphenyl)amino)-5-(6-azaspiro[2.5]octan-6-yl)quinazolin-7-yl)(imino)-l6-sulfanone | 0.073 |
| 102-2 | (S)-Cyclopropyl(4-((3-(4,4-difluoropiperidin-1-yl)-5-methylphenyl)amino)-5-(6-azaspiro[2.5]octan-6-yl)quinazolin-7-yl)(imino)-l6-sulfanone | 0.262 |
| 103 | 2-Hydroxy-N-(4-((3-methyl-5-(3,3,3-trifluoropropoxy)phenyl)amino)-5-(6-azaspiro[2.5]octan-6-yl)quinazolin-7-yl)ethane-1-sulfonamide | 0.175 |
| 103-1 | N-(4-((3,5-Dimethylphenyl)amino)-5-(6-azaspiro[2.5]octan-6-yl)quinazolin-7-yl)-2-hydroxyethane-1-sulfonamide | 0.403 |
| 103-2 | N-(5-(6-Azaspiro[2.5]octan-6-yl)-4-((3-(3,3,3-trifluoropropoxy)phenyl)amino)quinazolin-7-yl)-2-hydroxyethane-1-sulfonamide | 0.061 |
| 104 | N-(4-((2-(4,4-Difluoropiperidin-1-yl)-6-methylpyrimidin-4-yl)amino)-5-(6-azaspiro[2.5]octan-6-yl)quinazolin-7-yl)-2-hydroxyethane-1-sulfonamide | 0.129 |
| 105 | N-(4-((2-(4,4-Difluoropiperidin-1-yl)-6-methylpyridin-4-yl)amino)-5-(6-azaspiro[2.5]octan-6-yl)quinazolin-7-yl)-2-hydroxyethane-1-sulfonamide | 0.082 |

TABLE A-continued

| BIOLOGICAL DATA | | |
|---|---|---|
| Ex. # | Compound Name | KIF18A ATPase $IC_{50}$ (μM) |
| 105-1 | N-(4-((6-(4,4-Difluoropiperidin-1-yl)-4-methylpyridin-2-yl)amino)-5-(6-azaspiro[2.5]octan-6-yl)quinazolin-7-yl)-2-hydroxyethane-1-sulfonamide | 0.078 |
| 105-2 | N-(4-(3-(4,4-Difluoropiperidin-1-yl)-5-methylphenoxy)-5-(6-azaspiro[2.5]octan-6-yl)quinazolin-7-yl)-2-hydroxyethane-1-sulfonamide | 2.84 |
| 106 | N-(1-((3-(4,4-Difluoropiperidin-1-yl)-5-methylphenyl)amino)-8-(6-azaspiro[2.5]octan-6-yl)phthalazin-6-yl)-2-hydroxyethane-1-sulfonamide | 0.025 |

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited herein are hereby incorporated by reference in their entirety for all purposes to the same extent as if each individual patent, patent application or publication were so individually denoted.

We claim:

1. A compound of formula I:

(I)

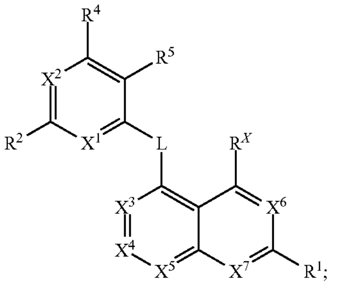

or any pharmaceutically-acceptable salt thereof, wherein:

$X^1$ is N or $CR^6$;

$X^2$ is N or $CR^{3a}$;

$X^3$ is N or $CR^{3b}$;

$X^4$ is N or $CR^{3c}$;

$X^5$ is N or $CR^{3d}$;

$X^6$ is N or $CR^{3e}$;

$X^7$ is N or $CR^{3f}$;

wherein no more than 3 of $X^3$, $X^4$, $X^5$ and $X^6$ are N;

$R^1$ is —CN, or a group —Z—$R^8$ wherein Z is —$C_{0-4}$alk-, —$NR^7$—, —$NR^7SO_2$—, —$SO_2NR^7$—, —N═S(═O)—$(R^7)_2$ (wherein the two $R^7$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S), —$NR^7$—S(═O)(═NH), —S(═O)(═NH)—, —S—, —S(═O)—, —$SO_2$—, $C_{0-4}$alk-O—, —(C═O)—, —(C═O)$NR^7$—, —C═N(OH)—, or —$NR^7$(C═O);

$R^2$ is halo or a group —Y—$R^9$, wherein Y is —$C_{0-4}$alk-, —$NR^a$—, —N($C_{1-4}$alk)-, —NH—$(CH_2)_{0-4}$—, —C(═O)$NR^a$($C_{1-4}$alk), —O—$(CH_2)_{0-4}$, $C_{0-4}$alk-S—, $C_{0-4}$alk-S═O, $C_{0-4}$alk-S(═O)$_2$, —$SO_2NR^a$—$C_{0-4}$alk-, —$C_{0-4}$alk-S(═O)(═NH)—, —O—$C_{0-4}$alk-, —$C_{0-4}$alk-(C═O)—, or —$C_{0-4}$alk-(C═O)—O—;

L is —$NR^3$, —O—, —S—, S═O, or S(═O)$_2$;

$R^3$ is H, $C_{1-4}$alk, or $C_{1-4}$haloalk;

$R^{3a}$ is H, halo, $C_{1-8}$alk, or $C_{1-4}$haloalk;

$R^{3b}$ is H, halo, $C_{1-8}$alk, or $C_{1-4}$haloalk;

$R^{3c}$ is H, halo, $C_{1-8}$alk, or $C_{1-4}$haloalk;

$R^{3d}$ is H, halo, $C_{1-8}$alk, or $C_{1-4}$haloalk;

$R^{3e}$ is H, halo, $C_{1-8}$alk, or $C_{1-4}$haloalk;

$R^{3f}$ is H, halo, $C_{1-8}$alk, or $C_{1-4}$haloalk;

$R^4$ is H, halo, $R^{4a}$ or $R^{4b}$;

$R^5$ is H, halo, $C_{1-8}$alk, or $C_{1-4}$haloalk;

$R^6$ is H, halo, $C_{1-8}$alk, $C_{1-4}$haloalk, —O—$C_{1-8}$alk, or —O—$R^{6a}$; wherein $R^{6a}$ is a saturated or partially-saturated 3-, 4-, 5-, or 6-membered monocyclic ring containing 0, 1, 2 or 3 N atoms and 0, 1, or 2 atoms selected from O and S;

$R^X$ is

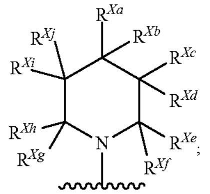

Each of $R^{Xa}$, $R^{Xb}$, $R^{Xc}$, $R^{Xd}$, $R^{Xe}$, $R^{Xf}$, $R^{Xg}$, $R^{Xh}$, $R^{Xi}$, and $R^{Xj}$ is H, halo, $R^{Xm}$, or $R^{Xn}$;

or alternatively, each of $R^{Xa}$ and $R^{Xb}$ pair, $R^{Xc}$ and $R^{Xd}$ pair, $R^{Xe}$ and $R^{Xf}$ pair, $R^{Xg}$ and $R^{Xh}$ pair, $R^{Xi}$ and $R^{Xj}$ pair, independently, can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains O N, O, and S atoms, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, —$OR^a$, —$OC_{1-4}$haloalk, CN, —$NR^aR^a$, or oxo;

$R^7$ is H, $R^{7a}$, or $R^{7b}$;

$R^8$ is H, $R^{8a}$, or $R^{8b}$;

$R^9$ is $R^{9a}$ or $R^{9b}$;

$R^{4a}$, $R^{Xm}$, $R^{7a}$, $R^{8a}$, and $R^{9a}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0, 1, or 2 atoms selected from O and S, which is substituted by 0, 1, 2 or 3 group(s) selected from F, Cl, Br, $C_{1-6}$alk, $C_{1-4}$haloalk, —$OR^a$, —$OC_{1-4}$haloalk, CN, —C(═O)$R^b$, —C(═O)$OR^a$, —C(═O)$NR^aR^a$, —C(═$NR^a$)$NR^aR^a$, —OC(═O)$R^b$, —OC(═O)$NR^aR^a$, —$OC_{2-6}$alkNRaRa, —$OC_{2-6}$alk$OR^a$, —$SR^a$, —S(═O)$R^b$, —S(═O)$_2R^b$, —S(═O)$_2NR^aR^a$, —$NR^aR^a$, —N($R^a$)C(═O)$R^b$, —N($R^a$)C(═O)$OR^b$, —N($R^a$) C(═O)$NR^aR^a$, —N($R^a$)C(═$NR^a$)$NR^aR^a$, —N($R^a$)S(═O)$_2R^b$, —N($R^a$)S(═O)$_2NR^aR^a$, —$NR^aC_{2-6}$alk$NR^aR^a$, —$NR^aC_{2-6}$alk$OR^a$, —$C_{1-6}$alkN- $R^aR^a$, $—C_{1-6}alkOR^a$, $—C_{1-6}alkN(R^a)C(=O)R^b$, $—C_{1-6}alkOC(=O)R^b$, $—C_{1-6}alkC(=O)NR^aR^a$, $—C_{1-6}alkC(=O)OR^a$, $R^{10}$, and oxo;

$R^{4b}$, $R^{Xn}$, $R^{8b}$, $R^{8b}$, and $R^{9b}$ is independently, at each instance, selected from the group consisting of $C_{1-6}alk$ substituted by 0, 1, 2, 3, 4, or 5 group(s) selected from F, Cl, Br, $—OR^a$, $—OC_{1-4}haloalk$, or CN;

$R^{10}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0 or 1 atoms selected from O and S, which is substituted by 0, 1, 2 or 3 group(s) selected from F, Cl, Br, $C_{1-6}alk$, $C_{1-4}haloalk$, $—OR^a$, $—OC_{1-4}haloalk$, CN, $—C(=O)R^b$, $—C(=O)OR^a$, $—C(=O)NR^aR^a$, $—C(=NR^a)NR^aR^a$, $—OC(=O)R^b$, $—OC(=O)NR^aR^a$, $—OC_{2-6}alkNR^aR^a$, $—OC_{2-6}alkOR^a$, $—SR^a$, $—S(=O)R^b$, $—S(=O)_2R^b$, $—S(=O)_2NR^aR^a$, $—NR^aR^a$, $—N(R^a)C(=O)R^b$, $—N(R^a)C(=O)OR^b$, $—N(R^a)C(=O)NR^aR^a$, $—N(R^a)C(=NR^a)NR^aR^a$, $—N(R^a)S(=O)_2R^b$, $—N(R^a)S(=O)_2NR^aR^a$, $—NR^aC_{2-6}alkNR^aR^a$, $—NR^aC_{2-6}alkOR^a$, $—C_{1-6}alkNR^aR^a$, $—C_{1-6}alkOR^a$, $—C_{1-6}alkN(R^a)C(=O)R^b$, $—C_{1-6}alkOC(=O)R^b$, $—C_{1-6}alkC(=O)NR^aR^a$, $—C_{1-6}alkC(=O)OR^a$, and oxo;

$R^a$ is independently, at each instance, H or $R^b$; and $R^b$ is independently, at each instance, $C_{1-6}alk$, phenyl, or benzyl, wherein the $C_{1-6}alk$ is being substituted by 0, 1, 2 or 3 substituents selected from halo, —OH, $—OC_{1-4}alk$, $—NH_2$, $—NHC_{1-4}alk$, $—OC(=O)C_{1-4}alk$, or $—N(C_{1-4}alk)C_{1-4}alk$; and the phenyl or benzyl is being substituted by 0, 1, 2 or 3 substituents selected from halo, $C_{1-4}alk$, $C_{1-3}haloalk$, —OH, $—OC_{1-4}alk$, $—NH_2$, $—NHC_{1-4}alk$, $—OC(=O)C_{1-4}alk$, or $—N(C_{1-4}alk)C_{1-4}$ alk.

2. The compound according to claim 1, wherein $X^1$ is $CR^6$; $X^2$ is $CR^{3a}$; $X^3$ is N; $X^4$ is $CR^{3c}$; $X^5$ is N; $X^6$ is $CR^{3e}$; and $X^7$ is $CR^{3f}$; having the formula (Ia):

(Ia)

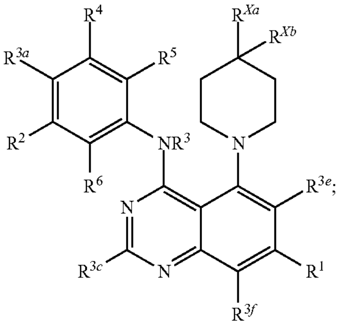

wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-4}alk$, $C_{1-4}haloalk$, $—OR^a$, $—OC_{1-4}haloalk$, CN, $—NR^aR^a$, or oxo.

3. The compound according to claim 1, wherein $X^1$ is N; $X^2$ is $CR^{3a}$; $X^3$ is N; $X^4$ is $CR^{3c}$; $X^5$ is N; $X^6$ is $CR^{3e}$; and $X^7$ is $CR^{3f}$; having the formula (Ib):

(Ib)

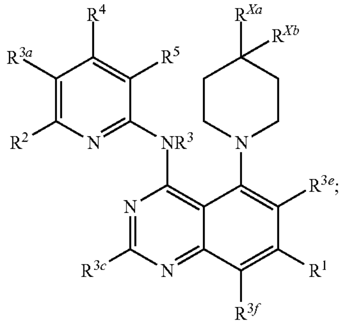

wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-4}alk$, $C_{1-4}haloalk$, $—OR^a$, $—OC_{1-4}haloalk$, CN, $—NR^aR^a$, or oxo.

4. The compound according to claim 1, wherein $X^1$ is $CR^6$; $X^2$ is N; $X^3$ is N; $X^4$ is $CR^{3c}$; $X^5$ is N; $X^6$ is $CR^{3e}$; and $X^7$ is $CR^{3f}$; having the formula (Ic):

(Ic)

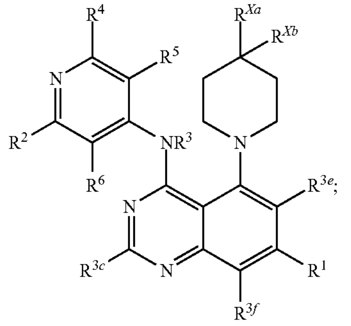

wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-4}alk$, $C_{1-4}haloalk$, $—OR^a$, $—OC_{1-4}haloalk$, CN, $—NR^aR^a$, or oxo.

5. The compound according to claim 1, wherein $X^1$ is N; $X^2$ is N; $X^3$ is N; $X^4$ is $CR^{3c}$; $X^5$ is N; $X^6$ is $CR^{3e}$; and $X^7$ is $CR^{3f}$; having the formula (Id):

(Id)

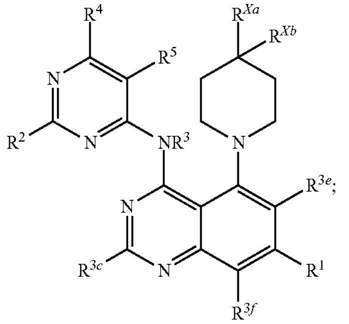

wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-4}$alk, $C_{1-4}$haloalk, —$OR^a$, —$OC_{1-4}$haloalk, CN, —$NR^aR^a$, or oxo.

6. The compound according to claim 1, wherein $X^1$ is $CR^6$; $X^2$ is $CR^{3a}$; $X^3$ is N; $X^4$ is N; $X^5$ is $CR^{3d}$; $X^6$ is $CR^{3e}$; and $X^7$ is $CR^{3f}$; having the formula (Ie):

(Ie)

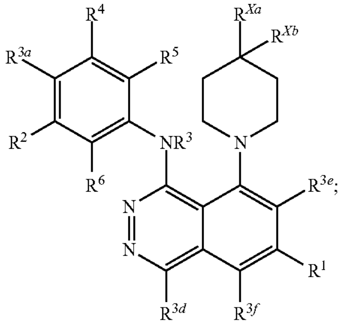

wherein said $R^{Xa}$ and $R^{Xb}$ pair can combine with the carbon atom attached to each of them to form a saturated or partially-saturated 3-, 4-, 5-, 6-membered monocyclic ring spiro to the piperidinyl ring; wherein said 3-, 4-, 5-, 6-membered monocyclic ring contains 0 N, O, and S atoms, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, —$OR^a$, —$OC_{1-4}$haloalk, CN, —$NR^aR^a$, or oxo.

7. The compound according to claim 1, wherein $R^3$ is H or methyl.

8. The compound according to claim 1, wherein each of $R^{Xc}$, $R^{Xd}$, $R^{Xe}$, $R^{Xf}$, $R^{Xg}$, $R^{Xh}$, $R^{Xi}$, and $R^{Xj}$ is H, halo, $C_{1-6}$alk, or $C_{1-4}$haloalk; and each of $R^{Xa}$ and $R^{Xb}$ pair combine with the carbon atom attached to each of them form a saturated 3-, 4-, or 5-membered monocyclic ring spiro to the piperidinyl ring; wherein said ring contains 0, 1, 2 or 3 N atoms and 0 or 1 atoms selected from O and S.

9. The compound according to claim 1, wherein each of $R^{Xc}$, $R^{Xd}$, $R^{Xe}$, $R^{Xf}$, $R^{Xg}$, $R^{Xh}$, $R^{Xi}$, and $R^{Xj}$ is H, methyl, or ethyl; and each of $R^{Xa}$ and $R^{Xb}$ pair combine with the carbon atom attached to each of them form a cyclopropyl, cyclobutyl, or cyclopentyl ring spiro to the piperidinyl ring.

10. The compound according to claim 1, wherein the group

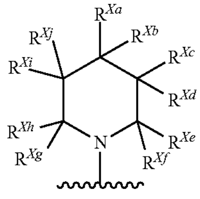

is selected from

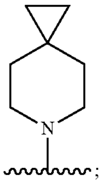; 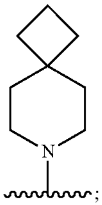; 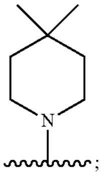; or 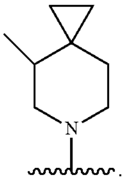.

11. The compound according to claim 1, wherein the group

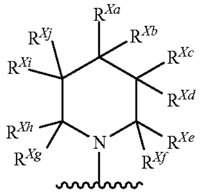

is

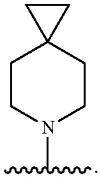.

12. The compound according to claim 1, wherein $R^1$ is —CN, or a group —Z—$R^8$, wherein Z is absent, —NH—, —$NHSO_2$—, —$SO_2NH$—, —N═S(═O)—$(R^7)_2$ (wherein the two $R^7$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S), —S(═O)(═NH)—, —S—, —S(═O)—, —$SO_2$—, —(C═O)—, —(C═O)NH—, or —NH(C═O)—; and (a) $R^8$ is H;

(b) $R^8$ is oxetanyl, cyclopropyl; or (c) $R^8$ is $C_{1-6}$alk substituted by 0, 1, 2 or 3 OH group(s).

13. The compound according to claim 1, wherein $R^1$ is a group —Z—$R^8$, wherein Z is —N═S(═O)—$(R^7)_2$; wherein each $R^7$ is independently selected from the group consisting of H, methyl, or isopropyl; or the two $R^7$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S, which is selected from:

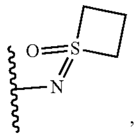
,
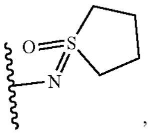
, or
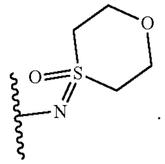
.

14. The compound according to claim 1, wherein $R^1$ is a group —Z—$R^8$, wherein Z is —$SO_2$; —$NHSO_2$—; —$SO_2NH$—; or —S(═O)(═NH)—; and $R^8$ is H, oxetanyl, cyclopropyl, or $R^8$ is $C_{1-6}$alk substituted by 0, 1, 2 or 3 OH group(s).

15. The compound according to claim 1, wherein $R^1$ is a group —Z—$R^8$, wherein Z is —$NHSO_2$— and $R^8$ is —$CH_2$—$CH_2$—OH.

16. The compound according to claim 1, wherein $R^1$ is a group —Z—$R^8$, wherein Z is —$SO_2$; and $R^8$ is methyl.

17. The compound according to claim 1, wherein $R^1$ is a group —Z—$R^8$, wherein Z is —S(═O)(═NH)—; and $R^8$ is cyclopropyl.

18. The compound according to claim 1, wherein $R^1$ is H.

19. The compound according to claim 1, wherein $R^2$ is halo or a group —Y—$R^9$, wherein Y is absent, —NH—, —NH—$(CH_2)_{0-4}$—, or —O—$(CH_2)_{0-4}$; and $R^9$ is a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —OH, —$OC_{1-4}$ haloalk, CN, $R^{10}$, and oxo; or $R^9$ is $C_{1-6}$alk substituted by 0, 1, 2, 3, 4, or 5 group(s) selected from F, Cl, Br, —OH, —$OC_{1-4}$haloalk, or CN.

20. The compound according to claim 1, wherein $R^2$ is a saturated 5- or 6-membered monocyclic ring wherein each said ring contains 0, 1, or 2 N atoms and 0 or 1 O atom, and wherein each said ring is substituted by 0, 1, 2 or 3 group(s) selected from F, Cl, Br, $C_{1-6}$alk, $C_{1-4}$haloalk, —OH, —$OC_{1-4}$ haloalk, CN, $R^{10}$, and oxo.

21. The compound according to claim 1, wherein $R^2$ is (a) halo; (b) a group —Y—$R^9$, wherein Y is absent; and $R^9$ is morpholinyl, piperidinyl, azetidinyl, pyrrolidinyl, cyclopropyl, cyclobutyl, cyclopentyl, cyclohexyl, piperazinyl, tetrahydrofuranyl,

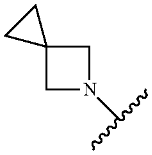
,
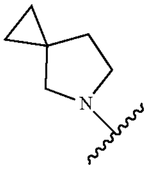
,
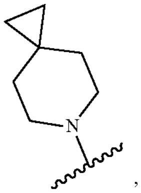
,
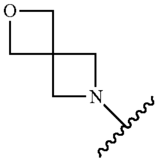
,
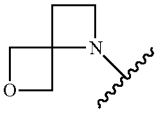
,
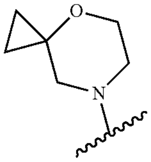
,
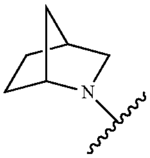
,
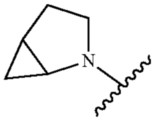
,
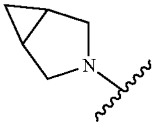
, -continued

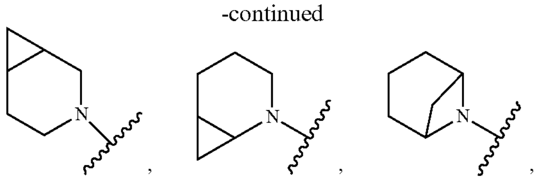
, , ,
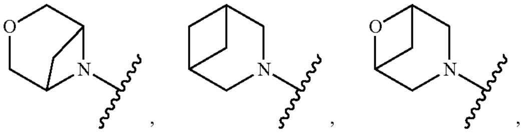
, , ,
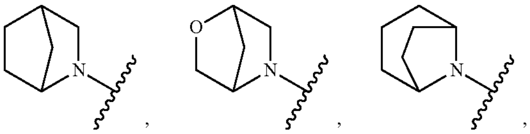
, , ,
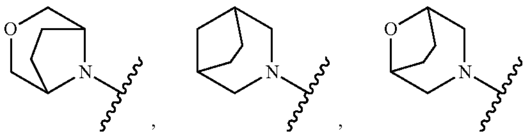
, , ,
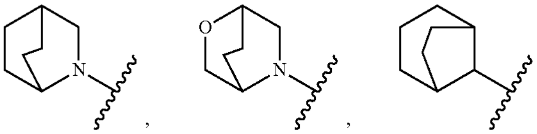
, , ,
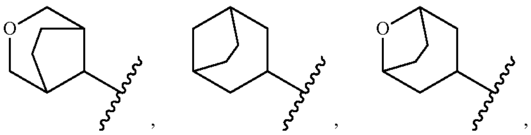
, , ,
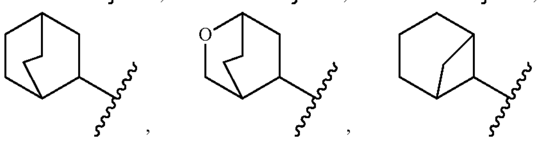
, , ,
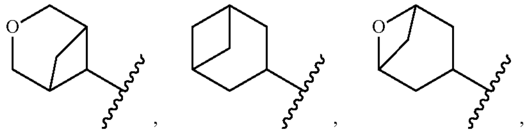
, , ,
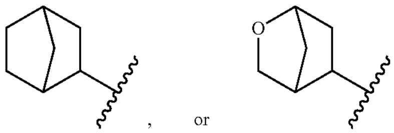
, or ,;

wherein each said ring is substituted by 0, 1, 2 or 3 group(s) selected from F, Cl, Br, methyl, $CF_3$, —OH, —$OCHF_2$, CN, and oxo; or (c) a group —Y—$R^9$, wherein Y is NH, —O—, —O—$(CH_2)$—, —O—$(CH_2)$—$(CH_2)$—, or —O—$(CH_2)$—$(CH_2)$—$(CH_2)$—, and wherein $R^9$ is

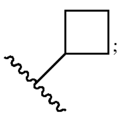
;
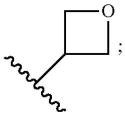
; or
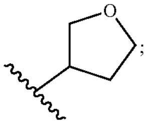
;

or $R^9$ is $C_{1-6}$alk substituted by 0, 1, 2, 3, 4, or 5 group(s) selected from F, Cl, Br, methyl, $CF_3$, —OH, or CN.

22. The compound according to claim 1, wherein $R^2$ is morpholinyl or piperidinyl substituted by 0, 1, 2 or 3 group(s) selected from F, Cl, Br, methyl, $CF_3$, —OH, —$OCHF_2$, CN, or oxo.

23. The compound according to claim 1, wherein $R^2$ is morpholinyl substituted by 1, 2 or 3 methyl group(s).

24. The compound according to claim 1, wherein $R^2$ is piperidinyl substituted by 1, 2 or 3 fluoro group(s).

25. The compound according to claim 1, wherein $R^2$ is

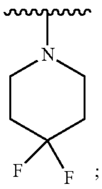 ; 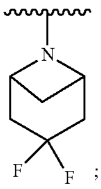 ; 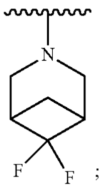 ; or 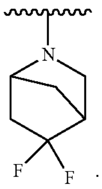 .

26. The compound according to claim 1, wherein $R^2$ is methyl or —O—(CH$_2$)—(CH$_2$)—CF$_3$.

27. The compound according to claim 1, wherein Z is absent, —NH—, —NHSO$_2$—, —SO$_2$NH—, —N═S(═O)<(R$^a$)$_2$— (wherein each $R^7$ is independently selected from the group consisting of H, methyl, or isopropyl), —S(═O)(═NH)—, —S—, —S(═O)—, —SO$_2$—, —(C═O)—, —(C═O)NH—, or —NH(C═O)—.

28. The compound according to claim 1, wherein $R^8$ is selected from (a) H; (b) $C_{1-6}$alk substituted by 0, 1, 2 or 3 group(s) selected from F, Cl, Br, —OH, —OCH$_3$, or cyclopropyl; or (c) a saturated, partially-saturated or unsaturated 3-, 4-, 5-, 6-, or 7-membered monocyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —$C_{1-6}$alkOH, —OH, —OCH$_3$, —NH$_2$, or oxo.

29. The compound according to claim 1, wherein $R^8$ is selected from cyclopropyl, cyclobutyl, cyclopentyl, oxetanyl, azetidinyl, tetrahydrofuranyl, or 1,3,4-oxathiazinanyl.

30. The compound according to claim 1, wherein $R^3$ is H.

31. The compound according to claim 1, wherein $R^4$ is selected from (a) H; (b) $C_{1-6}$alk substituted by 0, 1, 2 or 3 OH group(s); or (c) cyclopropyl.

32. The compound according to claim 1, wherein $R^4$ is methyl.

33. The compound according to claim 1, wherein $R^5$ is H.

34. The compound according to claim 1, wherein $R^6$ is H or F.

35. The compound according to claim 1, wherein $R^{3a}$ is H or F.

36. The compound according to claim 1, wherein $R^{3b}$ is H.

37. The compound according to claim 1, wherein $R^{3c}$ is H.

38. The compound according to claim 1, wherein $R^{3d}$ is H.

39. The compound according to claim 1, wherein $R^{3e}$ is H.

40. The compound according to claim 1, wherein $R^{3f}$ is H.

41. The compound according to claim 1, or any pharmaceutically-acceptable salt thereof; selected from the group consisting of:

N-(4-((3-(4,4-Difluoropiperidin-1-yl)-5-methylphenyl)amino)-5-(6-azaspiro[2.5]octan-6-yl)quinazolin-7-yl)-2-hydroxyethane-1-sulfonamide;

N-(4-((3-(4,4-Difluoropiperidin-1-yl)-5-methylphenyl)amino)-2-methyl-5-(6-azaspiro[2.5]octan-6-yl)quinazolin-7-yl)-2-hydroxyethane-1-sulfonamide;

N-(3-(4,4-Difluoropiperidin-1-yl)-5-methylphenyl)-7-(methylsulfonyl)-5-(6-azaspiro[2.5]octan-6-yl)quinazolin-4-amine;

N-(3-(4,4-Difluoropiperidin-1-yl)-5-methylphenyl)-5-(6-azaspiro[2.5]octan-6-yl)quinazolin-4-amine;

(R)-Cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone;

(S)-Cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone;

2-Hydroxy-N-(4-((3-methyl-5-(3,3,3-trifluoropropoxy)phenyl)amino)-5-(6-azaspiro[2.5]octan-6-yl)quinazolin-7-yl)ethane-1-sulfonamide;

N-(4-((3,5-Dimethylphenyl)amino)-5-(6-azaspiro[2.5]octan-6-yl)quinazolin-7-yl)-2-hydroxyethane-1-sulfonamide;

N-(5-(6-Azaspiro[2.5]octan-6-yl)-4-((3-(3,3,3-trifluoropropoxy)phenyl)amino)quinazolin-7-yl)-2-hydroxyethane-1-sulfonamide;

N-(4-((2-(4,4-Difluoropiperidin-1-yl)-6-methylpyrimidin-4-yl)amino)-5-(6-azaspiro[2.5]octan-6-yl)quinazolin-7-yl)-2-hydroxyethane-1-sulfonamide;

N-(4-((2-(4,4-Difluoropiperidin-1-yl)-6-methylpyridin-4-yl)amino)-5-(6-azaspiro[2.5]octan-6-yl)quinazolin-7-yl)-2-hydroxyethane-1-sulfonamide;

N-(4-((6-(4,4-Difluoropiperidin-1-yl)-4-methylpyridin-2-yl)amino)-5-(6-azaspiro[2.5]octan-6-yl)quinazolin-7-yl)-2-hydroxyethane-1-sulfonamide;

N-(4-(3-(4,4-Difluoropiperidin-1-yl)-5-methylphenoxy)-5-(6-azaspiro[2.5]octan-6-yl)quinazolin-7-yl)-2-hydroxyethane-1-sulfonamide;

N-(1-((3-(4,4-Difluoropiperidin-1-yl)-5-methylphenyl)amino)-8-(6-azaspiro[2.5]octan-6-yl)phthalazin-6-yl)-2-hydroxyethane-1-sulfonamide;

(R)-2-Hydroxy-N-(4-((3-methyl-5-(2-methylmorpholino)phenyl)amino)-5-(6-azaspiro[2.5]octan-6-yl)quinazolin-7-yl)ethane-1-sulfonamide;

(R)-2-Hydroxy-N-(4-((4-methyl-6-(2-methylmorpholino)pyridin-2-yl)amino)-5-(6-azaspiro[2.5]octan-6-yl)quinazolin-7-yl)ethane-1-sulfonamide;

(R)-2-Hydroxy-N-(4-((6-methyl-2-(2-methylmorpholino)pyrimidin-4-yl)amino)-5-(6-azaspiro[2.5]octan-6-yl)quinazolin-7-yl)ethane-1-sulfonamide;

2-Hydroxy-N-(4-((2-((1-hydroxy-2-methylpropan-2-yl)amino)-6-methylpyrimidin-4-yl)amino)-5-(6-azaspiro[2.5]octan-6-yl)quinazolin-7-yl)ethane-1-sulfonamide;

N-(4-((2-Fluoro-3-((1-hydroxy-2-methylpropan-2-yl)amino)phenyl)amino)-5-(6-azaspiro[2.5]octan-6-yl)quinazolin-7-yl)-2-hydroxyethane-1-sulfonamide;

2-Hydroxy-N-(4-((3-(2-hydroxy-2-methylpropoxy)phenyl)amino)-5-(6-azaspiro[2.5]octan-6-yl)quinazolin-7-yl)ethane-1-sulfonamide;

4-((2-(4,4-Difluoropiperidin-1-yl)-6-methylpyrimidin-4-yl)amino)-N-(3-methyloxetan-3-yl)-5-(6-azaspiro[2.5]octan-6-yl)quinazoline-7-sulfonamide;

(S)—N-(4-((6-(4,4-Difluoropiperidin-1-yl)-4-methylpyridin-2-yl)amino)-5-(6-azaspiro[2.5]octan-6-yl)quinazolin-7-yl)-1-hydroxypropane-2-sulfonamide;

(R)—N-(4-((6-(4,4-Difluoropiperidin-1-yl)-4-methylpyridin-2-yl)amino)-5-(6-azaspiro[2.5]octan-6-yl)quinazolin-7-yl)-1-hydroxypropane-2-sulfonamide;

N-(4-((2-(3,3-Difluoroazetidin-1-yl)-6-methylpyrimidin-4-yl)amino)-5-(6-azaspiro[2.5]octan-6-yl)quinazolin-7-yl)-2-hydroxyethane-1-sulfonamide;

N-(4-((2-(4,4-Difluoropiperidin-1-yl)-6-methylpyrimidin-4-yl)amino)-8-fluoro-5-(6-azaspiro[2.5]octan-6-yl)quinazolin-7-yl)-2-hydroxyethane-1-sulfonamide;

N-(4-((2-(4,4-Difluoropiperidin-1-yl)-6-methylpyrimidin-4-yl)amino)-5-(6-azaspiro[2.5]octan-6-yl)pyrido[4,3-d]pyrimidin-7-yl)-2-hydroxyethane-1-sulfonamide;

N-(4-((2-(4,4-Difluoropiperidin-1-yl)-6-methylpyrimidin-4-yl)amino)-5-(7-azaspiro[3.5]nonan-7-yl)quinazolin-7-yl)-2-hydroxyethane-1-sulfonamide;

N-(4-((2-(4,4-Difluoropiperidin-1-yl)pyrimidin-4-yl)amino)-5-(4,4-dimethylazepan-1-yl)quinazolin-7-yl)-2-hydroxyethane-1-sulfonamide;

2-((4-((2-(4,4-Difluoropiperidin-1-yl)-6-methylpyrimidin-4-yl)amino)-5-(6-azaspiro[2.5]octan-6-yl)quinazolin-7-yl)sulfonyl)ethan-1-ol;

N-(4-((3-(4,4-Difluoropiperidin-1-yl)-5-methylphenyl)thio)-5-(6-azaspiro[2.5]octan-6-yl)quinazolin-7-yl)-2-hydroxyethane-1-sulfonamide;

7-(Azetidin-3-ylsulfonyl)-N-(2-(4,4-difluoropiperidin-1-yl)-6-methylpyrimidin-4-yl)-5-(6-azaspiro[2.5]octan-6-yl)quinazolin-4-amine;

N-(tert-Butyl)-3-((7-((2-hydroxyethyl)sulfonamido)-5-(6-azaspiro[2.5]octan-6-yl)quinazolin-4-yl)amino)benzenesulfonamide;

N-(4-((3-(Cyclopentylsulfonyl)-4-methylphenyl)amino)-5-(6-azaspiro[2.5]octan-6-yl)quinazolin-7-yl)-2-hydroxyethane-1-sulfonamide;

N-(tert-Butyl)-4-((6-(N-(tert-butyl)sulfamoyl)pyridin-2-yl)amino)-5-(6-azaspiro[2.5]octan-6-yl)quinazoline-7-sulfonamide;

N-(tert-Butyl)-4-(chroman-5-ylamino)-5-(6-azaspiro[2.5]octan-6-yl)quinazoline-7-sulfonamide;

N-(1-((6-(4,4-Difluoropiperidin-1-yl)-4-methylpyridin-2-yl)amino)-8-(6-azaspiro[2.5]octan-6-yl)phthalazin-6-yl)-2-hydroxyethane-1-sulfonamide;

N-(1-((6-(4,4-Difluoropiperidin-1-yl)-4-methylpyridin-2-yl)amino)-8-(6-azaspiro[2.5]octan-6-yl)isoquinolin-6-yl)-2-hydroxyethane-1-sulfonamide;

N-(1-((3-(4,4-Difluoropiperidin-1-yl)-5-methylphenyl)amino)-8-(6-azaspiro[2.5]octan-6-yl)isoquinolin-6-yl)-2-hydroxyethane-1-sulfonamide;

2-(4-((3-(4,4-Difluoropiperidin-1-yl)-5-methylphenyl)amino)-5-(6-azaspiro[2.5]octan-6-yl)quinazolin-7-yl)isothiazolidine 1,1-dioxide;

N-(4-((3-(3,3-Difluoro-6-azabicyclo[3.1.1]heptan-6-yl)-5-methylphenyl)amino)-5-(6-azaspiro[2.5]octan-6-yl)quinazolin-7-yl)-2-hydroxyethane-1-sulfonamide;

N-(4-((3-(6,6-Difluoro-3-azabicyclo[3.1.1]heptan-3-yl)-5-methylphenyl)amino)-5-(6-azaspiro[2.5]octan-6-yl)quinazolin-7-yl)-2-hydroxyethane-1-sulfonamide;

N-(4-((3-(4,4-Difluoropiperidin-1-yl)-4-methylphenyl)amino)-5-(6-azaspiro[2.5]octan-6-yl)quinazolin-7-yl)-2-hydroxyethane-1-sulfonamide;

4-((3-(4,4-Difluoropiperidin-1-yl)-5-methylphenyl)amino)-N-(2-hydroxyethyl)-5-(6-azaspiro[2.5]octan-6-yl)quinazoline-7-carboxamide;

2-((8-((3-(4,4-Difluoropiperidin-1-yl)-5-methylphenyl)amino)-1-(6-azaspiro[2.5]octan-6-yl)-2,7-naphthyridin-3-yl)amino)-2-methylpropan-1-ol;

2-((5-((3-(4,4-Difluoropiperidin-1-yl)-5-methylphenyl)amino)-4-(6-azaspiro[2.5]octan-6-yl)-1,6-naphthyridin-2-yl)amino)-2-methylpropan-1-ol;

2-((5-((3-(4,4-Difluoropiperidin-1-yl)-5-methylphenyl)amino)-4-(6-azaspiro[2.5]octan-6-yl)pyrido[4,3-d]pyrimidin-2-yl)amino)-2-methylpropan-1-ol;

2-(4-((3-(4,4-Difluoropiperidin-1-yl)-5-methylphenyl)amino)-5-(6-azaspiro[2.5]octan-6-yl)quinazolin-7-yl)propan-2-ol; or N-(3-(4,4-Difluoropiperidin-1-yl)-5-methylphenyl)-5-(6-azaspiro[2.5]octan-6-yl)pyrido[3,4-d]pyrimidin-4-amine.

42. The compound of claim 1, selected from the group consisting of:

| Example # | Chemical Structure | Name |
|---|---|---|
| 100 | 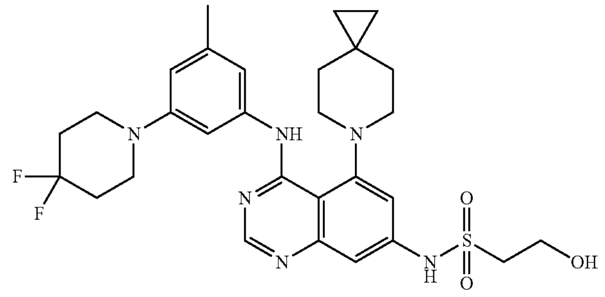 [SMILES: Cc1cc(Nc2ncnc3cc(NS(=O)(=O)CCO)cc(N4CCC5(CC4)CC5)c23)cc(N2CCC(F)(F)CC2)c1] | N-(4-((3-(4,4-Difluoropiperidin-1-yl)-5-methylphenyl)amino)-5-(6-azaspiro[2.5]octan-6-yl)quinazolin-7-yl)-2-hydroxyethane-1-sulfonamide |
| 100-1 | 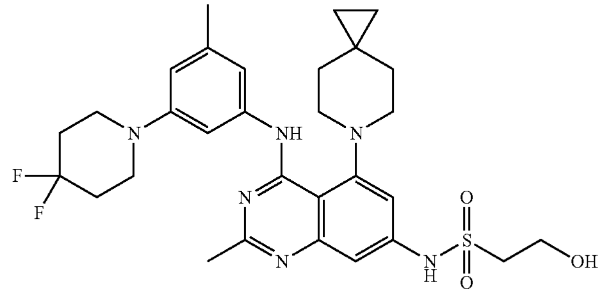 [SMILES: Cc1cc(Nc2nc(C)nc3cc(NS(=O)(=O)CCO)cc(N4CCC5(CC4)CC5)c23)cc(N2CCC(F)(F)CC2)c1] | N-(4-((3-(4,4-Difluoropiperidin-1-yl)-5-methylphenyl)amino)-2-methyl-5-(6-azaspiro[2.5]octan-6-yl)quinazolin-7-yl)-2-hydroxyethane-1-sulfonamide |

-continued

| Example # | Chemical Structure | Name |
|---|---|---|
| 101 | 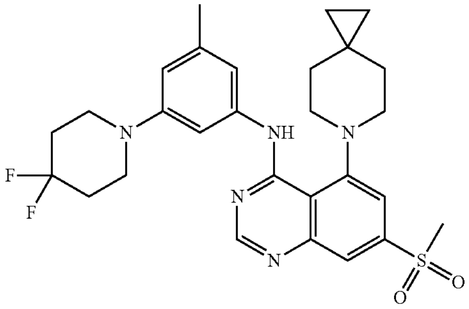 [SMILES: Cc1cc(Nc2ncnc3cc(S(C)(=O)=O)cc(N4CCC5(CC4)CC5)c23)cc(N2CCC(F)(F)CC2)c1] | N-(3-(4,4-Difluoropiperidin-1-yl)-5-methylphenyl)-7-(methylsulfonyl)-5-(6-azaspiro[2.5]octan-6-yl)quinazolin-4-amine |
| 101-1 | 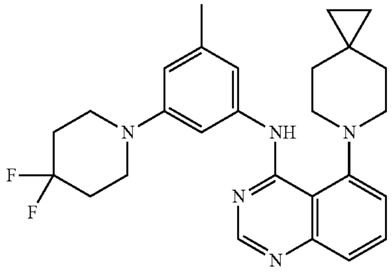 [SMILES: Cc1cc(Nc2ncnc3cccc(N4CCC5(CC4)CC5)c23)cc(N2CCC(F)(F)CC2)c1] | N-(3-(4,4-Difluoropiperidin-1-yl)-5-methylphenyl)-5-(6-azaspiro[2.5]octan-6-yl)quinazolin-4-amine |
| 102-1 | 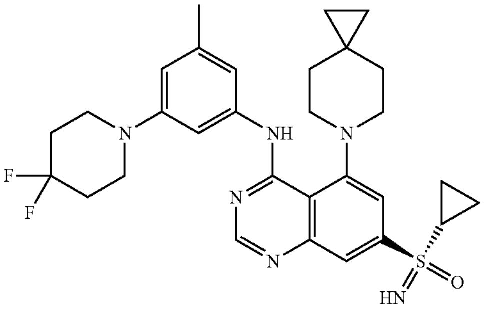 [SMILES: Cc1cc(Nc2ncnc3cc([S@](=N)(=O)C4CC4)cc(N4CCC5(CC4)CC5)c23)cc(N2CCC(F)(F)CC2)c1] | (R)-Cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone |
| 102-2 | 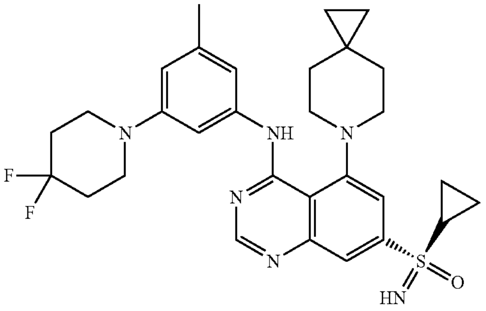 [SMILES: Cc1cc(Nc2ncnc3cc([S@@](=N)(=O)C4CC4)cc(N4CCC5(CC4)CC5)c23)cc(N2CCC(F)(F)CC2)c1] | (S)-Cyclopropyl(4-((3-(4,4-difluoropiperidin-1-yl)-5-methylphenyl)amino)-5-(6-azaspiro[2.5]octan-6-yl)quinazolin-7-yl)(imino)-16-sulfanone |
| 103 | 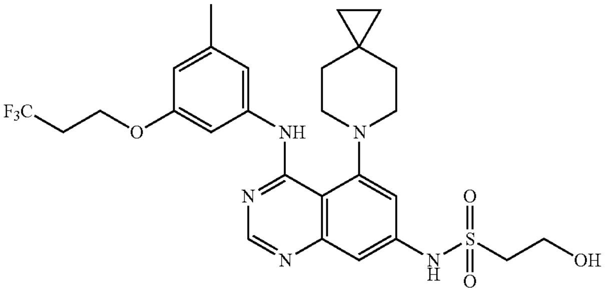 [SMILES: Cc1cc(Nc2ncnc3cc(NS(=O)(=O)CCO)cc(N4CCC5(CC4)CC5)c23)cc(OCCC(F)(F)F)c1] | 2-Hydroxy-N-(4-((3-methyl-5-(3,3,3-trifluoropropoxy)phenyl)amino)-5-(6-azaspiro[2.5]octan-6-yl)quinazolin-7-yl)ethane-1-sulfonamide |

-continued

| Example # | Chemical Structure | Name |
|---|---|---|
| 103-1 | 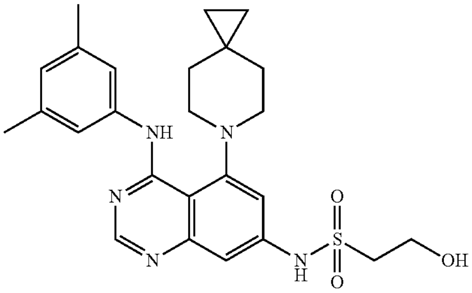 [SMILES: Cc1cc(C)cc(Nc2ncnc3cc(NS(=O)(=O)CCO)cc(N4CCC5(CC4)CC5)c23)c1] | N-(4-((3,5-Dimethylphenyl) amino)-5-(6-azaspiro[2.5]octan-6-yl)quinazolin-7-yl)-2-hydroxyethane-1-sulfonamide |
| 103-2 | 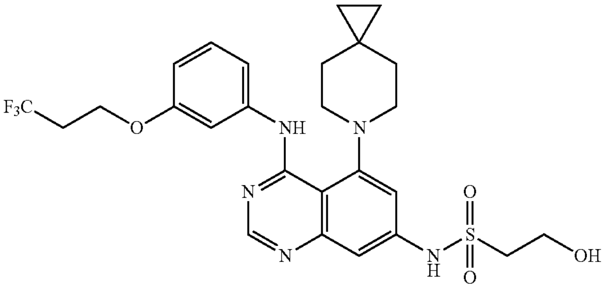 [SMILES: O=S(=O)(CCO)Nc1cc(N2CCC3(CC2)CC3)c2c(Nc3cccc(OCCC(F)(F)F)c3)ncnc2c1] | N-(5-(6-Azaspiro[2.5]octan-6-yl)-4-((3-(3,3,3-trifluoropropoxy)phenyl)amino) quinazolin-7-yl)-2-hydroxyethane-1-sulfonamide |
| 104 | 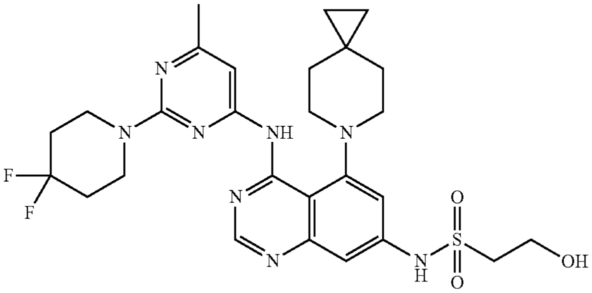 [SMILES: Cc1cc(Nc2ncnc3cc(NS(=O)(=O)CCO)cc(N4CCC5(CC4)CC5)c23)nc(N2CCC(F)(F)CC2)n1] | N-(4-((2-(4,4-Difluoro-piperidin-1-yl)-6-methylpyrimidin-4-yl) amino)-5-(6-azaspiro[2.5] octan-6-yl)quinazolin-7-yl)-2-hydroxyethane-1-sulfonamide |
| 105 | 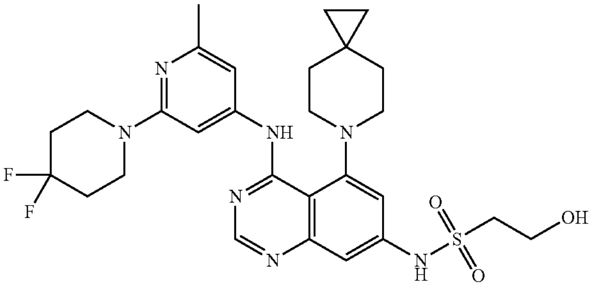 [SMILES: Cc1cc(Nc2ncnc3cc(NS(=O)(=O)CCO)cc(N4CCC5(CC4)CC5)c23)cc(N2CCC(F)(F)CC2)n1] | N-(4-((2-(4,4-Difluoropiperidin-1-yl)-6-methylpyridin-4-yl) amino)-5-(6-azaspiro[2.5]octan-6-yl)quinazolin-7-yl)-2-hydroxyethane-1-sulfonamide |
| 105-1 | 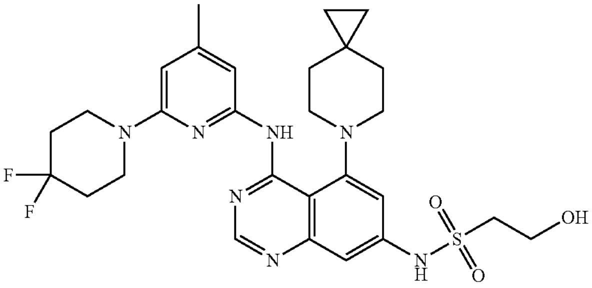 [SMILES: Cc1cc(Nc2ncnc3cc(NS(=O)(=O)CCO)cc(N4CCC5(CC4)CC5)c23)nc(N2CCC(F)(F)CC2)c1] | N-(4-((6-(4,4-Difluoropiperidin-1-yl)-4-methylpyridin-2-yl) amino)-5-(6-azaspiro[2.5]octan-6-yl)quinazolin-7-yl)-2-hydroxyethane-1-sulfonamide |

-continued

| Example # | Chemical Structure | Name |
| --- | --- | --- |
| 105-2 | 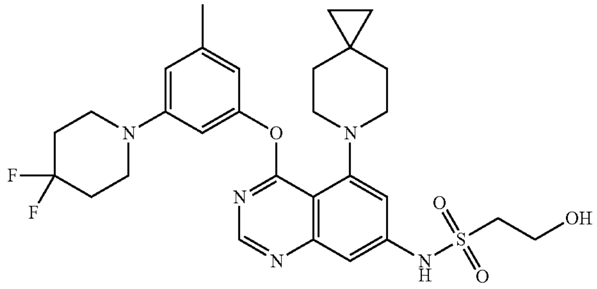 | N-(4-(3-(4,4-Difluoropiperidin-1-yl)-5-methylphenoxy)-5-(6-azaspiro[2.5]octan-6-yl) quinazolin-7-yl)-2-hydroxyethane-1-sulfonamide |
| 106 | 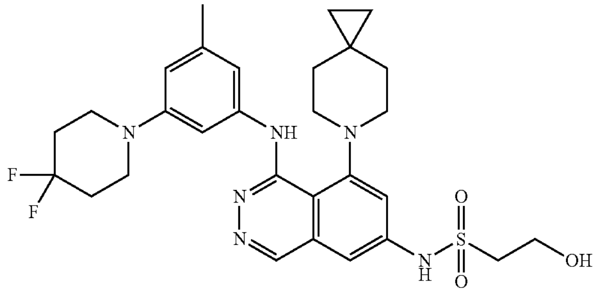 [SMILES: Cc1cc(Nc2nncc3cc(NS(=O)(=O)CCO)cc(N4CCC5(CC4)CC5)c23)cc(N2CCC(F)(F)CC2)c1] | N-(1-((3-(4,4-Difluoropiperidin-1-yl)-5-methylphenyl)amino)-8-(6-azaspiro[2.5]octan-6-yl) phthalazin-6-yl)-2-hydroxy-ethane-1-sulfonamide; |

or any pharmaceutically-acceptable salt thereof.

43. A pharmaceutical composition comprising the compound according to claim 1 or the pharmaceutically acceptable salt thereof, and a pharmaceutically-acceptable diluent or carrier.

44. A method of treating a condition that may be treated with KIF18a inhibitors, the method comprising administering to a patient in need thereof a therapeutically effective amount of the compound in accordance with claim 1, wherein said condition is cancer selected from the group consisting of melanoma, prostate cancer, cervical cancer, breast cancer, colon cancer, sarcoma, or leukemia.

45. A method of treating a cell proliferation disorder in a subject the method comprising administering to the subject in need thereof a therapeutically effective amount of the compound in accordance with claim 1, wherein said disorder is cancer selected from the group consisting of melanoma, prostate cancer, cervical cancer, breast cancer, colon cancer, sarcoma, or leukemia.

46. A method of inhibiting KIF18A in a cell, comprising contacting the cell with a compound, or pharmaceutically acceptable salts thereof, in accordance with claim 1.

* * * * *